US007022707B2

(12) United States Patent
Adams et al.

(10) Patent No.: US 7,022,707 B2
(45) Date of Patent: Apr. 4, 2006

(54) PIPERAZINE DERIVATIVES

(75) Inventors: David Reginald Adams, Wokingham (GB); Jonathan Mark Bentley, Wokingham (GB); James Edward Paul Davidson, Wokingham (GB); Claire Elizabeth Dawson, Wokingham (GB); Ashley Roger George, Wokingham (GB); Howard Langham Mansell, Wokingham (GB); Patrizio Mattei, Riehen (CH); Jacques Mizrahi, Basel (CH); Matthias Heinrich Nettekoven, Grenzach-Wyhlen (DE); Robert Mark Pratt, Wokingham (GB); Stephan Roever, Inzlingen (DE); Jonathan Richard Anthony Roffey, Wokingham (GB); Jean-Luc Specklin, Kembs-Schaferhof (FR); Henri Stalder, Basel (CH); Kerry Wilkinson, Wokingham (GB)

(73) Assignees: Hoffman-La Roche Inc., Nutley, NJ (US); Vernalis Research Limited, Workingham (GB)

( * ) Notice: Subject to any disclaimer, the term of this patent is extended or adjusted under 35 U.S.C. 154(b) by 0 days.

(21) Appl. No.: 10/874,662

(22) Filed: Jun. 23, 2004

(65) Prior Publication Data

US 2004/0235859 A1 Nov. 25, 2004

Related U.S. Application Data

(63) Continuation of application No. 10/010,058, filed on Dec. 7, 2001, now abandoned.

(30) Foreign Application Priority Data

Dec. 15, 2000 (EP) .................................... 0030710

(51) Int. Cl.
*A61K 31/4965* (2006.01)
*A61K 31/497* (2006.01)
*C07D 295/185* (2006.01)
*C07D 295/192* (2006.01)
*C07D 241/04* (2006.01)

(52) U.S. Cl. ........................... 514/252.12; 514/255.01; 544/383; 544/389

(58) Field of Classification Search ............... 544/38.3, 544/389; 514/255.01, 252.12
See application file for complete search history.

(56) References Cited

U.S. PATENT DOCUMENTS

| | | | |
|---|---|---|---|
| 3,933,802 | A | 1/1976 | Ferrini et al. |
| 4,598,089 | A | 7/1986 | Hadvary et al. |
| 4,931,463 | A | 6/1990 | Barbier et al. |
| 4,983,746 | A | 1/1991 | Barbier et al. |
| 5,245,056 | A | 9/1993 | Karpf et al. |
| 5,494,928 | A | 2/1996 | Bös |
| 5,756,817 | A | 5/1998 | Choi et al. |
| 5,977,116 | A | 11/1999 | Castro Pineiro et al. |
| 6,004,996 | A | 12/1999 | Shah et al. |

FOREIGN PATENT DOCUMENTS

| | | | |
|---|---|---|---|
| EP | 185 359 | | 6/1986 |
| EP | 189 577 | | 8/1986 |
| EP | 443 449 | | 8/1991 |
| EP | 524 495 | | 1/1993 |
| EP | 655 440 | | 5/1995 |
| FR | 75 26228 | * | 3/1977 |
| FR | 2 321 890 | | 4/1977 |
| FR | 2 744 449 | | 8/1997 |
| WO | WO 98/30548 | | 7/1998 |
| WO | WO 99/34786 | | 7/1999 |
| WO | WO 00/09122 | | 2/2000 |
| WO | WO 00/09123 | | 2/2000 |
| WO | WO 00/35922 | | 6/2000 |

OTHER PUBLICATIONS

Hartman et al. Chemical Abstracts, vol. 133, No. 238020, Abstract for WO 2000/051611 (Sep. 8, 2000).*
Yung-Chi et al., Biochem Pharmacol, vol. 22(23), pp. 3099-3108 (1973).
Curson et al., Psychopharmacol, vol. 96, pp. 93-100 (1988).
Curson et al., European J. Pharmacol., vol. 141, pp. 429-435 (1987).
C. T. Dourish et al., Psychopharmacol., vol. 113, pp. 369-377 (1994).

(Continued)

*Primary Examiner*—Peter O'Sullivan
(74) *Attorney, Agent, or Firm*—George W. Johnston; Dennis P. Tramaloni; Samuel H. Megerditchian

(57) ABSTRACT

The present invention is a chemical compound of formula (I)

(I)

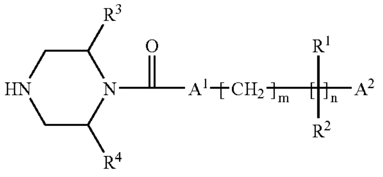

or a pharmaceutically acceptable salts, solvates and esters thereof, wherein $R^1$ to $R^4$, $A^1$, $A^2$ m and n are as described in the specification.

43 Claims, No Drawings

OTHER PUBLICATIONS

A. E. Walsh et al., Psychopharmacol., vol. 116, pp. 120-122 (1994).

Sargeant et al., Psychopharmacol., vol. 133, pp. 309-312 (1997).

L. H. Tecott et al., Nature, vol. 374, pp. 542-546 (1995).

G.A.Kennett et al., Neuropharmacol., vol. 36, pp. 609-620 (1997).

D.Hoyer et al., European J.Pharmacol., vol. 118, pp. 13-23 (1985).

K. Schmuck, et al., FEBS Lett., vol. 342, pp. 85-90 (1994).

Papageorgiou, Org. Lett., vol. 2(8), pp. 1049-1051 (2000).

McKenna et al., J. of Neuroscience, vol. 9(10), pp. 3482-3490 (1989).

S. Parker, "Obesity: Trends and Treatments", Scrip Reports (1996).

Abstract No. CA-2132887 (1995).

Abstract No. CA-2153937 (1996).

Abstract No. XP002227535 for Toldy, et al., Acta Chimica Academiae Scientiarum Hungarica., vol. 53, p. 279 (1967).

Abstract No. XP002227534 for Larkin, H., et al., Tetrahedron Letters, vol. 27, No. 24, pp. 2721-2724 (1986).

Abstract No. XP002227536 for Aicher, T., et al., Journal of Medicinal Chemistry, vol. 43, No. 2, pp. 236-249 (2000).

Hays S.J., et al., Journal of Medicinal Chemistry, American Chemical Society, Washington, US, vol. 33, No. 10 pp. 2916-2924 (1990).

Kawamoto, et al., Chemical Abstract vol. 118, No. 233765 (1993).

Papageorgiou, et. al., Organic letters, vol. 2, pp. 1049-1051 (Mar. 2000).

* cited by examiner

PIPERAZINE DERIVATIVES

PRIORITY TO RELATED APPLICATIONS

This application is a Continuation of Ser. No. 10/010,058, filed Dec. 7, 2001 (abandoned).

BACKGROUND

It has been recognized that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996).

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25–30 $kg/m^2$. Obesity is a BMI greater than 30 $kg/M^2$. There are problems with this definition in that it does not take into account the proportion of body mass that is muscle in relation to fat (adipose tissue). To account for this, obesity can also be defined on the basis of body fat content: greater than 25% in males and greater than 30% in females.

As the BMI increases there is an increased risk of death from a variety of causes that is independent of other risk factors. The most common diseases associated with obesity are cardiovascular disease (particularly hypertension), diabetes (obesity aggravates the development of diabetes), gall bladder disease (particularly cancer) and reproductive diseases. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline re-uptake inhibitor) can increase blood pressure and heart rate in some patients. The serotonin releaser/re-uptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective $5\text{-}HT_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, Psychopharmacol., 1988, 96, 93–100; G. A. Kennett, C. T. Dourish and G. Curzon, Eur. J. Pharmacol., 1987, 141, 429–435) and to accelerate the appearance of the behavioural satiety sequence (S. J. Kitchener and C. T. Dourish, Psychopharmacol., 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., Psychopharmacol., 1994, 116, 120–122) and decreased the appetite and body weight of obese male and female subjects during subchronic treatment for a 14 day period (P. A. Sargeant et al., Psychopharmacol., 1997, 133, 309–312). The anorectic action of mCPP is absent in $5\text{-}HT_{2C}$ receptor knockout mutant mice (L. H. Tecott et al., Nature, 1995, 374, 542–546) and is antagonised by the $5\text{-}HT_{2C}$ receptor antagonist SB-242084 in rats (G. A. Kennett et al., Neuropharmacol., 1997, 36, 609–620). It seems therefore that mCPP decreases food intake via an agonist action at the $5\text{-}HT_{2C}$ receptor.

Other compounds which have been proposed as $5\text{-}HT_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to $5\text{-}HT_{2C}$ receptors and may be used in the treatment of obesity. WO-A-98/30548 discloses aminoalkylindazole compounds as $5\text{-}HT_{2C}$ agonists for the treatment of CNS diseases and appetite regulation disorders. WO 0035922 discloses 2,3,4,4a-tetrahydro-1H-pyrazino[1,2-a]quinoxalin-5(6H) ones as $5HT_{2C}$ agonists. Aralkyloxycarbonyl-substituted piperazine derivatives have been repeatedly described as nitrogen-protected piperazine synthetic intermediates (e.g. Org. Lett., 2000, 2(8), 1049–1051.

SUMMARY

The present invention is a new piperazine derivative, processes and intermediates for its preparation, to pharmaceutical compositions containing the compound of the invention and to a method of treatment using the compound. The active compound of the present invention is useful in treating obesity and other disorders.

The invention is a compound of formula I or a pharmaceutically acceptable salt, solvate or ester therof (I)

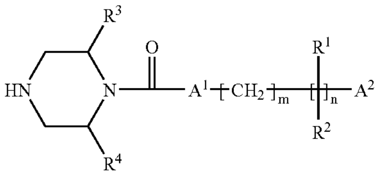

wherein $R^1$ and $R^2$ are independently selected from hydrogen, alkyl, cycloalkyl, aryl and aralkyl or $R^1$ and $R^2$ together with the carbon atom to which they are attached form an unsubstituted 3- to 8-membered carbocyclic ring or a 3- to 8-membered ring which is substituted with alkyl;

$R^3$ and $R^4$ are independently selected from hydrogen, alkyl, cycloalkyl, aryl and aralkyl;

$A^1$ is oxygen or sulfur, wherein in case $A^1$ is oxygen and $A^2$ is unsubstituted phenyl one of $R^1$, $R^2$, $R^3$ and $R^4$ is not hydrogen $A^2$ is unsubstituted aryl, unsubstituted heteroaryl or unsubstituted cycloalkyl or aryl, heteroaryl or cycloalkyl each substituted with at least one substituent independently selected from the group consisting of halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, or wherein said alkyl, said cycloalkyl, said aryl, said aralkyl, said alkoxy, said aralkoxy, said aryloxy, said alkoxycarbonyl, said cycloalkoxycarbonyl, said aryloxycarbonyl, said aralkoxycarbonyl, said heteroaryloxycarbonyl, said cycloalkoxy, said alkylsulfonyloxy, said arylsulfonyloxy, said heteroarylalkoxy, said alkenyloxy, said tetrahydrofuranylalkoxy, said alkynyloxy and said cycloalkylalkoxy are substituted with between one and three substituents independently selected from the group consisting of alkyl, alkoxy, halogen, nitro, oxo, trifluoromethyl, alkoxy substituted with between one and three halogen, thiophenyl, aryl, amino, alkylcarbonyl and aryloxy, or two substituents of aryl, heteroaryl or cycloalkyl form, together with the carbon atoms to which they are attached, an unsubstituted 5- to 7-membered carbocyclic ring or a substituted 5- to 7-membered carbocyclic ring with at least one substituent independently selected from the group consisting of alkyl, alkoxy and halogen;

n is 1 or 2;

m is zero or 1;

wherein 2-methyl-1-piperazinecarboxylic acid (4-nitrophenyl)methyl ester and 1-piperazinecarboxylic acid (4-(trifluoromethyl)phenyl)methyl ester are excluded.

It is an object of this invention to provide selective, directly acting $5HT_2$ receptor ligands for use in therapy and particularly for use as anti-obesity agents. It is a further object of this invention to provide directly acting ligands selective for $5\text{-}HT_{2C}$ receptors, for use in therapy and particularly for use as anti-obesity agents. It is a further object of this invention to provide selective, directly acting $5\text{-}HT_{2C}$ receptor ligands, preferably $5\text{-}HT_{2C}$ receptor agonists, for use in therapy and particularly for use as anti-obesity agents.

DETAILED DESCRIPTION

The term “alkyl”, alone or in combination, signifies a straight-chain or branched-chain alkyl group with 1 to 10, preferably 1 to 8 carbon atoms, more preferably a straight or branched-chain alkyl group with 1–4 carbon atoms. Examples of straight-chain and branched $C_1$–$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl and isopropyl. Particularly preferred are methyl and ethyl.

The term “cycloalkyl”, alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethylcyclohexyl, cycloheptyl and cyclooctyl, preferably cyclopropyl and particularly cyclopentyl.

The term “alkoxy”, alone or in combination, signifies a group of the formula alkyl-O— in which the term “alkyl” has the previously given significance, such as methoxy, ethoxy, n-propoxy, isopropoxy, n-butoxy, isobutoxy, sec.butoxy and tert.butoxy, preferably methoxy and ethoxy.

The term “cycloalkoxy”, alone or in combination, signifies a group of the formula cycloalkyl-O— in which the term “cycloalkyl” has the previously given significance, such as cyclohexyloxy.

The term “carbonyl” refer to a group of the formula —C(O)—.

The term “aryl”, alone or in combination, signifies a phenyl or naphthyl group, preferably a phenyl group which optionally carries one or more, preferably one to three substituents each independently selected from halogen, trifluoromethyl, amino, alkyl, aryloxy, alkylcarbonyl, cyano, carbamoyl, alkoxycarbamoyl, methylendioxy, carboxy, alkoxycarbonyl, hydroxycarbonyl, aminocarbonyl, alkyaminocarbonyl, dialkylaminocarbonyl, hydroxy, nitro and alkoxy, wherein alkoxy is optionally substituted with 1 to 3 halogen atoms. Preferred is phenyl.

The term “aryloxy”, alone or in combination, signifies a group of the formula aryl-O— in which the term “aryl” has the previously given significance. Phenyloxy is an example of such an aryloxy group.

The term “heteroaryl”, alone or in combination, signifies an aromatic 5 to 10, preferably 5- or 6-membered ring comprising 1 to 3 atoms independently selected from nitrogen, oxygen or sulfur such as e.g. furyl, pyridyl, 1,2-, 1,3- and 1,4-diazinyl, thienyl, isoxazolyl, oxazolyl, pyrrolyl and benzothiadiazolyl. Preferred examples are pyridyl, thienyl, pyrazinyl, furyl, isoxazole, (1,2,4)oxadiazole and thiazolyl. Particularly preferred are pyridyl and thienyl.

The term “heteroarylalkoxy”, alone or in combination, signifies an alkoxy group as defined before, wherein one or two, preferably one hydrogen atom is replaced by a heteroaryl group as defined before. Examples are pyridin-3-ylmethoxy, isoxazol-4-ylmethoxy, (1,2,4)oxadiazol-3-ylmethoxy, 3-furylmethoxy, thien-3-ylmethoxy, isoxazol-3-ylmethoxy, thien-2-methoxy, (2, 1, 3)benzothiadiazolylmethoxy, 2-thiophen-2-yl-ethoxy, 2-pyrrol-1-yl-ethoxy and thiazol-4-ylmethoxy.

The term “aralkyl”, alone or in combination, signifies an alkyl or cycloalkyl group as previously defined in which one or several, preferably one hydrogen atom has been replaced by an aryl group as previously defined. Preferred is benzyl.

The term “3- to 8-membered carbocyclic ring ”as used for the definition of $R^1$ and $R^2$ signifies a 3- to 8-membered, preferably 3 to 6 membered cycloalkane ring. Examples are cyclopropane, cyclobutane, cyclopentane, cyclohexane, cycloheptane and cyclooctane, preferably cyclopropane.

The term “5- to 7-membered carbocyclic ring ”as used for the definition of $A^2$ signifies a cycloalkane ring with 5 to 7, preferably 6 carbon atoms optionally substituted with alkyl, alkoxy or halogen. Examples are cyclopentane, methylcyclopentane, cyclohexane, methylcyclohexane, dimethylcyclohexane and cycloheptane preferably cyclohexane.

The term “aralkoxy”, alone or in combination, signifies an alkoxy or cycloalkoxy group as previously defined in which one or several, preferably one hydrogen atom has been replaced by an aryl group as previously defined. Preferred is benzyloxy.

The term “nitro”, alone or in combination, signifies a $—NO_2$ group.

The term “cyano”, alone or in combination, signifies a —CN group.

The term “alkoxycarbonyl”, alone or in combination, signifies an alkoxy-C(O)— group, wherein alkoxy is defined as before.

The term “cycloalkoxycarbonyl”, alone or in combination, signifies an cycloalkoxy-C(O)— group, wherein cycloalkoxy is defined as before.

The term “aryloxycarbonyl”, alone or in combination, signifies an aryloxy-C(O)— group, wherein aryloxy is defined as before.

The term “aralkoxycarbonyl”, alone or in combination, signifies an aralkoxy-C(O)— group, wherein aralkoxy is defined as before.

The term “heteroaryloxycarbonyl”, alone or in combination, signifies a heteroaryl-O—C(O)— group, wherein heteroaryl is defined as before.

The term “amino”, alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably amino, dimethylamino and diethylamino and particularly primary amino.

The term “halogen” signifies fluorine, chlorine, bromine or iodine and preferably fluorine, chlorine or bromine and particularly fluorine and chlorine.

The term “carbamoyl” alone or in combination refers to a group of the formula NH(R')—C(O)—, wherein R' means hydrogen, alkyl, cycloalkyl, aryl, aralkyl, heteroaryl, adamantyl, alkenyl or alkyl substituted with halogen. Preferably R' means alkyl or aralkyl particularly preferred are isopropyl, benzyl and tert. butyl.

The term “carbamoyloxy”, alone or in combination, signifies a carbamoyl-O— group, wherein carbamoyl is defined as before.

The term “alkylsulfonyloxy”, alone or in combination, signifies a

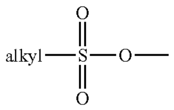

group in which alkyl is as previously defined. An examples is propylsulfonyloxy.

The term “arylsulfonyloxy”, alone or in combination, signifies a

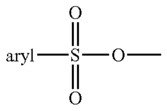

group in which aryl is as previously defined. An examples is phenylsulfonyloxy.

The term “alkenyl”, alone or in combination, signifies a straight-chain or branched-chain hydrocarbon group comprising an carbon-carbon double bond and 1 to 10, preferably 1 to 8 carbon atoms, more preferably 1–4 carbon atoms.

The term “alkenyloxy”, alone or in combination, signifies an alkenyl-O— group, wherein alkenyl is defined as before.

The term “alkynyl”, alone or in combination, signifies a straight-chain or branched-chain hydrocarbon group comprising an carbon-carbon triple bond and 1 to 10, preferably 1 to 8 carbon atoms, more preferably 1–4 carbon atoms.

The term “alkynyloxy”, alone or in combination, signifies an alkynyl-O— group, wherein alkynyl is defined as before.

The term “oxo”, alone or in combination, signifies an ═O group.

Examples of pharmaceutically acceptable salts of the compounds of formula I are salts with physiologically compatible mineral acids such hydrochloric acid, sulfuric acid or phosphoric acid; or with organic acids such as methanesulphonic acid, acetic acid, trifluoroacetic acid, citric acid, fumaric acid, maleic acid, tartaric acid, succinic acid or salicylic acid. Preferred salts of compounds of formula I are hydrochloride salts, succinate salts and fumarate salts. The compounds of formula I can also form salts with physiologically compatible bases. Examples of such salts are alkali metal, alkali earth metal, ammonium and alkylammonium salts such as the Na, K, Ca or tetramethylammonium salt. The compound of formula I can also be present in the form of zwitterions.

The invention expressly includes pharmaceutically acceptable derivatives of the compounds of formula I. For example hydroxy groups of compounds of formula I can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

Also included are pharmaceutically acceptable solvates of compounds according to formula I such as for example hydrates. The solvation can be effected in the course of the manufacturing process or can take place e.g. as a consequence of hygroscopic properties of an initially anhydrous compound of formula I (hydration).

The term “lipase inhibitor” refers to compounds that are capable of inhibiting the action of lipases, for example gastric and pancreatic lipases. For example, orlistat and lipstatin as described in U.S. Pat. No. 4,598,089 are potent inhibitors of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term “lipase inhibitor” refers also to polymer bound lipase inhibitors for example described in International Patent Application WO99/34786 (Geltex Pharmaceuticals Inc.). These polymers are characterised in that they have been substituted with one or more groups that inhibit lipases. The term “lipase inhibitor” also comprises pharmaceutically acceptable salts of these compounds. The term “lipase inhibitor” preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluent).

The term "asymmetric carbon atom (C*) means a carbon atom with four different substituents. According to the Cahn-Ingold-Prelog-Convention the asymmetric carbon atom can be of the "R" or "S" configuration.

Preferred are compounds according to formula I, wherein $R^1$ and $R^2$ are independently selected from hydrogen, alkyl, cycloalkyl, aryl and aralkyl or $R^1$ and $R^2$ together with the carbon atom to which they are attached form a 3- to 8-membered carbocyclic ring which is optionally substituted with alkyl;

$R^3$ and $R^4$ are independently selected from hydrogen, alkyl, cycloalkyl, aryl and aralkyl;

$A^1$ is oxygen or sulfur, wherein in case $A^1$ is oxygen and $A^2$ is unsubstituted phenyl, one of $R^1$, $R^2$, $R^3$ and $R^4$ is not hydrogen;

$A^2$ is aryl, heteroaryl or cycloalkyl each optionally substituted with one or more substituents independently selected from halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl and carbamoyl, wherein alkyl, cycloalkyl, aryl, aralkyl, alkoxy, aralkoxy, aryloxy, alkoxycarbonyl, cycloalkoxycarbonyl, aryloxycarbonyl, aralkoxycarbonyl and heteroaryloxycarbonyl are optionally substituted with one to three substituents independently selected from alkyl, alkoxy, halogen and nitro, or two substituents of aryl, heteroaryl or cycloalkyl form together with the carbon atoms to which they are attached a 5- to 7-membered carbocyclic ring which is optionally substituted with alkyl, alkoxy or halogen;

n is 1 or 2 and m is zero.

More preferred compounds according to formula I are those wherein $R^3$ and $R^4$ are independently selected from hydrogen and alkyl, most preferably $R^3$ and $R^4$ are hydrogen.

In another preferred embodiment, $R^3$ and $R^4$ are both alkyl. Additional preferred compounds are those wherein $R^3$ and $R^4$ are methyl. Most preferred are the compounds according to formula I, wherein $R^3$ and $R^4$ are methyl and both methyl groups have the cis configuration. Preferred are the cis-2,6-dimethylpiperazine derivatives of the formula I, wherein $R^3$ and $R^4$ are methyl and $R^1$, $R^2$, $A^1$, $A^2$, m and n are defined as mentioned before.

A further preferred embodiment of the invention are compounds according to formula I, wherein one of $R^3$ and $R^4$ is methyl or ethyl and the other one is hydrogen.

Particularly preferred are chiral compounds of formula (Ia), (Ia)

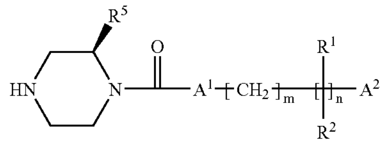

wherein $R^5$ is alkyl, particularly methyl or ethyl, and $R^1$, $R^2$, $A^1$, $A^2$, m and n are defined as before. Formula Ia means that the asymmetric carbon atom C*

(Ia)

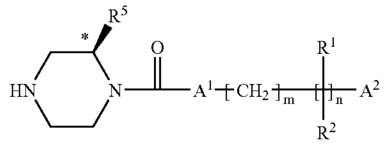

is of the R configuration.

Further preferred compounds of formula I are those, wherein $A^1$ is sulfur. Most preferred compounds of formula I are those wherein $A^1$ is oxygen.

Also preferred compounds of formula I are those wherein $R^1$ and $R^2$ are independently selected from hydrogen, alkyl, cycloalkyl, aryl and aralkyl or $R^1$ and $R^2$ together with the carbon atom to which they are attached form a 3- to 8-membered cycloalkyl ring which is optionally substituted with alkyl. A particularly preferred embodiment of the invention comprises compounds of formula I, wherein $R^1$ and $R^2$ are independently selected from hydrogen, alkyl and aryl, preferably hydrogen, methyl and phenyl. Most preferred are those compounds, wherein $R^1$ and $R^2$ are both hydrogen.

Preferred are compounds according to formula (I), wherein $A^2$ is aryl, heteroaryl or cycloalkyl each optionally substituted with one or more, preferably one to four, particularly preferred one to three substituents independently selected from halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, wherein alkyl, cycloalkyl, aryl, aralkyl, alkoxy, aralkoxy, aryloxy, alkoxycarbonyl, cycloalkoxycarbonyl, aryloxycarbonyl, aralkoxycarbonyl, heteroaryloxycarbonyl, cycloalkoxy, alkylsulfonyloxy, arylsulfonyloxy, heteroarylalkoxy, alkenyloxy, tetrahydrofuranylalkoxy, alkynyloxy and cycloalkylalkoxy are optionally substituted with one to three substituents independently selected from alkyl, alkoxy, halogen, nitro, oxo, trifluoromethyl, alkoxy substituted with one to three halogen, thiophenyl, aryl, amino, alkylcarbonyl and aryloxy, or two substituents of aryl, heteroaryl or cycloalkyl form together with the carbon atoms to which they are attached a 5- to 7-membered carbocyclic ring which is optionally substituted with one or more, preferably one to three substituents independently selected from alkyl, alkoxy and halogen.

Likewise preferred are compounds of the present invention, wherein $A^2$ is phenyl, naphthalenyl, cycloalkyl, pyridyl, thienyl, pyrazinyl or furyl, each optionally substituted with one or more, preferably one to four substituents, independently selected from halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl and carbamoyl, wherein alkyl, cycloalkyl, aryl, aralkyl, alkoxy, aralkoxy, aryloxy, alkoxycarbonyl, cycloalkoxycarbonyl, aryloxycarbonyl, aralkoxycarbonyl and heteroaryloxycarbonyl are optionally substituted with one to three substituents independently selected from alkyl, alkoxy, halogen and nitro, or two substituents of aryl, heteroaryl or cycloalkyl form together with the carbon atoms to which they are attached a 5- to 7-membered carbocyclic ring which is optionally substituted with alkyl, alkoxy or halogen.

Preferred are compounds according to formula I, wherein $A^2$ is phenyl, naphthalenyl, cyclohexyl, pyridyl or thienyl each optionally substituted with one or more, preferably one to four substituents independently selected from halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl and carbamoyl, wherein alkyl, cycloalkyl, aryl, aralkyl, alkoxy, aralkoxy, aryloxy, alkoxycarbonyl, cycloalkoxycarbonyl, aryloxycarbonyl, aralkoxycarbonyl and heteroaryloxycarbonyl are optionally substituted with one to three substituents independently selected from alkyl, alkoxy, halogen and nitro. Particularly preferred examples of the above substituents of phenyl, naphthalenyl, cyclohexyl, pyridyl and thienyl are trifluoromethoxyl, fluoro, chloro, bromo, nitro, phenylmethoxy, trifluoromethyl, methyl, tert-butyl, difluoromethoxy, cyano, methoxycarbonyl, benzyloxy, fluoro-benzyloxy, chlorobenzyloxy and nitrobenzyloxy.

Particularly preferred are compounds of formula I are those, wherein $A^2$ is phenyl, naphthalenyl, cyclohexyl, pyridyl or thienyl each optionally substituted with one or more, preferably one to four substituents independently selected from halogen, alkyl, aryl, alkoxy, aralkoxy, cyano, nitro, alkoxycarbonyl, wherein alkyl, alkoxy, aralkoxy and alkoxycarbonyl are optionally substituted with one to three substituents independently selected from halogen and nitro.

Other preferred compounds of formula I are those wherein $A^2$ is phenyl, optionally substituted with one to five, preferably one to three substituents independently selected from halogen, alkyl, aryl, alkoxy, aralkoxy, cyano, nitro, alkoxycarbonyl, wherein alkyl, alkoxy and aralkoxy optionally substituted with one to three substituents independently selected from halogen and nitro.

A further preferred object of the present invention are compounds according to formula I, wherein n is 1.

Another preferred object of the present invention are compounds according to formula I, wherein $A^2$ is phenyl, optionally substituted with one to four substituents independently selected from halogen, alkoxy, carbamoyloxy, heteroarylalkoxy, alkenyloxy, alkynyloxy and cycloalkylalkoxy, wherein alkoxy, heteroarylalkoxy and alkenyloxy are optionally substituted with one to three substituents independently selected from alkyl and halogen. Particularly, preferred are compounds of formula I, wherein $A^2$ is phenyl, optionally substituted with one to three substituents independently selected from fluoro, chloro, difluoromethoxy, propoxy, 3,5-dimethyl-isoxazol-4-ylmethoxy, 2-propenyloxy, 5-pentyloxy, cyclopropylmethoxy, 2-propynyloxy and NH(R')—C(O)—O—, wherein R' is isopropyl, benzyl or tert.-butyl.

Additionally preferred compounds of formula I are those wherein m is zero.

Examples of preferred compounds of formula I include:

Piperazine-1-carboxylic acid 4-trifluoromethoxy-benzyl ester;
piperazine-1-carboxylic acid 3,4-difluoro-benzyl ester;
piperazine-1-carboxylic acid 4-fluoro-benzyl ester;
piperazine-1-carboxylic acid 4-bromo-benzyl ester;
piperazine-1-carboxylic acid 2-trifluoromethoxy-benzyl ester;
piperazine-1-carboxylic acid 2-chloro-5-nitro-benzyl ester;
piperazine-1-carboxylic acid 2-chloro-benzyl ester;
piperazine-1-carboxylic acid biphenyl-4-ylmethyl ester;
piperazine-1-carboxylic acid 3-methoxy-benzyl ester;
piperazine-1-carboxylic acid 3-trifluoromethyl-benzyl ester;
piperazine-1-carboxylic acid 4-trifluoromethyl-benzyl ester;
piperazine-1-carboxylic acid naphthalen-2-ylmethyl ester;
piperazine-1-carboxylic acid naphthalen-1-ylmethyl ester;
piperazine-1-carboxylic acid 2-methyl-benzyl ester;
piperazine-1-carboxylic acid 2,4-dichloro-benzyl ester;
piperazine-1-carboxylic acid 2,6-dichloro-benzyl ester;
piperazine-1-carboxylic acid 4-tert-butyl-benzyl ester;
piperazine-1-carboxylic acid 2-fluoro-4-trifluoromethyl-benzyl ester;
piperazine-1-carboxylic acid 2,4-difluoro-benzyl ester;
piperazine-1-carboxylic acid 2-chloro-4-fluoro-benzyl ester;
piperazine-1-carboxylic acid 4-fluoro-2-trifluoromethyl-benzyl ester;
piperazine-1-carboxylic acid 4-difluoromethoxy-benzyl ester;
piperazine-1-carboxylic acid 2,4-dimethyl-benzyl ester;
piperazine-1-carboxylic acid cyclohexylmethyl ester;
piperazine-1-carboxylic acid 2-fluoro-benzyl ester;
cis-2,6-dimethyl-piperazine-1-carboxylic acid 4-chloro-benzyl ester;
cis-2,6-dimethyl-piperazine-1-carboxylic acid 3-cyano-benzyl ester;
cis-2,6-dimethyl-piperazine-1-carboxylic acid 4-methoxy-carbonyl-benzyl ester;
piperazine-1-carboxylic acid 4-cyano-benzyl ester;
piperazine-1-carboxylic acid 2-trifluoromethyl-benzyl ester;
piperazine-1-carboxylic acid 4-chloro-2-fluoro-benzyl ester;
piperazine-1-carbothioic acid S-(4-benzyloxy-benzyl) ester;
piperazine-1-carbothioic acid S-(4-bromo-benzyl) ester;
piperazine-1-carbothioic acid S-(4-trifluoromethoxy-benzyl) ester;
piperazine-1-carbothioic acid S-(4-fluoro-benzyl) ester;
piperazine-1-carbothioic acid S-(2,4-difluoro-benzyl) ester;
piperazine-1-carbothioic acid S-(4-methoxy-benzyl) ester;
piperazine-1-carbothioic acid S-(2,4-dimethyl-benzyl) ester;

piperazine-1-carbothioic acid S-(2-fluoro-4-trifluoromethyl-benzyl) ester;
piperazine-1-carbothioic acid S-[4-(4-fluoro-benzyloxy)-benzyl] ester;
piperazine-1-carboxylic acid 4-benzyloxy-benzyl ester;
piperazine-1-carboxylic acid 4-(4-fluoro-benzyloxy)-benzyl ester;
piperazine-1-carboxylic acid 4-methoxy-benzyl ester;
piperazine-1-carboxylic acid benzhydryl ester;
(RS)-piperazine-1-carboxylic acid 1-phenyl-ethyl ester;
piperazine-1-carboxylic acid phenethyl ester;
cis-2,6-dimethylpiperazine-1-carboxylic acid 5-[2-(3-chlorobenzyloxy)]pyridyl-methyl ester;
piperazine-1-carboxylic acid 5-[2-(3-chlorobenzyloxy)]pyridyl-methyl ester;
cis-2,6-dimethylpiperazine-1-carboxylic acid 2-(2-thienyl) ethyl ester;
cis-2,6-dimethylpiperazine-1-carboxylic acid 2-fluoro-benzyl ester;
piperazine-1-carbothioic acid S-[4-(3-nitrobenzyl)oxy]benzyl ester;
piperazine-1-carboxylic acid 3-(2-phenethyloxy)-benzyl ester
3-[2-(3-chlorophenyl)]ethoxybenzyl piperazine-1-carboxylate;
cis-2,6-dimethyl-piperazine-1-carboxylic acid 6-(2-fluoro-benzyloxy)-pyridin-3-ylmethyl ester;
4-bromo-2-fluorobenzyl cis-2,6-dimethylpiperazine-1-carboxylate;
benzyl cis-2,6-dimethylpiperazine-1-carboxylate;
2-chlorobenzyl cis-2,6-dimethylpiperazine-1-carboxylate;
(R)-2-fluorobenzyl 2-methylpiperazine-1-carboxylate;
2-fluoro-4-propylbenzyl cis-2,6-dimethylpiperazine-1-carboxylate;
S-4-[(ethylamino)carbonyl]oxybenzyl piperazine-1-thiocarboxylate;
S-4-[[(2-chloroethyl)amino]carbonyl]oxybenzyl piperazine-1-thiocarboxylate;
S-4-[(butylamino)carbonyl]oxybenzyl piperazine-1-thiocarboxylate;
S-4-[(2-propylamino)carbonyl]oxybenzyl piperazine-1-thiocarboxylate;
S-4-[(benzylamino)carbonyl]oxybenzyl piperazine-1-thiocarboxylate;
S-4-[[(2-methylbenzyl)amino]carbonyl]oxybenzyl piperazine-1-thiocarboxylate;
4-difluoromethoxybenzyl cis-2,6-dimethylpiperazine-1-carboxylate;
cis-2,6-dimethyl-piperazine-1-carboxylic acid 6-(3-methyl-butoxy)-pyridin-3-ylmethyl ester;
cis-2,6-dimethyl-piperazine-1-carboxylic acid 6-(3-methyl-butoxy)-pyridin-3-ylmethyl ester;
4-ethyl-2-fluorobenzyl cis-2,6-dimethylpiperazine-1-carboxylate;
2-fluoro-4-pentylbenzyl cis-2,6-dimethylpiperazine-1-carboxylate;
S-4-[(tert-butylamino)carbonyl]oxybenzyl piperazine-1-thiocarboxylate;
2,5-difluorobenzyl cis-2,6-dimethylpiperazine-1-carboxylate;
2,3-difluorobenzyl cis-2,6-dimethylpiperazine-1-carboxylate;
2,6-difluorobenzyl cis-2,6-dimethylpiperazine-1-carboxylate;
2,4-dimethylbenzyl cis-2,6-dimethylpiperazine-1-carboxylate;
S-4-[(propylamino)carbonyl]oxybenzyl piperazine-1-thiocarboxylate;
S-4-[(cyclohexylamino)carbonyl]oxybenzyl piperazine-1-thiocarboxylate;
2-fluoro-4-difluoromethoxybenzyl cis-2,6-dimethylpiperazine-1-carboxylate;
3-benzyloxybenzyl cis-2,6-dimethylpiperazine-1-carboxylate;
2,6-difluoro-4-difluoromethoxybenzyl cis-2,6-dimethylpiperazine-1-carboxylate;
(+/−)-S-4-[(2-butylamino)carbonyl]oxybenzyl piperazine-1-thiocarboxylate;
S-4-[(cyclopentylamino)carbonyl]oxybenzyl piperazine-1-thiocarboxylate;
S-4-[(1-adamantylamino)carbonyl]oxybenzyl piperazine-1-thiocarboxylate;
S-4-[(2-propenylamino)carbonyl]oxybenzyl piperazine-1-thiocarboxylate;
S-4-[(phenylamino)carbonyl]oxybenzyl piperazine-1-thiocarboxylate;
S-4-[[4-(2-propylphenyl)amino]carbonyl]oxybenzyl piperazine-1-thiocarboxylate;
(+/−)-S-4-[[(1-phenylethyl)amino]carbonyl]oxybenzyl piperazine-1-thiocarboxylate;
S-4-[[[(4-ethoxycarbonyl)phenyl]amino]carbonyl]oxybenzylpiperazine-1-thiocarboxylate;
S-4-[[(3-chloro-4-fluorophenyl)amino]carbonyl]oxybenzyl piperazine-1-thiocarboxylate;
S-4-[[(4-difluoromethoxyphenyl)amino]carbonyl]oxybenzylpiperazine-1-thiocarboxylate;
4-methylbenzyl cis-2,6-dimethylpiperazine-1-carboxylate;
(+/−)-4-difluoromethoxybenzyl 2-ethylpiperazine-1-carboxylate;
S-4-[[(4-methoxyphenyl)amino]carbonyl]oxybenzyl piperazine-1-thiocarboxylate;
S-4-[[(3-methylbenzyl)amino]carbonyl]oxybenzyl piperazine-1-thiocarboxylate;
S-4-[[(4-methoxybenzyl)amino]carbonyl]oxybenzyl piperazine-1-thiocarboxylate;
2,6-difluoro-4-(2-propyl)oxybenzyl cis-2,6-dimethylpiperazine-1-carboxylate;
S-4-(2-oxo-2-phenylethoxy)benzyl piperazine-1-thiocarboxylate;
(R)-4-difluoromethoxybenzyl 2-ethylpiperazine-1-carboxylate;
S-4-benzenesulfonyloxybenzyl piperazine-1-thiocarboxylate;
(+/−)-2,6-difluoro-4-propoxybenzyl 2-ethylpiperazine-1-carboxylate;
(+/−)-2,6-difluoro-4-difluoromethoxybenzyl 2-ethylpiperazine-1-carboxylate;
2-fluoro-5-methoxybenzyl cis-2,6-dimethylpiperazine-1-carboxylate;
3-difluoromethoxybenzyl cis-2,6-dimethylpiperazine-1-carboxylate;
S-4-propanesulfonyloxybenzyl piperazine-1-thiocarboxylate;
cis-2,6-dimethyl-piperazine-1-carboxylic acid 2,6-difluoro-4-(pyridin-3-ylmethoxy)-benzyl ester;
(R)-2,6-difluoro-4-propoxybenzyl 2-methylpiperazine-1-carboxylate;
(R)-4-difluoromethoxybenzyl 2-methylpiperazine-1-carboxylate;
5-benzyloxy-2-fluorobenzyl cis-2,6-dimethylpiperazine-1-carboxylate;
2,6-difluoro-4-(3-phenyl)propoxybenzyl cis-2,6-dimethylpiperazine-1-carboxylate;

4-bromo-2-fluorobenzyl piperazine-1-carboxylate;

2,6-difluoro-4-(2-propenyl)oxybenzyl cis-2,6-dimethylpiperazine-1-carboxylate;

(R)-2,6-difluoro-4-difluoromethoxybenzyl 2-methylpiperazine-1-carboxylate;

2-fluoro-5-difluoromethoxybenzyl cis-2,6-dimethylpiperazine-1-carboxylate;

5-ethoxy-2-fluorobenzyl cis-2,6-dimethylpiperazine-1-carboxylate;

2-fluoro-5-propoxybenzyl piperazine-1-carboxylate;

(R)-2-fluoro-5-propoxybenzyl 2-methylpiperazine-1-carboxylate;

2-fluoro-5-propoxybenzyl cis-2,6-dimethylpiperazine-1-carboxylate;

5-butoxy-2-fluorobenzyl piperazine-1-carboxylate;

(R)-5-butoxy-2-fluorobenzyl 2-methylpiperazine-1-carboxylate;

5-butoxy-2-fluorobenzyl cis-2,6-dimethylpiperazine-1-carboxylate;

cis-2,6-dimethyl-piperazine-1-carboxylic acid 4-(3,5-dimethyl-isoxazol-4-ylmethoxy)-2,6-difluoro-benzyl ester;

2-fluoro-5-(2-methylpropyl)-oxybenzyl cis-2,6-dimethylpiperazine-1-carboxylate;

2-chloro-6-fluorobenzyl cis-2,6-dimethylpiperazine-1-carboxylate;

(R)-2,6-difluorobenzyl 2-methylpiperazine-1-carboxylate;

(R,R)-4-difluoromethoxybenzyl 2,6-dimethylpiperazine-1-carboxylate;

(R)-2-fluoro-5-(2-propenyl)oxybenzyl 2-methylpiperazine-1-carboxylate;

2-fluoro-5-(2-propenyl)oxybenzyl cis-2,6-dimethylpiperazine-1-carboxylate;

5-(cyclohexylmethyl)oxy-2-fluorobenzyl cis-2,6-dimethylpiperazine-1-carboxylate;

2-fluoro-5-(2-phenyl)ethoxybenzyl cis-2,6-dimethylpiperazine-1-carboxylate;

2-fluoro-5-(3-phenyl)propoxybenzyl piperazine-1-carboxylate;

(R)-2-fluoro-5-(3-phenyl)propoxybenzyl 2-methylpiperazine-1-carboxylate;

2-fluoro-5-(3-phenyl)propoxybenzyl cis-2,6-dimethylpiperazine-1-carboxylate;

2-fluoro-5-(3-trifluoromethylbenzyl)oxybenzyl cis-2,6-dimethylpiperazine-1-carboxylate;

2-fluoro-5-(2-pyridylmethyl)oxybenzyl cis-2,6-dimethylpiperazine-1-carboxylate;

2-fluoro-5-(3-pyridylmethyl)oxybenzyl cis-2,6-dimethylpiperazine-1-carboxylate;

(+/−)-2,6-difluoro-4-(2-pyridylmethyl)oxybenzyl 2-methylpiperazine-1-carboxylate;

(+/−)-2,6-difluoro-4-(3-pyridylmethyl)oxybenzyl 2-methylpiperazine-1-carboxylate;

(+/−)-2-methyl-piperazine-1-carboxylic acid 4-(3,5-dimethyl-isoxazol-4-ylmethoxy)-2,6-difluoro-benzyl ester;

5-tert-butylaminocarbonyloxy-2-fluorobenzyl cis-2,6-dimethylpiperazine-1-carboxylate;

2-fluoro-5-(4-difluoromethoxybenzyl)oxybenzyl cis-2,6-dimethylpiperazine-1-carboxylate;

piperazine-1-carboxylic acid 2,6-difluoro-4-(5-thiophen-2-yl-[1,2,4]oxadiazol-3-ylmethoxy)-benzyl ester;

(R)-2-methyl-piperazine-1-carboxylic acid 2,6-difluoro-4-(5-thiophen-2-yl-[1,2,4]oxadiazol-3-ylmethoxy)-benzyl ester;

cis-2,6-dimethyl-piperazine-1-carboxylic acid 2,6-difluoro-4-(5-thiophen-2-yl-[1,2,4]oxadiazol-3-ylmethoxy)-benzyl ester;

2,6-difluoro-4-(3-fluorobenzyl)oxybenzyl cis-2,6-dimethylpiperazine-1-carboxylate;

2,6-difluoro-4-(3,4-difluorobenzyl)oxybenzyl cis-2,6-dimethylpiperazine-1-carboxylate;

2-fluoro-5-(2,4-difluorobenzyl)oxybenzyl cis-2,6-dimethylpiperazine-1-carboxylate;

2-fluoro-5-(3,4-difluorobenzyl)oxybenzyl cis-2,6-dimethylpiperazine-1-carboxylate;

2,6-difluoro-4-(3-furylmethyl)oxybenzyl cis-2,6-dimethylpiperazine-1-carboxylate;

(+/−)-2,6-difluoro-4-(3-furylmethyl)oxybenzyl 2-ethylpiperazine-1-carboxylate;

(+/−)-piperazine-1-carboxylic acid 2,6-difluoro-4-(tetrahydro-furan-2-ylmethoxy)-benzyl ester;

(+/−)-piperazine-1-carboxylic acid 2-fluoro-4-(tetrahydro-furan-2-ylmethoxy)-benzyl ester;

2,6-difluoro-4-(3-thienylmethyl)oxybenzyl cis-2,6-dimethylpiperazine-1-carboxylate;

2,6-difluoro-4-(3-thienylmethyl)oxybenzyl piperazine-1-carboxylate;

(R)-2,6-difluoro-4-(3-thienylmethyl)oxybenzyl 2-methylpiperazine-1-carboxylate;

(+/−)-2,6-difluoro-4-(3-thienylmethyl)oxybenzyl 2-ethylpiperazine-1-carboxylate;

cis-2,6-dimethyl-piperazine-1-carboxylic acid 2,6-difluoro-4-(5-methyl-isoxazol-3-ylmethoxy)-benzyl ester;

cis-2,6-dimethyl-piperazine-1-carboxylic acid 2,6-difluoro-4-(5-methyl-3-phenyl-isoxazol-4-ylmethoxy)-benzyl ester;

(+/−)-2-fluoro-5-(2-propenyl)oxybenzyl 2-ethylpiperazine-1-carboxylate;

2-fluoro-5-(2-propenyl)oxybenzyl piperazine-1-carboxylate;

2,6-difluoro-4-(2-thienylmethyl)oxybenzyl piperazine-1-carboxylate;

(R)-2,6-difluoro-4-(2-thienylmethyl)oxybenzyl 2-methylpiperazine-1-carboxylate;

cis-2,6-dimethyl-piperazine-1-carboxylic acid 2,6-difluoro-4-(thiophen-2-ylmethoxy)-benzyl ester;

5-butylaminocarbonyloxy-2-fluorobenzyl cis-2,6-dimethylpiperazine-1-carboxylate;

2-fluoro-5-(2-propynyl)oxybenzyl cis-2,6-dimethylpiperazine-1-carboxylate;

5-(5-[2,1,3]benzothiadiazolylmethyl)oxy-2-fluorobenzyl cis-2,6-dimethylpiperazine-1-carboxylate;

2-fluoro-5-(3-fluorobenzyl)oxybenzyl cis-2,6-dimethylpiperazine-1-carboxylate;

(R)-2-fluoro-5-pentyloxybenzyl 2-methylpiperazine-1-carboxylate;

5-(cyclopropylmethyl)oxy-2-fluorobenzyl cis-2,6-dimethylpiperazine-1-carboxylate;

(R)-2-methyl-piperazine-1-carboxylic acid 2-fluoro-5-(2-thiophen-2-yl-ethoxy)-benzyl ester;

cis-2,6-dimethyl-piperazine-1-carboxylic acid 3-bromo-2,6-difluoro-benzyl ester;

cis-2,6-dimethyl-piperazine-1-carboxylic acid 2,4-difluoro-2'-methoxy-biphenyl-3-ylmethyl ester;

cis-2,6-dimethyl-piperazine-1-carboxylic acid 2,4-difluoro-3',4'-dimethoxy-biphenyl-3-ylmethyl ester;

cis-2,6-dimethyl-piperazine-1-carboxylic acid 2,4-difluoro-3'-hydroxy-4'-methoxy-biphenyl-3-ylmethyl ester;

cis-2,6-dimethyl-piperazine-1-carboxylic acid 3'-amino-2,4-difluoro-biphenyl-3-ylmethyl ester;

cis-2,6-dimethyl-piperazine-1-carboxylic acid 4'-acetyl-2,4-difluoro-biphenyl-3-ylmethyl ester;

cis-2,6-dimethyl-piperazine-1-carboxylic acid 3'-acetyl-2,4-difluoro-biphenyl-3-ylmethyl ester;

(R)-2-ethyl-piperazine-1-carboxylic acid 2,6-difluoro-3-methyl-benzyl ester;

(R)-2-ethyl-piperazine-1-carboxylic acid 2,6-difluoro-benzyl ester;

(R)-2-ethyl-piperazine-1-carboxylic acid 4-cyclopropylmethoxy-2,6-difluoro-benzyl ester;

(R)-2-ethyl-piperazine-1-carboxylic acid 2,6-difluoro-4-propoxy-benzyl ester;

(R)-2-ethyl-piperazine-1-carboxylic acid 4-allyloxy-2,6-difluoro-benzyl ester;

(R)-2-ethyl-piperazine-1-carboxylic acid 2,6-difluoro-4-prop-2-ynyloxy-benzyl ester;

(R)-2-ethyl-piperazine-1-carboxylic acid 4-butoxy-2,6-difluoro-benzyl ester;

(R)-2-ethyl-piperazine-1-carboxylic acid 2,6-difluoro-4-(2-methoxy-ethoxy)-benzyl ester;

(R)-2-ethyl-piperazine-1-carboxylic acid 4-ethoxy-2,6-difluoro-benzyl ester;

(R)-2-ethyl-piperazine-1-carboxylic acid 2,6-difluoro-4-(2-methyl-thiazol-4-ylmethoxy)-benzyl ester;

(R)-2-ethyl-piperazine-1-carboxylic acid 2-fluoro-5-methoxy-benzyl ester;

(R)-2-ethyl-piperazine-1-carboxylic acid 5-ethoxy-2-fluoro-benzyl ester;

(R)-2-ethyl-piperazine-1-carboxylic acid 2-fluoro-5-propoxy-benzyl ester;

(R)-2-ethyl-piperazine-1-carboxylic acid 5-butoxy-2-fluoro-benzyl ester;

(R)-2-ethyl-piperazine-1-carboxylic acid 2-fluoro-5-pentyloxy-benzyl ester;

(R)-2-ethyl-piperazine-1-carboxylic acid 2-fluoro-5-(3-methyl-butoxy)-benzyl ester;

(R)-2-ethyl-piperazine-1-carboxylic acid 5-benzyloxy-2-fluoro-benzyl ester;

(R)-2-ethyl-piperazine-1-carboxylic acid 2-fluoro-5-phenethyloxy-benzyl ester;

(R)-2-ethyl-piperazine-1-carboxylic acid 2-fluoro-5-(2-methyl-benzyloxy)-benzyl ester;

(R)-2-ethyl-piperazine-1-carboxylic acid 2-fluoro-5-(3-methyl-benzyloxy)-benzyl ester;

(R)-2-ethyl-piperazine-1-carboxylic acid 2-fluoro-5-(2-pyrrol-1-yl-ethoxy)-benzyl ester;

(R)-2-ethyl-piperazine-1-carboxylic acid 5-cyclopropylmethoxy-2-fluoro-benzyl ester;

(R)-2-ethyl-piperazine-1-carboxylic acid 5-cyclobutylmethoxy-2-fluoro-benzyl ester;

(R)-2-ethyl-piperazine-1-carboxylic acid 5-cyclohexylmethoxy-2-fluoro-benzyl ester;

(R)-2-ethyl-piperazine-1-carboxylic acid 5-(2-cyclohexyl-ethoxy)-2-fluoro-benzyl ester;

(R)-2-ethyl-piperazine-1-carboxylic acid 2-fluoro-5-prop-2-ynyloxy-benzyl ester;

(R)-2-ethyl-piperazine-1-carboxylic acid 5-allyloxy-2-fluoro-benzyl ester;

(R)-2-ethyl-piperazine-1-carboxylic acid 2-fluoro-5-(2-methoxy-ethoxy)-benzyl ester;

(R)-2-ethyl-piperazine-1-carboxylic acid 5-(2-ethoxy-ethoxy)-2-fluoro-benzyl ester;

(R)-2-ethyl-piperazine-1-carboxylic acid 2-fluoro-5-(3-phenoxy-propoxy)-benzyl ester;

(R)-2-ethyl-piperazine-1-carboxylic acid 2,6-difluoro-3-methoxy-benzyl ester;

(R)-2-ethyl-piperazine-1-carboxylic acid 3-ethoxy-2,6-difluoro-benzyl ester;

(R)-2-ethyl-piperazine-1-carboxylic acid 2,6-difluoro-3-propoxy-benzyl ester;

(R)-2-ethyl-piperazine-1-carboxylic acid 3-butoxy-2,6-difluoro-benzyl ester;

(R)-2-ethyl-piperazine-1-carboxylic acid 2,6-difluoro-3-pentyloxy-benzyl ester;

(R)-2-ethyl-piperazine-1-carboxylic acid 2,6-difluoro-3-(3-methyl-butoxy)-benzyl ester;

(R)-2-ethyl-piperazine-1-carboxylic acid 3-benzyloxy-2,6-difluoro-benzyl ester;

(R)-2-ethyl-piperazine-1-carboxylic acid 2,6-difluoro-3-(3-phenyl-propoxy)-benzyl ester;

(R)-2-ethyl-piperazine-1-carboxylic acid 2,6-difluoro-3-(4-methyl-benzyloxy)-benzyl ester;

(R)-2-ethyl-piperazine-1-carboxylic acid 2,6-difluoro-3-(3-methyl-benzyloxy)-benzyl ester;

(R)-2-ethyl-piperazine-1-carboxylic acid 2,6-difluoro-3-(2-methyl-benzyloxy)-benzyl ester;

(R)-2-ethyl-piperazine-1-carboxylic acid 3-(3,3-dimethyl-butoxy)-2,6-difluoro-benzyl ester;

(R)-2-ethyl-piperazine-1-carboxylic acid 2,6-difluoro-3-(2-pyrrol-1-yl-ethoxy)-benzyl ester;

(R)-2-ethyl-piperazine-1-carboxylic acid 3-cyclopropylmethoxy-2,6-difluoro-benzyl ester;

(R)-2-ethyl-piperazine-1-carboxylic acid 3-cyclobutylmethoxy-2,6-difluoro-benzyl ester;

(R)-2-ethyl-piperazine-1-carboxylic acid 3-(2-cyclohexyl-ethoxy)-2,6-difluoro-benzyl ester;

(R)-2-ethyl-piperazine-1-carboxylic acid 2,6-difluoro-3-prop-2-ynyloxy-benzyl ester;

(R)-2-ethyl-piperazine-1-carboxylic acid 3-allyloxy-2,6-difluoro-benzyl ester;

(R)-2-ethyl-piperazine-1-carboxylic acid 2,6-difluoro-3-(2-methoxy-ethoxy)-benzyl ester;

(R)-2-ethyl-piperazine-1-carboxylic acid 3-(2-ethoxy-ethoxy)-2,6-difluoro-benzyl ester;

(R)-2-ethyl-piperazine-1-carboxylic acid 2,6-difluoro-3-(3-phenoxy-propoxy)-benzyl ester;

(R)-2-ethyl-piperazine-1-carboxylic 1-[2-fluoro-5-(3-methoxy-propoxy)-benzyl] ester;

(R)-2-ethyl-piperazine-1-carboxylic acid 1-[2,6-difluoro-3-(3-methoxy-propoxy)-benzyl]ester;

(R)-2-ethyl-piperazine-1-carboxylic acid 4-cyclopropylmethoxy-2-chloro-6-fluoro-benzyl ester;

(R)-2-ethyl-piperazine-1-carboxylic acid 2-chloro-6-fluoro-4-propoxy-benzyl ester;

(R)-2-ethyl-piperazine-1-carboxylic acid 2-chloro-6-fluoro-4-ethoxy-benzyl ester;

(R)-2-ethyl-piperazine-1-carboxylic acid 4-butoxy-2-chloro-6-fluoro-benzyl ester;

(R)-2-ethyl-piperazine-1-carboxylic acid 4-butoxy-2-chloro-6-fluoro-benzyl ester;

(R)-2-ethyl-piperazine-1-carboxylic acid 4-allyloxy-2-chloro-6-fluoro-benzyl ester;

(R)-2-ethyl-piperazine-1-carboxylic acid 2-chloro-6-fluoro-4-prop-2-ynyloxy-benzyl ester;

(R)-2-ethyl-piperazine-1-carboxylic acid 2-chloro-6-fluoro-4-(2-methoxy-ethoxy)-benzyl ester;

(R)-2-ethyl-piperazine-1-carboxylic acid 2-chloro-6-fluoro-4-(3-methoxy-propoxy)-benzyl ester;

(R)-2-Ethyl-piperazine-1-carboxylic acid 2-chloro-6-fluoro-4-(2-methyl-thiazol-4-ylmethoxy)-benzyl ester.

Examples of particularly preferred compounds of formula I are:

Piperazine-1-carboxylic acid 4-trifluoromethoxy-benzyl ester;

piperazine-1-carboxylic acid 2-chloro-benzyl ester;

piperazine-1-carboxylic acid 4-difluoromethoxy-benzyl ester;

piperazine-1-carboxylic acid 2-fluoro-benzyl ester;
cis-2,6-dimethyl-piperazine-1-carboxylic acid 4-chloro-benzyl ester;
piperazine-1-carbothioic acid S-(4-benzyloxy-benzyl) ester;
piperazine-1-carbothioic acid S-(2,4-difluoro-benzyl) ester;
piperazine-1-carbothioic acid S-(4-methoxy-benzyl) ester;
piperazine-1-carbothioic acid S-[4-(4-fluoro-benzyloxy)-benzyl] ester;
piperazine-1-carboxylic acid 4-(4-fluoro-benzyloxy)-benzyl ester;
cis-2,6-dimethylpiperazine-1-carboxylic acid 2-(2-thienyl) ethyl ester;
cis-2,6-dimethylpiperazine-1-carboxylic acid 2-fluoro-benzyl ester;
4-bromo-2-fluorobenzyl cis-2,6-dimethylpiperazine-1-carboxylate;
2-fluoro-4-propylbenzyl cis-2,6-dimethylpiperazine-1-carboxylate;
S-4-[(butylamino)carbonyl]oxybenzyl piperazine-1-thiocarboxylate;
S-4-[(2-propylamino)carbonyl]oxybenzyl piperazine-1-thiocarboxylate;
S-4-[(benzylamino)carbonyl]oxybenzyl piperazine-1-thiocarboxylate;
4-difluoromethoxybenzyl cis-2,6-dimethylpiperazine-1-carboxylate;
4-ethyl-2-fluorobenzyl cis-2,6-dimethylpiperazine-1-carboxylate;
S-4-[(tert-butylamino)carbonyl]oxybenzyl piperazine-1-thiocarboxylate;
2,6-difluorobenzyl cis-2,6-dimethylpiperazine-1-carboxylate;
2-fluoro-4-difluoromethoxybenzyl cis-2,6-dimethylpiperazine-1-carboxylate;
3-benzyloxybenzyl cis-2,6-dimethylpiperazine-1-carboxylate;
2,6-difluoro-4-difluoromethoxybenzyl cis-2,6-dimethylpiperazine-1-carboxylate;
(+/−)-4-difluoromethoxybenzyl 2-ethylpiperazine-1-carboxylate;
S-4-(2-oxo-2-phenylethoxy)benzyl piperazine-1-thiocarboxylate;
(R)-4-difluoromethoxybenzyl 2-ethylpiperazine-1-carboxylate;
(R)-2,6-difluoro-4-propoxybenzyl 2-methylpiperazine-1-carboxylate;
(R)-4-difluoromethoxybenzyl 2-methylpiperazine-1-carboxylate;
2-fluoro-5-propoxybenzyl cis-2,6-dimethylpiperazine-1-carboxylate;
cis-2,6-dimethyl-piperazine-1-carboxylic acid 4-(3,5-dimethyl-isoxazol-4-ylmethoxy)-2,6-difluoro-benzyl ester;
(R)-2-fluoro-5-(2-propenyl)oxybenzyl 2-methylpiperazine-1-carboxylate;
2-fluoro-5-(2-propenyl)oxybenzyl cis-2,6-dimethylpiperazine-1-carboxylate;
(R)-2-fluoro-5-pentyloxybenzyl 2-methylpiperazine-1-carboxylate;
5-(cyclopropylmethyl)oxy-2-fluorobenzyl cis-2,6-dimethylpiperazine-1-carboxylate;
(R)-2-ethyl-piperazine-1-carboxylic acid 4-cyclopropylmethoxy-2,6-difluoro-benzyl ester;
(R)-2-ethyl-piperazine-1-carboxylic acid 2,6-difluoro-4-propoxy-benzyl ester;
(R)-2-ethyl-piperazine-1-carboxylic acid 4-allyloxy-2,6-difluoro-benzyl ester;
(R)-2-ethyl-piperazine-1-carboxylic acid 2,6-difluoro-4-prop-2-ynyloxy-benzyl ester;
(R)-2-ethyl-piperazine-1-carboxylic acid 5-allyloxy-2-fluoro-benzyl ester;
(R)-2-ethyl-piperazine-1-carboxylic acid 3-allyloxy-2,6-difluoro-benzyl ester;
(R)-2-ethyl-piperazine-1-carboxylic acid 4-cyclopropylmethoxy-2-chloro-6-fluoro-benzyl ester;
(R)-2-ethyl-piperazine-1-carboxylic acid 2-chloro-6-fluoro-4-propoxy-benzyl ester;
(R)-2-ethyl-piperazine-1-carboxylic acid 4-allyloxy-2-chloro-6-fluoro-benzyl ester;
(R)-2-ethyl-piperazine-1-carboxylic acid 2-chloro-6-fluoro-4-prop-2-ynyloxy-benzyl ester.

Most preferred compounds according to formula I are:

S-4-[(2-propylamino)carbonyl]oxybenzyl piperazine-1-thiocarboxylate;
S-4-[(benzylamino)carbonyl]oxybenzyl piperazine-1-thiocarboxylate;
S-4-[(tert-butylamino)carbonyl]oxybenzyl piperazine-1-thiocarboxylate;
2,6-difluoro-4-difluoromethoxybenzyl cis-2,6-dimethylpiperazine-1-carboxylate;
(R)-4-difluoromethoxybenzyl 2-ethylpiperazine-1-carboxylate;
(R)-2,6-difluoro-4-propoxybenzyl 2-methylpiperazine-1-carboxylate;
cis-2,6-dimethyl-piperazine-1-carboxylic acid 4-(3,5-dimethyl-isoxazol-4-ylmethoxy)-2,6-difluoro-benzyl ester;
2-fluoro-5-(2-propenyl)oxybenzyl cis-2,6-dimethylpiperazine-1-carboxylate;
(R)-2-fluoro-5-pentyloxybenzyl 2-methylpiperazine-1-carboxylate;
5-(cyclopropylmethyl)oxy-2-fluorobenzyl cis-2,6-dimethylpiperazine-1-carboxylate;
(R)-2-ethyl-piperazine-1-carboxylic acid 4-cyclopropylmethoxy-2,6-difluoro-benzyl ester;
(R)-2-ethyl-piperazine-1-carboxylic acid 2,6-difluoro-4-propoxy-benzyl ester;
(R)-2-ethyl-piperazine-1-carboxylic acid 4-allyloxy-2,6-difluoro-benzyl ester;
(R)-2-ethyl-piperazine-1-carboxylic acid 2,6-difluoro-4-prop-2-ynyloxy-benzyl ester;
(R)-2-ethyl-piperazine-1-carboxylic acid 4-cyclopropylmethoxy-2-chloro-6-fluoro-benzyl ester;
(R)-2-ethyl-piperazine-1-carboxylic acid 2-chloro-6-fluoro-4-propoxy-benzyl ester;
(R)-2-ethyl-piperazine-1-carboxylic acid 4-allyloxy-2-chloro-6-fluoro-benzyl ester and
(R)-2-ethyl-piperazine-1-carboxylic acid 2-chloro-6-fluoro-4-prop-2-ynyloxy-benzyl ester.

Processes for the manufacture of the compounds according to formula I are an object of the present invention. The substituents and indices used in the following schemes have the significance given above unless indicated to the contrary.

Compounds of formula (I) where $R^1$ to $R^4$, $A^1$, $A^2$ and n are as previously defined may be conveniently prepared according to Reaction Scheme 1.

Reaction Scheme 1

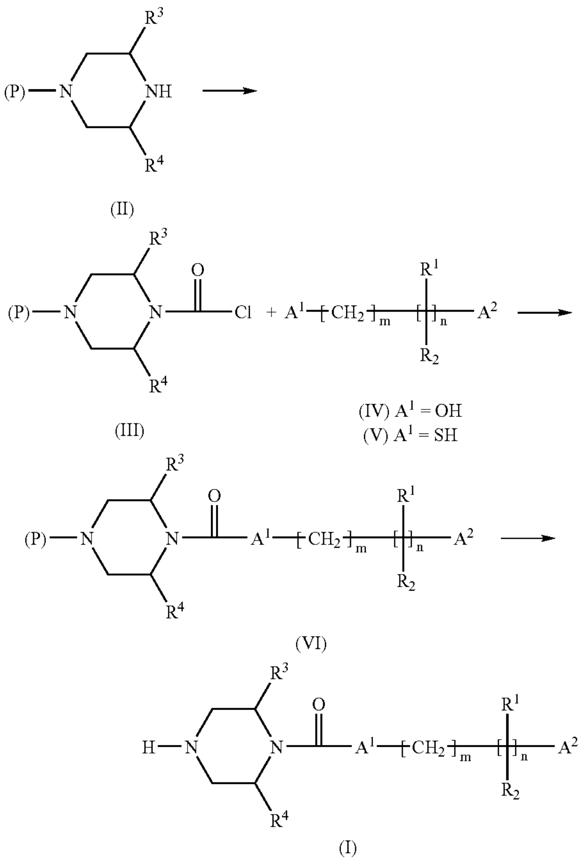

(II)

(III)

(IV) $A^1$ = OH (V) $A^1$ = SH (VI)

(I)

A compound of formula (VI) can be prepared by reaction of the piperazine carbamoyl chloride (III) with an alcohol (IV) or thiol (V) in the presence of a suitable base such as sodium hydride, triethylamine, PS-BEMP or pyridine in a solvent such as acetonitrile, N-methylpyrrolidinone, dimethyl formamide, tetrahydrofuran or dichloromethane. The piperazine may be protected using a suitable protecting group (P) e.g. tert-butoxycarbonyl, 9-fluorenylmethoxycarbonyl, allyloxycarbonyl, trimethylsilyl, 3,4-dimethoxybenzyl and trityl, preferably tert-butoxycarbonyl and 9-fluorenylmethoxycarbonyl. These protective groups may also be bound to a polymeric resin, e.g., polystyrene-PEG-bound trityl.

The protected piperazine-carbamoyl chloride (III) may be synthesized from a protected piperazine (II) by treatment with a reagent such as phosgene, diphosgene or triphosgene in the presence of a base such as pyridine in a suitable solvent, for instance dichloromethane. Where necessary, protected piperazines (II) can be synthesized from commercially available monoalkyl- or dialkyl-piperazines by treatment with reagents known to introduce the desired protecting group e.g. di-tert-butyl dicarbonate or 9-fluorenylmethyl chloroformate. The protection of the piperazines may also be accomplished by covalent linkage of the appropriate piperazine nitrogen to a polymeric resin, e.g., polystyrene-PEG-hydroxytrityl resin in the case of P=trityl, using methods known in the art. Mono or dialkyl-piperazines may be prepared by those skilled in the art via a variety of methods which includes, but is not limited to: reduction of mono or dialkylpyrazines using e.g. catalytic hydrogenation or dissolved metal reagents; alkylation of ethylene diamine and alkylated analogues with e.g. alkyl-substituted 1,2-dihaloethane compounds, alkyl-substituted 1,2-ethanediol compounds or alkyl-substituted ethane-1,2-dialkylsulfonate compounds; reduction of a monoalkyl substituted 2,5-diketopiperazine with e.g. sodium or lithium borohydride or lithium aluminium hydride.

The alcohol (IV) may be commercially available or alternatively may be synthesized via reduction of an aldehyde, carboxylic acid, ester or amide derivative with a reagent such as sodium or lithium borohydride or lithium aluminium hydride in a suitable solvent or alternatively via Grignard addition of alkyl- or aryl-magnesium halides or alkyl- or aryl-lithium nucleophiles to aldehydes or carboxylic esters or amides. The aldehydes, carboxylic acids, esters and amides may be commercially available or synthesized according to methods known to those skilled in the art. Such methods include but are not limited to formylation of an aryl or heteroaryl containing starting-material, vicarious nucleophilic substitution, hydrolysis of an alkyl halide or oxidation of an aryl-methyl (tolyl) group.

Thiols of formula (V) may be prepared from (IV) by a variety of methods e.g. displacement of an activated derivative of the hydroxyl of (IV) with a sulfur nucleophile such as thiolacetic acid followed by treatment with a reducing agent such as lithium aluminium hydride. Activated hydroxyl derivatives include, but are not limited to, mesylates, tosylates and in situ activation with phosphorus compounds such as triphenylphosphine.

Thiols of formula (V) may be replaced by xanthogenates, which are prepared in situ from alcohol (IV) with carbon disulfide and a base such as sodium or potassium hydroxide in a solvent such as tetrahydrofuran or acetone.

Compounds of formula (I) may be prepared from compounds of formula (VI) by reaction with a reagent known to selectively remove the protecting group (P) e.g. tert-butoxycarbonyl, triphenylmethyl and 3,4-dimethoxybenzyl may be removed using an acid such as hydrochloric acid or trifluoroacetic acid and 9-fluorenylmethoxycarbonyl may be removed by treatment with a base such as morpholine.

Alternatively compounds of formula (I) where $A^1$=O may be prepared via Reaction Scheme (2) below.

Reaction Scheme 2

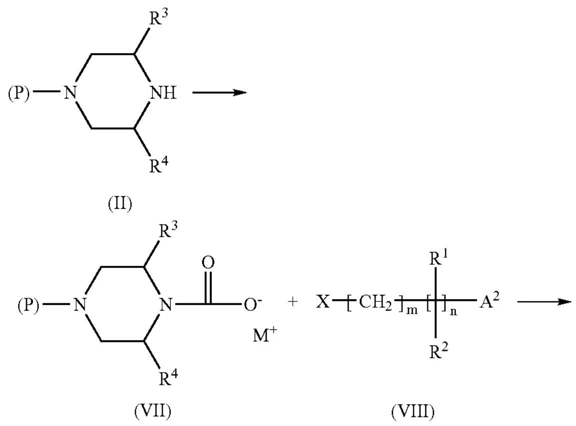

(II)

(VII)

(VIII)

-continued

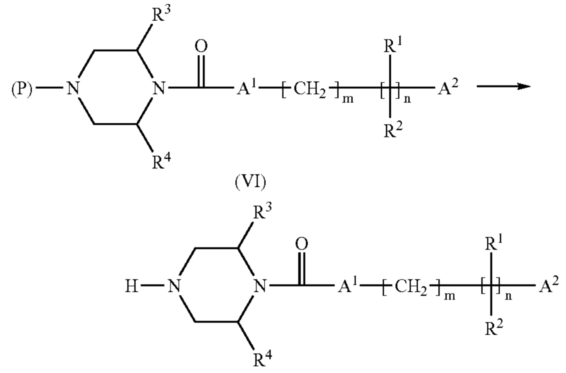

(VI)

(I)

Reaction of a piperazine (II) with carbon dioxide in the presence of a base such as tetraalkylammonium (for alkyl preferably ethyl or butyl) hydrogencarbonate or potassium hydride or butyl-lithium or a metal such as lithium may produce the piperazine-carboxylate (VII). Treatment of (VII) with halide (VIII) (X means Cl, Br or I) in a suitable solvent may give a compound of formula (VI) where $A^1$=O. Halides of formula (VIII) may be synthesized if not commercially available by methods known to those skilled in the art. Such methods include, but are not limited to, conversion of an alcohol of formula (IV) where $A^1$=O via treatment with triphenylphosphine and a halogen such as bromine; formation and displacement of an alkyl or arylsulfonate such as mesylate or tosylate with a halide salt such as sodium bromide in a solvent such as tetrahydrofuran or acetone and halogenation of an aralkyl or heteroaralkyl compound with a reagent such as N-bromosuccinimide optionally in the presence of a co-reagent such as AIBN (2,2'-azobisisobutyronitrile) or benzoyl peroxide. Compounds of formula (VI) can be transformed into compounds of formula (I) by methods as described above in Reaction Scheme 1.

If, in any of the other processes mentioned herein, $R^1$, $R^2$, $R^3$, $R^4$ and the substituent groups attached to $A^2$ are other than the one required, the substituent group may be converted to the desired substituent by known methods. $R^1$, $R^2$, $R^3$, $R^4$ and the substituent groups attached to $A^2$ may also need protecting against the conditions under which the reaction is carried out. In such a case, the protecting group may be removed after the reaction has been completed.

Alternatively compounds of formula (I) where $A^1$=O may be prepared via Reaction Scheme (3) below.

Reaction Scheme 3

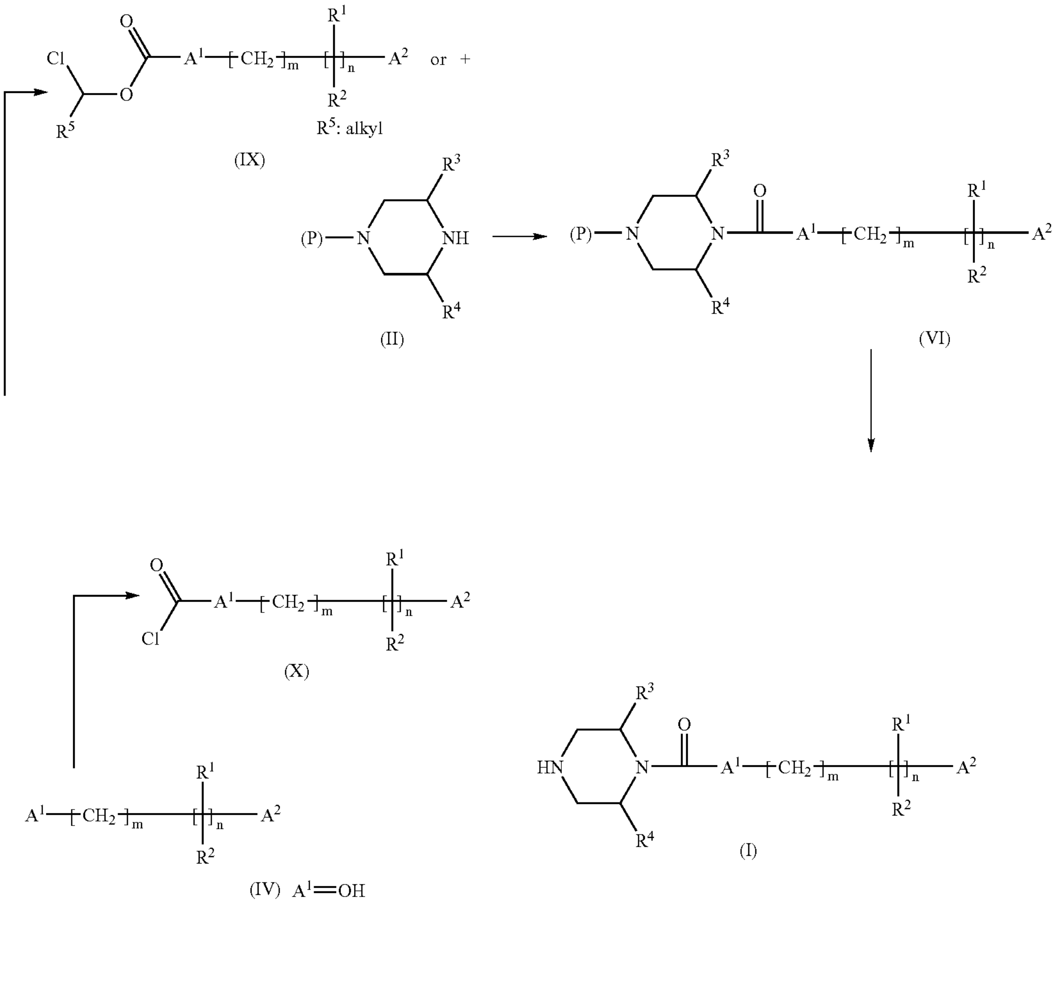

(IX)

(II)

(VI)

(X)

(IV) $A^1$=OH (I)

A compound of formula (VI) can be prepared by reaction of the piperazine (II) with an activated derivative (IX) or (X) of alcohol (IV) optionally in the presence of a suitable base such as triethylamine, PS-BEMP or pyridine in a solvent such as acetonitrile, N-methylpyrrolidinone, dimethyl formamide, tetrahydrofuran or dichloromethane. The piperazine may be protected using a suitable protecting group (P) e.g. tert-butoxycarbonyl, 9-fluorenylmethoxycarbonyl, allyloxycarbonyl, trimethylsilyl, 3,4-dimethoxybenzyl and trityl, preferably tert-butoxycarbonyl and 9-fluorenylmethoxycarbonyl.

The activated derivative (IX) may be synthesizedsynthesized from alcohol (IV) with 1-chloroalkyl chloroformate, preferably 1-chloroethyl chloroformate, in the presence of a suitable base such as triethylamine, PS-BEMP or pyridine in a solvent such as acetonitrile, N-methylpyrrolidinone, dimethyl formamide, tetrahydrofuran or dichloromethane.

The activated derivative (X) is either commercially available or may be synthesizedsynthesized from alcohol (IV) by treatment with a reagent such as phosgene, diphosgene, or triphosgene, optionally in the presence of a base such as pyridine, in a suitable solvent, e.g., dichloromethane or tetrahydrofuran.

Compounds of formula (I) may be prepared from compounds of formula (VI) by reaction with a reagent known to selectively remove the protecting group (P) e.g. tert-butoxycarbonyl and 3,4-dimethoxybenzyl may be removed using an acid such as hydrochloric acid or trifluoroacetic acid and 9-fluorenylmethoxycarbonyl may be removed by treatment with a base such as morpholine.

The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

A further object of the present invention is the process for the preparation of a compound according to formula I comprising the deprotection of a compound according to formula (VI)

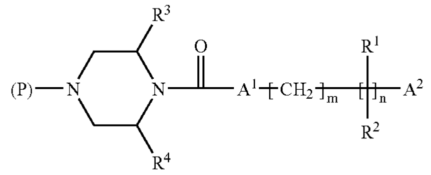

wherein $R^1$ to $R^4$, $A^1$, $A^2$, m and n are defined as before and (P) is a nitrogen protecting group. Examples of nitrogen protecting groups are tert-butoxycarbonyl, 9-fluorenylmethoxycarbonyl, allyloxycarbonyl, trimethylsilyl, 3,4-dimethoxybenzyl and trityl, preferably tert-butoxycarbonyl and 9-fluorenylmethoxycarbonyl.

Another preferred aspect of this invention are the following intermediates:

Cis-4-chlorocarbonyl-2,6-dimethyl-piperazine-1-carboxylic acid tert-butyl ester;

Piperazine-1,4-dicarboxylic acid tert-butyl ester 4-trifluoromethoxy-benzyl ester;

Piperazine-1,4-dicarboxylic acid tert-butyl ester 2-fluoro-benzyl ester;

4-(4-Benzyloxy-benzylsulfanylcarbonyl)-piperazine-1-carboxylic acid tert-butyl ester;

4-[4-(4-Fluoro-benzyloxy)-benzylsulfanylcarbonyl]-piperazine-1-carboxylic acid tert-butyl ester;

Piperazine-1,4-dicarboxylic acid 4-benzyloxy-benzyl ester 9H-fluoren-9-ylmethyl ester;

Piperazine-1,4-dicarboxylic acid 9H-fluoren-9-ylmethyl ester 4-(4-fluoro-benzyloxy)-benzyl ester;

Piperazine-1,4-dicarboxylic acid 9H-fluoren-9-ylmethyl ester 4-methoxy-benzyl ester;

Piperazine-1,4-dicarboxylic acid benzhydryl ester 9H-fluoren-9-ylmethyl ester;

(RS)-Piperazine-1,4-dicarboxylic acid 9H-fluoren-9-ylmethyl ester 1-phenyl-ethyl ester;

cis-2,6-Dimethylpiperazine-1,4-dicarboxylic acid 5-(2-chloropyridyl)methyl ester tert-butyl ester;

cis-2,6-Dimethylpiperazine-1,4-dicarboxylic acid 5-[2-(3-chlorobenzyloxy)]pyridyl-methyl ester tert-butyl ester;

Piperazine-1,4-dicarboxylic acid 5-[2-(3-chlorobenzyloxy)]pyridyl-methyl ester tert-butyl ester;

[(4-tert-Butyl-dimethylsilyloxy)benzylsulfanylcarbonyl]-piperazine-4-carboxylic acid tert-butyl ester;

Piperazine-1,4-dicarboxylic acid (3-tert-butyldimethylsilyloxy)benzyl ester tert-butyl ester;

Piperazine-1,4-dicarboxylic acid (3-hydroxy)benzyl ester tert-butyl ester;

Piperazine-1,4-dicarboxylic acid 3-(2-phenylethoxy)benzyl ester tert-butyl ester;

4-(4-Fluoro-benzyloxy)-phenyl-methanethiol;

(RS)-Carbonic acid 4-benzyloxy-benzyl ester 1-chloro-ethyl ester;

(RS)-Carbonic acid 1-chloro-ethyl ester 4-(4-fluoro-benzyloxy)-benzyl ester;

(RS)-Carbonic acid 1-chloro-ethyl ester 4-methoxy-benzyl ester;

(RS)-Carbonic acid benzhydryl ester 1-chloro-ethyl ester;

(RS)-Carbonic acid 1-chloro-ethyl ester 1-phenyl-ethyl ester.

Use of the compounds of formula I as therapeutically active substances is a further object of the invention.

A further object of the invention are compounds of formula I as described above for the production of medicaments for the prophylaxis and therapy of illnesses which are caused by disorders associated with the 5-$HT_2$ receptor, particularly with the 5-$HT_{2a}$, 5-$HT_{2b}$ or 5-$HT_{2c}$ subtype. Most preferred is the 5-$HT_{2c}$ subtype.

Likewise an object of the invention is a pharmaceutical composition comprising a compound of formula I and a therapeutically inert carrier.

A further object of the invention is a compound of formula I for the production of pharmaceutical compositions for the treatment and prophylaxis of eating disorders and obesity.

Also an object of the invention is the use of a compound according to formula I for the production of medicaments for the treatment of diabetes mellitus, Type I diabetes, Type II diabetes, diabetes secondary to pancreatic disease, diabetes related to steroid use, Type III diabetes, hyperglycaemia, diabetic complications and insulin resistance.

Particularly, a further object of the invention is the use of a compound of formula I for the production of medicaments for the treatment of Type II diabetes.

Another object of the invention is the use of compounds in accordance with formula I for the production of medicaments for the treatment and prophylaxis of disorders of the central nervous system, cardiovascular disorders, gastrointestinal disorders, diabetes insipidus and sleep apnoea.

Particularly an object of the invention is the above method of treatment, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

A further preferred embodiment of the present invention is the above mentioned method of treatment by administering the compounds according to formula I, wherein the cardiovascular disorder is thrombosis.

Also preferred is the mentioned use of the compounds according to formula I, wherein the gastrointestinal disorder is dysfunction of gastrointestinal motility.

A further object of the invention are compounds in accordance with formula I, when manufactured according to the described process.

A further embodiment of the present invention is a method for the treatment and prophylaxis of disorders of the central nervous system, cardiovascular disorders, gastrointestinal disorders, diabetes insipidus, and sleep apnoea., which method comprises administering an effective amount of a compound of formula I as described. Preferred is this method, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

A preferred object of the invention is a method for the treatment and prophylaxis of eating disorders and obesity, which method comprises administering an effective amount of a compound of formula I.

Another object of the present invention is a method for the treatment and prophylaxis of disorders selected from diabetes mellitus, Type I diabetes, Type II diabetes, diabetes secondary to pancreatic disease, diabetes related to steroid use, Type III diabetes, hyperglycaemia, diabetic complications and insulin resistance, which method comprises administering an effective amount of a compound in accordance with formula I. Particularly preferred is the above method for the treatment and prophylaxis of Type II diabetes.

Particularly preferred is a method for the treatment and prophylaxis of Type II diabetes.

A further preferred object is a method of treatment of obesity in a human in need of such treatment which comprises administration to the human a therapeutically effective amount of a compound according to formula I and a therapeutically effective amount of a lipase inhibitor, particularly, wherein the lipase inhibitor is orlistat.

Also an object of the invention are the method as described above for the simultaneous, separate or sequential administration.

A further object of the invention is the use of a compound of formula I in the manufacture of a medicament for the treatment and prevention of obesity in a patient who is also receiving treatment with a lipase inhibitor and particularly, wherein the lipase inhibitor is orlistat.

Another object of the invention is the use of a compound according to formula I in the manufacture of a medicament for the treatment and prevention of diabetes mellitus, Type I diabetes, Type II diabetes, diabetes secondary to pancreatic disease, diabetes related to steroid use, Type III diabetes, hyperglycaemia, diabetic complications and insulin resistance in a patient who is also receiving treatment with a lipase inhibitor and particularly, wherein the lipase inhibitor is orlistat.

Particularly preferred is the use of a compound according to formula I in the manufacture of a medicament for the treatment and prevention of Type II diabetes in a patient who is also receiving treatment with a lipase inhibitor and particularly, wherein the lipase inhibitor is orlistat.

Also an object of the invention is the pharmaceutical composition comprising a compound of formula I, a therapeutically inert carrier and further a therapeutically effective amount of a lipase inhibitor, particularly, wherein the lipase inhibitor is orlistat.

The compounds of formula (I) may be used in the treatment (including prophylactic treatment) of disorders associated with 5-$HT_2$ receptor function. The compounds may act as receptor agonists or antagonists. Preferably, the compounds may be used in the treatment (including prophylactic treatment) of disorders associated with 5-$HT_{2b}$ and/or 5-$HT_{2c}$ receptor function. Preferably, the compounds may be used in the treatment (including prophylactic treatment) of disorders where a 5-$HT_{2c}$ receptor agonist is required.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

Assay Procedures

Binding to Serotonin Receptors

The binding of compounds of formula (I) to serotonin receptors was determined in vitro by standard methods. The preparations were investigated in accordance with the assays given below.

Method (a): For the binding to the 5-$HT_{2C}$ receptor, the 5-$HT_{2C}$ receptors were radiolabeled with [$^3$H]-5-HT. The affinity of the compounds for 5-$HT_{2C}$ receptors in a CHO cell line was determined according to the procedure of D. Hoyer, G. Engel and H. O. Kalkman, European J. Pharmacol., 1985, 118, 13–23.

Method (b): For the binding to the 5-$HT_{2B}$ receptor, the 5-$HT_{2B}$ receptors were radiolabeled with [$^3$H]-5-HT. The affinity of the compounds for human 5-$HT_{2B}$ receptors in a CHO cell line was determined according to the procedure of K. Schmuck, C. Ullmer, P. Engels and H. Lubbert, FEBS Lett., 1994, 342, 85–90.

Method (c): For the binding to the 5-$HT_{2A}$ receptor, the 5-$HT_{2A}$ receptors were radiolabeled with [$^{125}$I]-DOI. The affinity of the compounds for 5-$HT_{2A}$ receptors in a CHO cell line was determined according to the procedure of D. J. McKenna and S. J. Peroutka, J. Neurosci., 1989, 9, 3482–90.

The thus determined activity of the compound presented as a calculated Ki of the Example is shown in Table 1. The Ki value is definied as an inhibition constance and is determined from the IC50 value as described in Cheng, Yung-Chi and Prusoff, W. H., Biochem. Pharmacol., 1973, 22(23), 3099–108.

TABLE 1

| Compound | Method (a) Ki (2C)/nM | Method (b) Ki (2B)/nM | Method (c) Ki (2A)/nM |
|---|---|---|---|
| 32 | 15 | 370 | 6 |
| 22 | 44 | 4000 | 44 |
| 63 | 33 | 8300 | 550 |
| 121 | 15 | 8400 | 200 |

Preferred Ki (2C) values are below 10000 nM; especially preferred Ki (2C) values are below 1000 nM, particularly preferred Ki (2C) values are below 100 nM. Most preferred Ki (2C) values are below 50 nM.

Functional Activity

The functional activity of compounds of formula (I) was assayed using a Fluorimetric Imaging Pate reader (FLIPR). CHO cells expressing the human 5-$HT_{2C}$ or human 5-$HT_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 μL/well of assay buffer (Hanks balanced salt solution containing 20 mM Hepes and 2.5 mM probenecid). The drug (dissolved in 50 □L of the assay buffer) was added at a rate of 70 μL/sec to each well of the FLIPR 96 well plate during fluorescence measurements. The measurements were taken at 1 sec intervals and the maximum fluorescent signal was measured (approx 10–15 secs after drug addition) and compared with the response produced by 10 μM 5-HT (defined as 100%) to which it was expressed as a percentage response (relative efficacy). Dose response curves were constructed using Graphpad Prism (Graph Software Inc.).

TABLE 2

| | h5-$HT_{2C}$ | | h5-$HT_{2A}$ | |
|---|---|---|---|---|
| Compound | EC50 (nM) | Relative Efficacy (%) | EC50 (nM) | Relative Efficacy (%) |
| 32 | 38 | 65 | 560 | 22 |
| 22 | 100 | 56 | 220 | 24 |
| 63 | 33 | 74 | 370 | 25 |
| 121 | 22 | 91 | 550 | 11 |

The compounds of formula (I) have activity at the h5-$HT_{2C}$ receptor in the range of 10,000 to 0.1 nM.

Preferred activities at the h5-$HT_{2C}$ receptor are below 10000 nM; especially preferred below 1000 nM, particularly preferred activities are below 100 nM. Most preferred activity at the h5-$HT_{2C}$ receptor are below 50 nM.

The compounds of formula (I) have maximum functional activity at the h5-$HT_{2C}$ receptor in the range of 0 to 100%.

Preferred maximal functional activity at the h5-$HT_{2C}$ receptor as described above are above 30%; especially preferred above 50%, particularly preferred above 60%. Most preferred maximal functional activity at the h5-$HT_{2C}$ receptor are above 70%.

Regulation of Feeding Behaviour

The in vivo activity of compounds of formula (1) was assayed for ability to regulate feeding behaviour by assaying food consumption in food deprived animals as follows.

Test compounds are assessed following acute administration. Each study utilises a between-subjects design (typically n=8) and compares the effects of doses of the test agent to those of vehicle and a positive control.

The anorectic drug d-fenfluramine normally serves as a positive control. The route of drug administration, drug volume and injection-test-interval are dependent upon the compounds used. A palatable wet mash, made by adding powdered lab chow and water in a ratio of 1:2 and mixing to a smooth consistency, is presented in 120 mL glass jars for 60 minutes each day. Intake is measured by weighing before and after each session. Care is taken to collect all spillage. Animals are allowed to habituate to the wet mash meal for 10 days. After drug administration, animals are allowed to consume the wet mash. Food consumption is assayed at pre-determined time points (typically, 1, 2 and 4 hours after administration). Food intake data are subjected to one-way analysis of variance (ANOVA) with drug as a between-subjects factor. A significant main effect is followed up by the performance of Dunnett's test in order to assess which treatment mean(s) are significantly different from the control mean. All statistical analyses were performed using Statistica Software, Version 5.0 (Statsofr Inc.) and Microsoft Excel 7.0 (Microsoft Corp.).

The thus determined activity of the Example indicated that the compounds maintain significant hypophagia 3 hours after a dose of 30 mg/kg per os.

EXAMPLES

Abbreviations:

PS-BEMP: 2-tert-Butylimino-2-diethylamino-1,3-dimethyl-perhydro-1,3,2-diazo-phosphorine on polystyrene PS-NH2: 4-(Aminomethyl)-polystyrene TBME: tert-Butyl methyl ether Starting Materials:

4-chlorocarbonyl-piperazine-1-carboxylic acid tert-butyl ester was prepared following a modified procedure of document DE 25 50 111, Rhone-Poulenc.

(+/−) 4-chlorocarbonyl-2-ethylpiperazine-1-carboxylic acid tert-butyl ester was prepared using the method described in DE 2550111 according to the following procedure:

To a stirred solution of 2-ethylpiperazine dihydrochloride (J. Org. Chem., 1987, 52(6), 1045, 5.0 g) and triethylamine (9.3 ml) in DCM (50 ml) at 0° C. was added di-tert-butyl-dicarbonate (6.5 g). The mixture was warmed to room temperature, stirred for 2 h, washed successively with water, dilute sodium hydroxide solution, water and brine then dried (sodium sulfate) and concentrated in vacuo to give the product as a clear oil (5.1 g); $\delta_H$ (400 MHz, $CDCl_3$) 3.78 (1H, m), 3.71 (1H, d, J 12.5 Hz), 2.81 (1H, dt, J 11.5, 2.5 Hz), 2.69 (1H, t, J 10.5 Hz), 2.48 (1H, td, J 11.5, 3 Hz), 2.29 (1H, m), 2.17 (1H, m), 1.39 (9H, s), 1.31 (1H, dd, J 7.5, 6 Hz), 1.25 (1H, dd, J 7.5, 6 Hz) and 0.87 (3H, t, J 7 Hz); GC (150° C.-10 min-320° C.) 93%, 5.13 min.

(+/−) 4-Chlorocarbonyl-2-ethylpiperazine-1-carboxylic acid tert-butyl ester: a solution of (RS) 4-tert-butoxycarbonyl-2-ethylpiperazine (3.95 g) and pyridine (1.64 ml) in DCM (35 ml) was added dropwise to a stirred solution of triphosgene (2.1 g) in DCM (100 ml) at 0° C. under Ar. The mixture was warmed to room temperature, stirred for 30 min then washed with water (100 ml) and brine (100 ml). The organic solution was dried (sodium sulfate) and concentrated in vacuo. The residue was dissolved in isohexane, filtered and concentrated in vacuo to give the product as a clear oil (3.73 g) which was used without further purification; $\delta_H$ (400 MHz, $CDCl_3$) 4.39–3.80 (4H, m), 3.39–2.69 (3H, m), 1.66 (2H, m), 1.47 (9H, s), 0.96 (2.7H, d, J 7 Hz) and 0.89 (0.3H, d, J 7 Hz); GC (150° C.-10 min-320° C.) 83%, 8.72 min.

(+/−) 4-chlorocarbonyl-2-methylpiperazine-1-carboxylic acid tert-butyl ester and (R) 4-chlorocarbonyl-2-methylpiperazine-1-carboxylic acid tert-butyl ester were prepared according to the above method from commercially available racemic 2-methylpiperazine and (R) 2-methylpiperazine respectively.

Tetrabutylammonium hydrogencarbonate was prepared as described in St. C. Cheng, Ch. A. Blaine, M. G. Hill, K. R. Mann, Inorg. Chem. 35, 7704 (1996); C. Venturello, R. D'Aloisio, Synthesis 1985, 33.

N-Boc-piperazine is commercially available.

N-Fmoc-piperazine hydrobromide is commercially available.

4-(4-Fluorobenzyloxy)-benzyl alcohol is commercially available.

4-(4-Fluoro-benzyloxy)-phenyl-methanethiol was prepared in analogy to S. Vetter, Synth. Commun. 28, 3219 (1998).

cis-N-Boc-2,6-dimethylpiperazine was prepared as described in A. Muehlebach, P. Pino, Helv. Chim. Acta 73, 839 (1990).

2,6-Difluoro-4-hydroxybenzyl alcohol was prepared according to the following procedure:

To a stirred solution of 3,5-difluorophenol (14.5 g) and potassium hydroxide (85%, 7.4 g) in water (30 mL) at 60° C. was added dropwise over 1 hour a solution of aqueous formaldehyde (37%, 15.3 mL) in added water (30 mL). The mixture was cooled to 40° C., stirred for 18 hours then cooled to 0° C. The mixture was carefully acidified with conc. HCl during which time a white precipitate appeared. The mixture was stirred for 30 minutes at 0° C. then filtered. The filter-cake was washed with ice-cold water and dried to give the product as a white solid (8.1 g, 46%); $\delta_H$ (400 MHz, DMSO-$d_6$) 10.23 (1H, m, OH), 6.44 (1H, t, J 4 Hz), 6.39 (1H, t, J 4 Hz), 4.95 (1H, t, J 5.5 Hz, OH) and 4.38 (2H, d, J 5.5 Hz); HPLC (XTERRA, MeOH—$NH_4OAc$, 50%→80%) 94% (0.62 min).

2-Fluoro-5-hydroxybenzyl alcohol was prepared according to the following procedure: 2-Fluoro-5-hydroxybenzaldehyde: to a stirred solution of 2-fluoro-5-methoxybenzaldehyde (18.3 g) in dichloromethane (200 mL) at 0° C. was added dropwise a solution of boron tribromide in dichloromethane (1M, 120 mL, 1 eq.). The mixture was stirred for 3 h then concentrated to a volume of ~50 mL and partitioned between ethyl acetate (500 mL) and water (500 mL). The organic layer was washed (water), dried (magnesium sulfate) and concentrated to give a red oil (22.7 g). The oil was purified by column chromatography ($SiO_2$, DCM→DIPE) to give the product as a pink crystalline solid (9.9 g, 59% yield);

2-Fluoro-5-hydroxybenzyl alcohol: to a stirred solution of 2-fluoro-5-hydroxybenzaldehyde (4.1 g) in methanol (50 mL) at 0° C. was added portionwise sodium borohydride (0.55 g). The mixture was warmed to room temperature, stirred for 1 hour then partitioned between water (200 mL) and ethyl acetate (2×200 mL). The combined organics were washed (brine), dried (magnesium sulfate) and concentrated to give 2-fluoro-5-hydroxybenzyl alcohol as a yellow oil which crystallised on standing overnight (4.1 g, 95% yield):

Alternatively 2-fluoro-5-hydroxybenzyl alcohol was prepared according to the following procedure:

2-Fluoro-5-hydroxybenzyl alcohol: to a stirred solution of 2-fluoro-5-methoxybenzaldehyde (1.0 g) in toluene (30 ml) at 0° C. under Ar was added dropwise a solution of DIBAL-H (1.0 M, toluene, 3.2 ml). The mixture was stirred for 30 min then heated to 100° C. and stirred for 18 h. The mixture was cooled to 0° C. and quenched by dropwise addition of ethyl acetate (5 ml), methanol (2 ml) and water (1 ml). The mixture was stirred for 30 min then partitioned between dil. hydrochloric acid (30 ml) and ethyl acetate (2×30 ml). The combined organics were washed (water, brine), dried (sodium sulfate) and concentrated in vacuo. The residue was triturated with isohexane-DCM (10:1) to give the product as a white solid (0.56 g, 61%): $\delta_H$ (400 MHz, DMSO-$d_6$) 9.24 (1H, m, OH), 6.90 (1H, dd, J 10, 9 Hz), 6.85 (1H, q, J 3 Hz), 6.60 (1H, m), 5.15 (1H, m, OH) and 4.46 (2H, s); HPLC (XTERRA, 20/50, 280 nm) 93% (1.09 min).

(R) 2-Methyl-piperazine, (RS) 2-methylpiperazine and (RS) 2-ethylpiperazine were loaded onto solid-phase supports using the following procedure:

A mixture of polystyrene-PEG-hydroxytrityl resin (4 g, NovaBiochem, 0.26 mmol/g loading, 1.04 mmol), freshly distilled acetyl chloride (5 mL, 56 mmol) and toluene (50 mL) was heated under reflux for 3 h then cooled to room temperature. The resin was filtered off and washed three times each with toluene, THF, dichloromethane and toluene again. The resin was used in the next step immediately.

To a 20 mL solid-phase tube was added approximately half of the resin from the previous step (2 g, 0.52 mmol)) and dry THF (10 mL). The tube was shaken for 10 minutes then the solvent was removed by suction filtration. More THF (10 mL) and (R) 2-methylpiperazine (0.18 g, 1.8 mmol) were added and the mixture was sealed and shaken for 18 hours. The solvent was removed by suction filtration and the resin was sequentially washed three times with THF, methanol, dichloromethane and THF again then dried under vacuum.

S-4-hydroxybenzyl piperazine-1-thiocarboxylate was prepared according to the following procedure adapted from: M. R. Tremblay et al, Bioorg. Med. Chem., (1999), 7, 1013–1023.

4-(tert-butydimethylsilyloxy)-benzaldehyde: to a stirred solution of 4-hydroxybenzaldehyde (25.0 g, 205 mmol) in dry DMF (200 mL) was added imidazole (28.0 g, 410 mmol) and TBDMS-Cl (32.4 g, 215 mmol) under an argon atmosphere. The resulting mixture was stirred for 4 h at room temperature (rt) then water was added and the mixture was extracted with ether (2×300 mL) and dichloromethane (2×300 mL). The combined organics were dried ($MgSO_4$), filtered and concentrated under vacuum. The crude oil was purified by filtration through silica gel (eluting with hexane-EtOAc, 95:5) to give the product as a colourless oil (48.0 g, 99%).

4-(tert-Butydimethylsilyloxy)-benzyl alcohol: to a stirred solution of 4-(tert-butydimethylsilyloxy)-benzaldehyde (48.0 g, 203 mmol) in methanol (200 mL) at 0° C. was added sodium borohydride (11.6 g, 305 mmol) and the reaction was stirred at 0° C. for 45 min. Water (200 mL) was added and the methanol was removed under reduced pressure. The mixture was extracted with ether (2×200 mL) and ethyl acetate (2×200 mL). The combined organics were dried ($MgSO_4$), filtered and concentrated under vacuum to give the crude product, which was used without further purification (48 g, quantitative).

Ethanethioic acid, S-[4-(tert-butyldimethylsilyloxy)benzyl] ester: To an efficiently stirred solution of triphenylphosphine (81 g, 309 mmol) in THF (200 mL) was added diethyl azodicarboxylate (62.5 g, 309 mmol) at 0° C. The mixture was stirred for 30 min, after which time a thick white precipitate was obtained. The crude 4-(tert-butydimethylsilyloxy)-benzyl alcohol (48 g) in THF (100 mL) and thiolacetic acid (36.1 g, 474 mmol) were added dropwise while the temperature was maintained below 10° C. The reaction was stirred overnight while keeping the internal temperature below 10° C. The solvent was removed in vacuo and the residue was purified by flash column chromatography [$SiO_2$: isohexane-ethyl acetate (9:1)] to give the product as a viscous brown oil (30.7 g, 50%).

4-(tert-Butyldimethylsilyloxy)-benzenemethanethiol: to a stirred solution of ethanethioic acid, S-[4-(tert-butyldimethylsilyloxy)benzyl] ester (30.7 g, 104 mmol) in dry THF (300 mL) at 0° C. under an argon atmosphere was added lithium aluminium hydride (5.9 g, 156 mmol). The reaction was stirred for 3 h at 0° C. The mixture was quenched by careful addition of EtOAc then water. The pH was brought to 5 with an aqueous solution of 10% HCl and the resulting slurry was filtered. The filtrate was extracted with EtOAc (2×100 mL) and the combined organic layers were washed successively with Rochelle's salt, brine, dried ($MgSO_4$), filtered and concentrated to give the product as a green oil (22.1 g, 84%).

S-4-(tert-butyl-dimethylsilyloxy)benzyl 4-tert-butoxycarbonylpiperazine-1-thiocarboxylate: to a stirred solution of 4-(tert-butyldimethylsilyloxy)-benzenemethanethiol (10.5 g, 41 mmol) and triethylamine (69 mmol, 9.6 mL) in THF (500 mL) at 0° C. was added 4-tert-butoxycarbonyl-1-chlorocarbonylpiperazine (8.56 g, 34 mmol) and DMAP (6.9 mmol, 0.84 g). The reaction mixture was warmed to 50° C. and stirred for 3 h then poured into water (500 mL) and extracted with EtOAc (2×250 mL). The combined organic extracts were washed with water (250 mL) then brine (500 mL), then dried ($MgSO_4$) and concentrated to reveal a brown oil. Chromatography [$SiO_2$: 90/10, hexane/EtOAc)] gave the product as a yellow oil which crystallised on standing (13.4 g, 85%): m.p. 53–54° C. $^1$H-NMR (400 MHz, $CDCl_3$): 0.18 (6H, s), 0.96 (9H, s), 1.46 (9H, s), 3.42–3.51 (8H, m), 4.12 (2H, s), 6.75 (2H, d, J=8.5 Hz) and 7.18 (2H, d, J=8.5 Hz).

S-4-hydroxybenzyl 4-tert-butoxycarbonylpiperazine-1-thiocarboxylate: to a stirred solution of S-4-(tert-butyldimethylsilyloxy)benzyl 4-tert-butoxycarbonylpiperazine-1-thiocarboxylate (10 g, 22 mmol) in THF (100 mL) was added a solution of TBAF in THF (1 N, 24 mL, 24 mmol). The mixture was stirred at room temperature for 40 min then diluted with water (200 mL) and extracted with EtOAc (2×250 mL). The combined organic extracts were washed successively with water (250 mL) and brine (500 mL) then dried ($MgSO_4$), filtered and concentrated to reveal a brown oil. Trituration with EtOAc/hexane afforded the product as a white solid (3.7 g, 47%): $^1$H-NMR (400 MHz, $d_6$-DMSO)

9.32 (1H, m), 7.11 dt (2H, t, J 8.5, 2.5 Hz), 6.67 (2H, t, J 8.5, 2.5 Hz), 4.02 (2H, s), 3.43 (4H, m), 3.33 (4H, m) and 1.40 (9H, s).

All other starting materials and reagents are commercially available unless otherwise stated.

Example 1

Piperazine-1-carboxylic acid 4-trifluoromethoxy-benzyl ester hydrochloride

Piperazine-1,4-dicarboxylic acid tert-butyl ester 4-trifluoromethoxy-benzyl ester: 652 mg (1.5 mmol) PS-BEMP and 373 mg (1.5 mmol) 4-chlorocarbonyl-piperazine-1-carboxylic acid tert-butyl ester was added to a solution of 192 mg (1.0 mmol) 4-trifluoromethoxybenzyl alcohol in 5 ml acetonitrile. The mixture was heated to reflux for 24 h then cooled to rt, diluted with 5 ml acetonitrile, 666 mg (4.5 mmol) PS-NH2 added and shaken at rt for 16 h. After filtration and evaporation the crude product is purified by flash chromatography on silica gel with hexane/AcOEt 50:50: 180 mg colourless crystalline solid. $^1$H-NMR ($CDCl_3$): 1.45 s, 9H, 3.35–3.55 m, 8H, 5.14 s, 2H, 7.20 d, 2H and 7.40 d, 2H, AB-system.

Piperazine-1-carboxylic acid 4-trifluoromethoxy-benzyl ester hydrochloride: A solution of 174 mg (0.49 mmol) piperazine-1,4-dicarboxylic acid tert-butyl ester 4-trifluoromethoxy-benzyl ester in 4.9 ml 1.5M HCl/Et2O and 0.98 ml abs. MeOH was stirred at rt for 3 h. Evaporation of the reaction mixture provided 189 mg as colourless powder. $^1$H-NMR ($d_6$-DMSO): 3.10 m, 4H and 3.62 m, 4H; 5.13 2, 2H; 7.40 d, 2H and 7.53 d, 2H, AB-system; 9.2 br, 2H. MS (ISP): 305.2 $(M+H)^+$.

In analogy to Example 1 the following carbamates of Examples 2–24 were prepared from the given starting material that is either commercially available or described in the literature:

Example 2

Piperazine-1-carboxylic acid 3,4-difluoro-benzyl ester hydrochloride was prepared from 3,4-difluorobenzyl alcohol; MS (ISP): 257.1 $MH^+$.

Example 3

Piperazine-1-carboxylic acid 4-fluoro-benzyl ester hydrochloride was prepared from 4-fluorobenzyl alcohol; MS (ISP): 239.3 $MH^+$.

Example 4

Piperazine-1-carboxylic acid 4-bromo-benzyl ester hydrochloride was prepared from 4-bromobenzyl alcohol; MS (ISP): 299.1 $MH^+$.

Example 5

Piperazine-1-carboxylic acid 2-trifluoromethoxy-benzyl ester hydrochloride was prepared from 2-trifluoromethoxy-benzyl alcohol; MS (ISP): 305.2 $MH^+$.

Example 6

Piperazine-1-carboxylic acid 2-chloro-5-nitro-benzyl ester hydrochloride was prepared from 2-chloro-5-nitro-benzyl alcohol; MS (ISP): 300.3 $MH^+$.

Example 7

Piperazine-1-carboxylic acid 2-chloro-benzyl ester hydrochloride was prepared from 2-chlorobenzyl alcohol; MS (ISP): 255.1 $MH^+$.

Example 8

Piperazine-1-carboxylic acid biphenyl-4-ylmethyl ester hydrochloride was prepared from 4-biphenylmethanol; MS (ISP): 297.3 $MH^+$.

Example 9

Piperazine-1-carboxylic acid 3-methoxy-benzyl ester hydrochloride was prepared from 3-methoxybenzyl alcohol; MS (ISP): 250.2 $MH^+$.

Example 10

Piperazine-1-carboxylic acid 3-trifluoromethyl-benzyl ester hydrochloride was prepared from 3-(trifluoromethyl)-benzyl alcohol; MS (ISP): 289.2 $MH^+$.

Example 11

Piperazine-1-carboxylic acid 4-trifluoromethyl-benzyl ester hydrochloride was prepared from 4-(trifluoromethyl)-benzyl alcohol; MS (ISP): 289.1 $MH^+$.

Example 12

Piperazine-1-carboxylic acid naphthalen-2-ylmethyl ester hydrochloride was prepared from 2-naphthalenemethanol; MS (ISP): 271.3 $MH^+$.

Example 13

Piperazine-1-carboxylic acid naphthalen-1-ylmethyl ester hydrochloride was prepared from 1-naphthalenemethanol; MS (ISP): 271.3 $MH^+$.

Example 14

Piperazine-1-carboxylic acid 2-methyl-benzyl ester hydrochloride was prepared from 2-methylbenzyl alcohol; MS (ISP): 235.4 $MH^+$.

Example 15

Piperazine-1-carboxylic acid 2,4-dichloro-benzyl ester hydrochloride was prepared from 2,4-dichlorobenzyl alcohol; MS (EI): 288.0 $M^+$.

Example 16

Piperazine-1-carboxylic acid 2,6-dichloro-benzyl ester hydrochloride was prepared from 2,6-dichlorobenzyl alcohol; MS (ISP): 289.1 $MH^+$.

Example 17

Piperazine-1-carboxylic acid 4-tert-butyl-benzyl ester hydrochloride was prepared from 4-tert.-butyl-benzyl alcohol; MS (ISP): 277.3 $MH^+$.

Example 18

Piperazine-1-carboxylic acid 2-fluoro-4-trifluoromethyl-benzyl ester hydrochloride was prepared from 2-fluoro-4-trifluoromethyl-benzyl alcohol; MS (ISP): 307.2 $MH^+$.

Example 19

Piperazine-1-carboxylic acid 2,4-difluoro-benzyl ester hydrochloride was prepared from 2,4-difluorobenzyl alcohol; MS (ISP): 257.1 $MH^+$.

Example 20

Piperazine-1-carboxylic acid 2-chloro-4-fluoro-benzyl ester hydrochloride was prepared from 2-chloro-4-fluorobenzyl alcohol; MS (ISP): 273.2 $MH^+$.

Example 21

Piperazine-1-carboxylic acid 4-fluoro-2-trifluoromethyl-benzyl ester hydrochloride was prepared from 4-fluoro-2-trifluoromethyl-benzyl alcohol; MS (ISP): 307.3 $MH^+$.

Example 22

Piperazine-1-carboxylic acid 4-difluoromethoxy-benzyl ester hydrochloride was prepared from 4-difluoromethoxy-benzyl alcohol; MS (ISP): 287.2 $MH^+$.

Example 23

Piperazine-1-carboxylic acid 2,4-dimethyl-benzyl ester hydrochloride was prepared from 2,4-dimethyl-benzyl alcohol; MS (ISP): 248.2 $MH^+$.

Example 24

Piperazine-1-carboxylic acid cyclohexylmethyl ester hydrochloride was prepared from hydroxymethyl-cyclohexane; MS (EI): 226.3 $M^+$.

Example 25

Piperazine-1-carboxylic acid 2-fluoro-benzyl ester hydrochloride: Piperazine-1,4-dicarboxylic acid tert-butyl ester 2-fluoro-benzyl ester: A solution of 4.47 g N-Boc-piperazine in 40 ml acetonitrile was saturated with dry carbon dioxide gas at rt. To this solution was added dropwise in 5 min. a solution of 8.50 g (28 mmol) terabutylammonium hydrogencarbonate (dried at 50° C. at 0.1 mbar for 1 h) in 30 ml acetonitrile, and then carbon dioxide gas bubbled into the stirred solution at rt for 1 h. Then 2.90 g (20 mmol) 2-fluorobenzyl chloride was added drop-wise within 5 min. After stirring at rt for 3 h the reaction mixture was evaporated, 150 ml of water added and extracted with AcOEt. The organic layer was washed with brine, dried over $Na_2SO_4$ and evaporated. Purification by flash chromatography on silica gel with hexane/AcOEt 50:50 provided 4.29 g piperazine-1,4-dicarboxylic acid tert-butyl ester 2-fluoro-benzyl ester as colourless powder. $^1$H-NMR($CDCl_3$): 1.46 s, 9H; 3.35–3.55 m, 8H; 5.21 s, 2H; 7.02–7.20 m, 2H and 7.27–7.45 m, 2H. MS (EI): 338.1 $M^+$.

Piperazine-1-carboxylic acid 2-fluoro-benzyl ester hydrochloride was prepared in analogy to Example 1. Colourless powder, $^1$H-NMR ($CDCl_3$): 3.18 sbr, 4H and 3.85 sbr, 4H; 5.21 s, 2H; 7.03–7.22 m, 2H and 7.30–7.46 m, 2H; 10.1 br, 2H. MS (ISP): 239.3 $(M+H)^+$.

In analogy to Example 25 the carbamates of Examples 26–31 were be prepared from the given starting material that is either commercially available or described in the literature:

Example 26 cis-2,6-Dimethyl-piperazine-1-carboxylic acid 4-chloro-benzyl ester hydrochloride Prepared in analogy to Example 25 with cis-N-Boc-2,6-dimethyl-piperazine and 4-chloro-benzyl chloride. Colourless powder, $^1$H-NMR ($d_6$-DMSO): 1.30 d 7.2 Hz, 6H; 3.0–3.25 m, 4H and 4.2–4.4 m, 2H; 5.11 s, 2H; 7.35–7.55 AB-system, 4H; 9.5 br, 2H. MS (ISP): 283.1 $(M+H)^+$.

Example 27 cis-2,6-Dimethyl-piperazine-1-carboxylic acid 3-cyano-benzyl ester was prepared from 1-Boc-cis-3,5-dimethyl-piperazine and 3-cyano-benzyl bromide; MS (ISP): 274.3 $MH^+$.

Example 28 cis-2,6-Dimethyl-piperazine-1-carboxylic acid 4-methoxycarbonyl-benzyl ester hydrochloride was prepared from 1-Boc-cis-3,5-dimethyl-piperazine and methyl 4-(bromomethyl)-benzoate; MS (ISP): 307.3 $MH^+$.

Example 29

Piperazine-1-carboxylic acid 4-cyano-benzyl ester hydrochloride was prepared from 4-cyano-benzyl bromide; MS (ISP): 246.3 $MH^+$.

Example 30

Piperazine-1-carboxylic acid 2-trifluoromethyl-benzyl ester hydrochloride was prepared from methanesulfonic acid 2-trifluoromethyl-benzyl ester that was prepared from 2-trifluoromethyl-benzyl alcohol and methanesulfonyl chloride following a text book procedure; MS (ISP): 289.2 $MH^+$.

Example 31

Piperazine-1-carboxylic acid 4-chloro-2-fluoro-benzyl ester hydrochloride was prepared from 4-chloro-2-fluoro-benzyl bromide; $^1$H-NMR ($d_6$-DMSO): 3.07 m, 4H and 3.59m, 4H, piperazine-H; 5.13 s, 2H, $OCH_2$; MS (ISP): 273.2 $MH^+$.

Example 32

Piperazine-1-carbothioic acid S-(4-benzyloxy-benzyl) ester hydrochloride: 4-(4-Benzyloxy-benzylsulfanylcarbonyl)-piperazine-1-carboxylic acid tert-butyl ester: Under argon 84 mg (1.5 mmol) of solid KOH was dissolved at rt in 214 mg (1 mmol) 4-(benzyloxy)-benzyl alcohol and 0.5 ml acetone. Then 76 mg (1.1 mmol) carbon disulfide was added and the mixture thoroughly stirred for 2 h. 323 mg (1.3 mmol) 4-chlorocarbonyl-piperazine-1-carboxylic acid tert-butyl ester was added and the mixture heated at reflux for 8 h. The reaction mixture was cooled to rt, 3 ml of water added and extracted with TBME. The organic phase was washed with water and brine to pH 7, dried over $Na_2SO_4$ and evaporated. Purification of the crude product by preparative HPLC on a PRO C18 column with a $H_2O$/MeCN gradient provided 87 mg 4-(4-benzyloxy-benzylsulfanylcarbonyl)-piperazine-1-carboxylic acid tert-butyl ester as colourless powder. $^1$H-NMR ($CDCl_3$): 1.46 s, 9H; 3.40–3.65 m, 8H; 4.13 s, 2H; 5.04 s, 2H; 6.90 d, 2H and 7.25–7.48 m, 7H.

Piperazine-1-carbothioic acid S-(4-benzyloxy-benzyl) ester hydrochloride: A solution of 86 mg (0.19 mmol) 4-(4-benzyloxy-benzylsulfanylcarbonyl)-piperazine-1-carboxylic acid tert-butyl ester in 2.2 ml 1.5M HCl/$Et_2O$ and 0.45 ml abs. MeOH was stirred at rt for 4 h. Evaporation of the reaction mixture provided 64 mg product as colourless powder. $^1$H-NMR($d_6$-DMSO): 3.03–3.17 m, 4H and 3.58–3.73 m, 4H; 4.09 s, 2H; 5.08 s, 2H; 6.95 d, J=7.5 Hz, 2H and 7.26 d, J=7.5 Hz, 2H (AB-system) and 7.30–7.50 m, 5H; 9.2 br, 2H. MS (ISP): 343.2 $(M+H)^+$.

In analogy to Example 32 the following thiocarbamates of Examples 33–39 were prepared from the given starting material that is either commercially available or described in the literature:

Example 33

Piperazine-1-carbothioic acid S-(4-bromo-benzyl) ester hydrochloride was prepared from 4-bromobenzyl alcohol; $^1$H-NMR ($d_6$-DMSO): 3.10 m, 4H and 3.68 m, 4H, piperazine-H; 4.12 s, 2H, $SCH_2$; MS (ISP): 317.1 $MH^+$.

Example 34

Piperazine-1-carbothioic acid S-(4-trifluoromethoxy-benzyl) ester hydrochloride was prepared from 4-trifluoromethoxy-benzyl alcohol; $^1$H-NMR ($d_6$-DMSO): 3.12 m, 4H and 3.70 m, 4H, piperazine-H; 4.21 s, 2H, $SCH_2$; MS (ISP): 321.3 $MH^+$.

Example 35

Piperazine-1-carbothioic acid S-(4-fluoro-benzyl) ester hydrochloride was prepared from 4-fluoro-benzyl alcohol; $^1$H-NMR ($d_6$-DMSO): 3.10 m, 4H and 3.68 m, 4H, piperazine-H; 4.14 s, 2H, $SCH_2$; MS (ISP): 255.1 $MH^+$.

Example 36

Piperazine-1-carbothioic acid S-(2,4-difluoro-benzyl) ester hydrochloride was prepared from 2,4-difluoro-benzyl alcohol; $^1$H-NMR ($d_6$-DMSO): 3.10 m, 4H and 3.68 m, 4H, piperazine-H; 4.14 s, 2H, $SCH_2$; MS (ISP): 273.2 $MH^+$.

Example 37

Piperazine-1-carbothioic acid S-(4-methoxy-benzyl) ester hydrochloride was prepared from 4-methoxy-benzyl alcohol; $^1$H-NMR ($d_6$-DMSO): 3.10 m, 4H and 3.67 m, 4H, piperazine-H; 3.72 s, 3H, $OCH_3$; 4.09 s, 2H, $SCH_2$; MS (ISP): 267.3 $MH^+$.

Example 38

Piperazine-1-carbothioic acid S-(2,4-dimethyl-benzyl) ester hydrochloride was prepared from 2,4-dimethylbenzyl alcohol; $^1$H-NMR ($d_6$-DMSO): 2.23 s, 3H and 2.27 s, 3H, 2×$CH_3$-aryl; 3.10 m, 4H and 3.66 m, 4H, piperazine-H; 4.10 s, 2H, $SCH_2$; MS (ISP): 265.3 $MH^+$.

Example 39

Piperazine-1-carbothioic acid S-(2-fluoro-4-trifluoromethyl-benzyl) ester hydrochloride was prepared from 2-fluoro-4-trifluoromethyl-benzyl alcohol; $^1$H-NMR ($d_6$-DMSO): 3.10 m, 4H and 3.67 m, 4H, piperazine-H; 4.24 s, 2H, $SCH_2$; MS (ISP): 323.3 $MH^+$.

Example 40

Piperazine-1-carbothioic acid S-[4-(4-fluoro-benzyloxy)-benzyl] ester hydrochloride: 4-(4-Fluoro-benzyloxy)-phenyl-methanethiol in analogy to S. Vetter, Synth. Commun. 28, 3219 (1998): A mixture of 6.00 (26 mmol) 4-(4-fluorobenzyloxy)-benzyl alcohol and 3.93 g (52 mmol) thiourea was dissolved at 50° C. in water/acetone 1:1.5. To this solution 7.75 ml 5N HCl was added dropwise and the mixture stirred at 50° C. for 16 h. Then the solution was cooled and extracted quickly twice with $Et_2O$, the aqueous layer made alkaline by addition of 3.1 g (78 mmol) NaOH pellets and heated to reflux for 3 h. Acidification of the reaction mixture at rt with 5N HCl, extraction with AcOEt, drying with $Na_2SO_4$ and evaporation furnished 6.25 g 4-(4-fluoro-benzyloxy)-phenyl-methanethiol as a colourless powder: mp. 77–80° C. $^1$H-NMR ($d_6$-DMSO): 2.77 t, J=7.5 Hz, 1H; 3.68 d, J=7.5 Hz, 2H; 5.06 s, 2H; 6.94 d, 2H and 7.18–7.32 m, 4H and 7.45–7.58 m, 2H.

4-[4-(4-Fluoro-benzyloxy)-benzylsulfanylcarbonyl]-piperazine-1-carboxylic acid tert-butyl ester: 5.84 g (23.5 mmol) 4-chlorocarbonyl-piperazine-1-carboxylic acid tert-butyl ester were added to a solution of 6.0 g (24.2 mmol) 4-(4-fluoro-benzyloxy)-phenyl-methanethiol in 14.6 ml pyridine. The solution was heated to 100° C. for 3.5 h, then cooled to rt, 10 ml of water added and the volume reduced to a third. The resulting precipitate is collected, washed with water and dried. The crude product is re-crystallized from hexane/AcOEt. Flash chromatography on silica gel provided 4.90 g 4-[4-(4-fluoro-benzyloxy)-benzylsulfanylcarbonyl]-piperazine-1-carboxylic acid tert-butyl ester as colourless powder, mp: 123–124° C. $^1$H-NMR ($CDCl_3$): 1.46 s, 9H; 3.38–3.60 m, 8H; 4.13 s, 2H; 5.00 s, 2H; 6.89 d, 2H, 7.06 t, 2H, 7.28 d, 2H and 7.40 dd, 2H.

Piperazine-1-carbothioic acid S-[4-(4-fluoro-benzyloxy)-benzyl] ester hydrochloride: A solution of 4.89 g (10.6 mmol) 4-[4-(4-fluoro-benzyloxy)-benzylsulfanylcarbonyl]-piperazine-1-carboxylic acid tert-butyl ester in 120.6 ml 1.5M HCl/$Et_2O$ and 24.1 ml abs. MeOH was stirred at rt for 6 h. Evaporation of the reaction mixture provided 3.96 g piperazine-1-carbothioic acid S-[4-(4-fluoro-benzyloxy)-benzyl] ester hydrochloride as colourless powder, mp. 169–169.5° C. $^1$H-NMR($d_6$-DMSO): 3.05 m, 4H and 3.58–3.75 m, 4H; 4.09 s, 2H; 5.06 s, 2H; 6.94 d, 2H, 7.17–7.30 m, 4H and 7.43–7.55 m, 2H; 9.2 br, 2H. MS (ISP): 361.2 $(M+H)^+$.

Example 41

Piperazine-1-carboxylic acid 4-benzyloxy-benzyl ester (RS)-Carbonic acid 4-benzyloxy-benzyl ester 1-chloroethyl ester: A solution of 1.07 g (5.0 mmol) 4-benzyloxy-benzyl alcohol and 0.786 g (5.5 mmol) 1-chloroethyl chloroformate in 25 ml $CH_2Cl_2$ is cooled to 0° C. and 0.435 g (5.5 mmol) pyridine added. After stirring at rt for 2 h the reaction mixture is quenched with 1N HCl, the organic phase separated and washed with sat. $NaHCO_3$ solution and brine, dried over $Na_2SO_4$ and evaporated: 1.58 g (98%) (RS)-carbonic acid 4-benzyloxy-benzyl ester 1-chloro-ethyl ester as light yellow oil. $^1$H-NMR ($CDCl_3$): 1.81 d, J=6 Hz, 3H; 5.07 s, 2H; 5.14 and 5.17, AB-system J=15 Hz, 2H; 6.43 q, J=6 Hz, 1H; 6.97 d, J=8.5 Hz, 2H and 7.30–7.45 m, 7H.

Piperazine-1,4-dicarboxylic acid 4-benzyloxy-benzyl ester 9H-fluoren-9-ylmethyl ester: A solution of 1.47 g (4.7 mmol) N-Fmoc-piperazine (obtained from N-Fmoc-piperazine hydrobromide by treatment with aqueous $NaHCO_3$ and extraction with TBME, drying the organic layer over $Na_2SO_4$ and evaporation under reduced pressure at <30° C.) in 18 ml $CH_2Cl_2$ at 0° C. was added dropwise to a solution of 1.51 g (4.7 mmol) (RS)-carbonic acid 4-benzyloxy-benzyl ester 1-chloro-ethyl ester in 57 ml of $CH_2Cl_2$. The reaction is slightly exothermic and a colourless precipitate is formed. After 1 h at 0° C. the mixture was allowed to warm to rt and stirred for further 62 h. Then the reaction is quenched with 2.35 ml 4M $K_2CO_3$, filtered over a plug of $Na_2SO_4$ and evaporated. The crude product (2.67 g) was purified by flash-chromatography on silica gel with hexane/AcOEt 50:50 as eluent: 1.54 g (60%) RO-72-0160/000 as yellow solid. IR (Nujol): 1699 $cm^{-1}$. $^1$H-NMR ($CDCl_3$): 3.25–3.60 br, 8H; 4.23 t, J=6.4 Hz, 1H; 4.48 d, J=6.4 Hz, 2H; 5.06 s and 5.07 s, 4H; 6.97 d, J=8.4 Hz, 2H, 7.26–7.45, m 11H, 7.55 d, J=7.6 Hz, 2H and 7.76 d, J=7.6 Hz, 2H. MS (ISP): 566.4 $(M+NH_4)^+$; 571.4 $(M+Na)^+$.

Piperazine-1-carboxylic acid 4-benzyloxy-benzyl ester: A solution of 274 mg (0.5 mmol) piperazine-1,4-dicarboxylic acid 4-benzyloxy-benzyl ester 9H-fluoren-9-ylmethyl ester in 13 ml morpholine was stirred at rt for 1 h. Then 23 ml of chilled water was added, the suspension filtered and the filtrate extracted with TBME. The organic layer was washed with water, brine, dried over $Na_2SO_4$ and evaporated: 54 mg piperazine-1-carboxylic acid 4-benzyloxy-benzyl ester as light yellow, waxy solid. MIR: 3300 $cm^{-1}$, 1688 $cm^{-1}$. $^1$H-NMR ($CDCl_3$): 1.77 br, 1H; 2.75–2.90 m, 4H and 3.40–3.50 m, 4H; 5.06 s and 5.07 s, 4H; 6.96 d, J=8.8 Hz, 2H and 7.28–7.44 m, 7H. MS (ISP): 327.3 $(M+H)^+$.

In analogy to Example 41 the following carbamates of Examples 42–45 were prepared from the given starting material that is either commercially available or described in the literature.

Example 42

Piperazine-1-carboxylic acid 4-(4-fluoro-benzyloxy)-benzyl ester (RS)-Carbonic acid 1-chloro-ethyl ester 4-(4-fluoro-benzyloxy)-benzyl ester: Prepared in analogy to (RS)-carbonic acid 4-benzyloxy-benzyl ester 1-chloro-ethyl ester (Example 41) from 4-(4-fluoro-benzyloxy)-benzyl alcohol and 1-chloroethyl chloroformate: light yellow oil. $^1$H-NMR ($CDCl_3$): 1.81 d, J=5.5 Hz, 3H; 5.03 s, 2H; 5.13 and 5.18 J=5.5 Hz, AB-system, 2H; 6.43 q, 1H; 6.95 d, J=8.4 Hz, 2H, 7.07 t J=8.4 Hz, 2H, 7.28–7.45 m, 4H.

Piperazine-1,4-dicarboxylic acid 9H-fluoren-9-ylmethyl ester 4-(4-fluoro-benzyloxy)-benzyl ester: Prepared in analogy to piperazine-1,4-dicarboxylic acid 4-benzyloxy-benzyl ester 9H-fluoren-9-ylmethyl ester (Example 41) from (RS)-carbonic acid 1-chloro-ethyl ester 4-(4-fluoro-benzyloxy)-benzyl ester) and N-Fmoc-piperazine: yellow solid. $^1$H-NMR ($CDCl_3$): 3.3–3.6 m, 8H; 4.23 t, J=6 Hz, 1H; 4.48 d, J=6 Hz, 2H; 5.03 s, 2H; 5.08 s, 2H; 6.95 d, J=8.5 Hz, 2H, 7.08 t, J=8.5 Hz, 2H, 7.25–7.46 m, 8H, 7.55 d, J=7 Hz, 2H and 7.77 d, J=7 Hz, 2H.

Piperazine-1-carboxylic acid 4-(4-fluoro-benzyloxy)-benzyl ester: Prepared in analogy to piperazine-1-carboxylic acid 4-benzyloxy-benzyl ester (Example 41) from piperazine-1,4-dicarboxylic acid 9H-fluoren-9-ylmethyl ester 4-(4-fluoro-benzyloxy)-benzyl ester and morpholine: colourless, waxy solid: IR (Nujol): 3341 $cm^{-1}$, 1689 $cm^{-1}$. $^1$H-NMR ($CDCl_3$): 1.75 br, 1H; 2.85–2.90 m, 4H and 3.40–3.55 m, 4H; 5.02 s, 2H; 5.07 s, 2H; 6.94 d, J=8.4 Hz, 2H, 7.07 t, J=8.8 Hz, 2H, 7.30 d, J=8.4 Hz, 2H and 7.38–7.42 m, 2H. MS (EI): 344.3 $M^+$.

Example 43

Piperazine-1-carboxylic acid 4-methoxy-benzyl ester hydrochloride was Prepared from 4-methoxy-benzyl alcohol via the following intermediates (RS)-Carbonic acid 1-chloro-ethyl ester 4-methoxy-benzyl ester: $^1$H-NMR ($CDCl_3$): 1.81 d, J=8.2 Hz, 3H; 3.81 s, 3H; 5.14 and 5.18 AB-system, J=16 Hz, 2H; 6.42 q, J=8.2 Hz, 1H; 6.90 d, J=8 Hz, 2H and 7.36 d, J=8 Hz, 2H. MS (EI): 244.1 $M^+$.

Piperazine-1,4-dicarboxylic acid 9H-fluoren-9-ylmethyl ester 4-methoxy-benzyl ester: $^1$H-NMR ($CDCl_3$): 3.32–3.58 br, 8H; 3,81 s, 3H; 4.24 t, J=6 Hz, 1H; 4.58 d, J=6 Hz, 2H; 5.07 s, 2H; 6.92 d, J=8 Hz, 2H, 7.54–7.46 m, 6H, 7.54 d, J=8 Hz, 2H, 7.78 d, J=8 Hz, 2H.

Piperazine-1-carboxylic acid 4-methoxy-benzyl ester hydrochloride: Deprotection with morpholine led to piperazine-1-carboxylic acid 4-methoxy-benzyl ester. The hydrochloride was prepared by addition of $HCl/Et_2O$ to a solution of the free base in $Et_2O$ followed by evaporation. $^1$H-NMR (d6-DMSO): 3.10 m, 4H and 3.60 m, 4H, piperazine-H; 5.02 s, 2H. MS (ISP): 251.2 $MH^+$.

Example 44

Piperazine-1-carboxylic acid benzhydryl ester was prepared from diphenyl carbinol via he following intermediates (RS)-Carbonic acid benzhydryl ester 1-chloro-ethyl ester: $^1$H-NMR ($CDCl_3$): 1.83 d, J=5.8 Hz, 3H; 6.41 q, J=5.8 Hz, 1H; 6.75 s, 1H; 7.25–7.43 m, 10H.

Piperazine-1,4-dicarboxylic acid benzhydryl ester 9H-fluoren-9-ylmethyl ester: $^1$H-NMR ($CDCl_3$): 3.32–3.68 br, 8H; 4.24 t, J=6 Hz, 1H; 4.48 d, J=6 Hz, 2H; 6.82 s, 1H; 7.25–7.44 m, 14H and 7.56 d, J=8 Hz, 2H and 7.78 d, J=8 Hz, 2H.

Piperazine-1-carboxylic acid benzhydryl ester: $^1$H-NMR ($CDCl_3$): 1.70 br, 1H; 2.80–2.85 m, 4H and 3.40–3.70 m, 4H, piperazine-H; 6.82 s, 1H; 7.25–7.35 m, 10H. MS (ISP): 297.3 $MH^+$.

Example 45

(RS)-Piperazine-1-carboxylic acid 1-phenyl-ethyl ester was prepared from (RS)-1-phenylethanol via the following intermediates (RS)-Carbonic acid 1-chloro-ethyl ester 1-phenyl-ethyl ester: $^1$H-NMR ($CDCl_3$): 1.62 d, J=6.5 Hz and 1.64 d, J=6.5 Hz, 3H; 1.79 d, J=5.8 Hz and 1.64 d, J=5.8 Hz, 3H; 5.77 q, J=6.5 Hz and 5.80 q, J=6.5 Hz, 1H; 6.37 q, J=5.8 Hz and 6.41 q, J=5.8 Hz, 1H; 7.37 m, 5H.

(RS)-Piperazine-1,4-dicarboxylic acid 9H-fluoren-9-ylmethyl ester 1-phenyl-ethyl ester: $^1$H-NMR ($CDCl_3$): 1.56 d, J=6.5 Hz, 3H; 3.32–3.58 br, 8H; 4.24 t, J=6 Hz, 1H; 4.68 d, J=6 Hz, 2H; 5.83 d, J=6.5 Hz, 1H; 7.25–7.44 m, 9H and 7.56 d, J=8 Hz, 2H and 7.78 d, J=8 Hz, 2H.

(RS)-Piperazine-1-carboxylic acid 1-phenyl-ethyl ester: $^1$H-NMR ($CDCl_3$): 1.54 d, J=4 Hz, 3H; 1.68 br, 1H; 2.75–2.85 m, 4H and 3.40–3.55 m, 4H, piperazine-H; 5.82 q, J=4 Hz, 1H; 7.25–7.38 m, 5H. MS (EI): 234.2 $M^+$.

Example 46

Piperazine-1-carboxylic acid phenethyl ester

Phenethyl alcohol (2 eq), triethylamine (3 eq) and pyridine (1 eq) was added to a solution of 4-chlorocarbonyl-piperazine-1-carboxylic acid tert-butyl ester in dichloromethane (30 vol.) and the mixture was shaken at 25° C. for 6 days. The mixture was evaporated, and the resultant crude material purified by preparative HPLC [C18, 10 mM aqueous $NH_4OAc$ solution:MeOH] to afford the intermediate product, which was used immediately in the next step.

A solution of HCl in dioxane (4 M, 10 eq) was added to a solution of the above intermediate in methanol (50 volumes) and the mixture was shaken for 16 h. Evaporation to dryness afforded the desired product.

$^1$H-NMR (400 MHz, $d_6$-DMSO): 2.90 (2H, t, J=6.5 Hz), 2.99–3.06 (4H, m), 3.52–3.59 (4H, m), 4.22 (2H, t, J=6.5 Hz), 7.19–7.34 (5H, m) and 9.29–9.43 (2H, br s); HPLC: [XTERRA; methanol-10 mM aqueous $NH_4OAc$ (40:60); 2 mL/min; 210 nm] 100% (0.98 min).

Example 47 cis-2,6-Dimethylpiperazine-1-carboxylic acid 5-[2-(3-chlorobenzyloxy)]pyridyl-methyl ester fumarate cis-2,6-Dimethylpiperazine-1,4-dicarboxylic acid 5-(2-chloropyridyl)-methyl ester tert-butyl ester: A solution of 2-chloro-5-(hydroxymethyl)pyridine (2.6 g, 18 mmol), 1-tert-butoxycarbonyl-2,6-dimethyl-4-chlorocarbonylpiperazine (3.8 g, 14 mmol), pyridine (1.5 mL, 19 mmol) and triethylamine (7.6 mL, 52 mmol) in dichloromethane (100 mL) was stirred for 96 h. The mixture was concentrated in vacuo then partitioned between water (100 mL) and ethyl acetate (3×50 mL). The combined organic extracts were washed with water and brine, then dried over sodium sulfate, concentrated in vacuo and purified by flash column chromatography [$SiO_2$; isohexane-ethyl acetate (4:1)] to give the product as a white solid (1.7 g, 32%), m.p. 75–76° C. $^1$H-NMR (400 MHz, $CDCl_3$): 8.40 (1H, d, J=2.5 Hz), 7.67 (1H, dd, J=2.5, 8 Hz), 7.33 (1H, d, J=8 Hz), 5.14 (2H, s), 4.23–4.14 (2H, m), 4.04–3.82 (2H, m), 3.04–2.86 (2H, m), 1.47 (9H, s) and 1.23 (6H, d, J=7 Hz).

cis-2,6-Dimethylpiperazine-1,4-dicarboxylic acid 5-[2-(3-chlorobenzyloxy)]pyridyl-methyl ester tert-butyl ester: Tris-[2-(2-methoxyethoxy)ethyl]amine (0.02 g, 0.007 mmol) was added to a stirred mixture of cis-2,6-Dimethylpiperazine-1,4-dicarboxylic acid 5-(2-chloropyridyl)methyl ester tert-butyl ester (0.25 g, 0.7 mmol), 3-chlorobenzyl alcohol (0.14 g, 1.0 mmol), potassium carbonate (0.09 g, 0.7 mmol) and powdered potassium hydroxide (85%, 0.17 g, 2.6 mmol) in toluene (10 mL). The mixture was heated to 120° C., stirred for 4 h, cooled to room temperature, poured into water (20 mL) and extracted with ether (3×30 mL). The combined organic extracts were washed with water and brine, then dried over sodium sulfate, concentrated in vacuo and purified by flash column chromatography [$SiO_2$; isohexane-ethyl acetate (9:1) to (3:1)] to give the product as a viscous oil (0.13 g, 40%). $^1$H-NMR (400 MHz, $CDCl_3$): 8.16 (1H, d, J=2.5 Hz), 7.63 (1H, dd, J=2.5, 8.5 Hz), 7.45 (1H, s), 7.34–7.27 (3H, m), 6.81 (1H, d, J=8.5 Hz), 5.36 (2H, s), 5.08 (2H, s), 4.22–4.14 (2H, m), 4.05–3.80 (2H, m), 3.08–2.84 (2H, m), 1.47 (9H, s) and 1.22 (6H, d, J=7 Hz); HPLC [Xterra, 2.0 mL/min; methanol-10 mM aqueous ammonium acetate solution (50:50) to (80:20) over 5 min then (80:20)] 97% (7.81 min).

cis-2,6-Dimethylpiperazine-1-carboxylic acid 5-[2-(3-chlorobenzyloxy)]pyridyl-methyl ester fumarate: a solution of hydrogen chloride in dioxan (4 M, 0.61 mL, 2.4 mmol) was added drop-wise to a stirred solution of cis-2,6-Dimethylpiperazine-1,4-dicarboxylic acid 5-[2-(3-chlorobenzyloxy)]pyridyl-methyl ester tert-butyl ester (0.12 g, 0.24 mmol) in methanol (5 mL). The mixture was stirred for 18 h then concentrated in vacuo. The residue was partitioned between ether (2×10 mL) and aqueous sodium hydroxide solution (2 M, 10 mL). The combined organic layers were washed with water and brine then dried over sodium sulfate, concentrated in vacuo, dissolved in warm 2-propanol (1 mL) and added drop-wise to a stirred solution of fumaric acid (0.033 g, 0.28 mmol) in warm 2-propanol (1 mL). The mixture was cooled to 0° C., stirred for 30 min then filtered. The filter-cake was washed with 2-propanol and ether then dried in vacuo to give the product as a white solid (0.071 g, 57%), m.p. 172° C. (dec.). $^1$H-NMR (400 MHz, $d_6$-DMSO): 8.18 (1H, d, J=2.5 Hz), 7.76 (1H, dd, J=2.5, 8.5 Hz), 7.50 (1H, s), 7.42–7.36 (3H, m), 6.93 (1H, d, J=8.5 Hz), 6.59 (2H, s), 5.37 (2H, s), 5.04 (2H, s), 4.01–3.93 (2H, m), 2.77 (2H, d, J=12 Hz), 2.70 (2H, dd, J 4, 12 Hz) and 1.18 (6H, d, J=7 Hz).

Example 48

Piperazine-1-carboxylic acid 5-[2-(3-chlorobenzyloxy)]pyridyl-methyl ester fumarate 6-(3-Chlorobenzyloxy)nicotinic acid: 6-chloronicotinic acid (1.0 g, 6.3 mmol)) was added portion-wise over 30 min to a stirred suspension of sodium hydride (60%, 0.76 g, 19 mmol) in toluene (10 mL. The mixture was stirred for 30 min then cooled to 0° C. A solution of 3-chloro-benzyl alcohol (0.69 g, 6.4 mmol) in toluene (5 mL) was added drop-wise over 10 min. The mixture was warmed to room temperature, DMF (20 mL) was added and the mixture was heated to 95° C. and stirred for 18 h. The mixture was cooled to room temperature then poured into water (30 mL). The aqueous mixture was acidified to pH 2 and extracted with ethyl acetate (2×30 mL). The combined organic extracts were washed with water and brine, then dried over sodium sulfate and concentrated in vacuo to give a yellow solid (2.36 g). The residue was re-crystallised [2-propanol-water, (2:1)] to give the product as a white solid (0.85 g, 51%), m.p. 158° C. (dec.). $^1$H-NMR (400 MHz, $CDCl_3$): 8.93 (1H, d, J=2.5 Hz), 8.24 (1H, dd, J=2.5, 8.5 Hz), 7.46 (1H, s), 7.35–7.29 (3H, m), 6.87 (1H, dd, J=1, 8.5 Hz) and 5.45 (2H, s).

2-(3-Chlorobenzyloxy)-5-(hydroxymethyl)pyridine: 6-(3-chlorobenzyloxy)nicotinic acid (0.60 g, 2.3 mmol) was added portionwise to a stirred suspension of lithium aluminium hydride (0.14 g, 3.7 mmol) in THF (10 mL) at 0° C. under Ar. The mixture was warmed to room temperature, stirred for 2 h then cooled to 0° C. Saturated aqueous sodium potassium tartrate solution (1 mL) was added dropwise followed by sodium sulfate decahydrate (2 g). The mixture was diluted with ether (30 mL), stirred for 1 h then filtered through kieselguhr. The filter-cake was washed with ether (10 mL); the combined filtrates were concentrated in vacuo and purified by flash column chromatography [$SiO_2$; isohexane-ethyl acetate (4:1) to (1:1)] to give the product as a viscous oil (0.25 g, 44%). $^1$H-NMR (400 MHz, $CDCl_3$): 8.11 (1H, d, J=2.5 Hz), 7.63 (1H, dd, J=2.5, 8.5 Hz), 7.45 (1H, s), 7.33–7.25 (3H, m), 6.82 (1H, d, J=8.5 Hz), 5.35 (2H, s), 4.62 (2H, d, J=4 Hz) and 1.87 (1H, t, J=4 Hz, —OH). HPLC: [Xterra, 2.0 mL/min; methanol-10 mM aqueous ammonium acetate solution (50:50) to (80:20) over 5 min then (80:20)] 98% (3.95 min).

Piperazine-1,4-dicarboxylic acid 5-[2-(3-chlorobenzyloxy)]pyridyl-methyl ester tert-butyl ester: a solution of 2-(3-chlorobenzyloxy)-5-(hydroxymethyl)pyridine (0.22 g, 0.9 mmol) in DMF (1 mL) was added drop-wise to a stirred suspension of sodium hydride (60%, 0.042 g, 1.1 mmol) in DMF (2 mL). The mixture was stirred for 30 min then a solution of 1-tert-butoxycarbonyl-4-chlorocarbonylpiperazine (0.22 g, 0.9 mmol) in DMF (1 mL) was added. The mixture was stirred for 18 h then poured into water (10 mL) and extracted with ether (2×10 mL). The combined organic extracts were washed with water and brine, then dried over sodium sulfate, concentrated in vacuo and purified by flash column chromatography [$SiO_2$; isohexane-ethyl acetate (9:1) to (3:1)] to give the product as a viscous oil (0.17 g, 41%). $^1$H-NMR (400 MHz, $CDCl_3$): 8.16 (1H, d, J=2.5 Hz), 7.63 (1H, dd, J=2.5, 8.5 Hz), 7.45 (1H, s), 7.34–7.26 (3H, m), 6.81 (1H, d, J=8.5 Hz), 5.36 (2H, s), 5.08 (2H, s), 3.48–3.36 (8H, m) and 1.46 (9H, s). HPLC: [Xterra, 2.0 mL/min; methanol-10 mM aqueous ammonium acetate solution (50:50) to (80:20) over 5 min then (80:20)] 97% (7.35 min).

Piperazine-1-carboxylic acid 5-[2-(3-chlorobenzyloxy)] pyridyl-methyl ester fumarate: a solution of hydrogen chloride in dioxan (4 M, 0.9 mL, 3.6 mmol) was added drop-wise to a stirred solution of piperazine-1,4-dicarboxylic acid 5-[2-(3-chlorobenzyloxy)]pyridyl-methyl ester tert-butyl ester (0.16 g, 0.35 mmol) in methanol (5 mL). The mixture was stirred for 18 h then concentrated in vacuo. The residue was partitioned between ether (2×10 mL) and aqueous sodium hydroxide solution (2 M, 10 mL). The combined organic layers were washed with water and brine then dried over sodium sulfate, concentrated in vacuo, dissolved in warm 2-propanol (2 mL) and added dropwise to a stirred solution of fumaric acid (0.047 g, 0.41 mmol) in warm 2-propanol (2 mL). The mixture was cooled to 0° C., stirred for 30 min then filtered. The filter-cake was washed with 2-propanol and ether then dried in vacuo to give the product as a white solid (0.089 g, 54%), m.p. 148° C. (dec.). $^1$H-NMR (400 MHz, $d_6$-DMSO): 8.19 (1H, d, J=2.5 Hz), 7.77 (1H, dd, J=2.5, 8.5 Hz), 7.50 (1H, s), 7.42–7.36 (3H, m), 6.92 (1H, d, J=8.5 Hz), 6.52 (2H, s), 5.36 (2H, s), 5.04 (2H, s), 3.45–3.40 (4H, m) and 2.86–2.80 (4H, m).

Example 49 cis-2,6-Dimethylpiperazine-1-carboxylic acid 2-(2-thienyl)ethyl ester 2-(2-thienyl)ethanol (2 eq), triethylamine (3 eq) and pyridine (1 eq) was added to a solution of cis-4-chlorocarbonyl-2,6-dimethyl-piperazine-1-carboxylic acid tert-butyl ester in dichloromethane (30 vol.) and the mixture was shaken at 25° C. for 6 days. The mixture was evaporated, and the resultant crude material purified by preparative HPLC [C18, 10 mM aqueous $NH_4OAc$ solution:MeOH] to afford the intermediate product, which was used immediately in the next step.

A solution of HCl in dioxane (4 M, 10 eq) was added to a solution of the above intermediate in methanol (50 volumes) and the mixture was shaken for 16 h. Evaporation to dryness afforded the desired product. HPLC: [XTERRA; methanol-10 mM aqueous $NH_4OAc$ (60:46); 2 mL/min; 210 nm] 94.5% (0.83 min); MS(ISP): 269 $MH^+$.

cis-4-chlorocarbonyl-2,6-dimethyl-piperazine-1-carboxylic acid tert-butyl ester was prepared in analogy to 4-chlorocarbonyl-piperazine-1-carboxylic acid tert-butyl ester from cis-2,6-dimethylpiperazine-1-carboxylic acid tert-butyl ester (A. Muehlebach, P. Pino, Helv. Chim. Acta 73, 839 (1990)) by a modified procedure of Rhone-Poulenc DE 25 50 111 (Rhone-Poulenc).

Example 50 cis-2,6-Dimethylpiperazine-1-carboxylic acid 2-fluorobenzyl ester 2-fluorobenzyl alcohol (2 eq), triethylamine (3 eq) and pyridine (1 eq) was added to a solution of cis-4-chlorocarbonyl-2,6-dimethyl-piperazine-1-carboxylic acid tert-butyl ester in dichloromethane (30 vol.) and the mixture was shaken at 25° C. for 6 days. The mixture was evaporated, and the resultant crude material purified by preparative HPLC [C18, 10 mM aqueous $NH_4OAc$ solution:MeOH] to afford the intermediate product, which was used immediately in the next step.

A solution of HCl in dioxane (4 M, 10 eq) was added to a solution of the above intermediate in methanol (50 volumes) and the mixture was shaken for 16 h. Evaporation to dryness afforded the desired product. HPLC: [XTERRA; methanol-10 mM aqueous $NH_4OAc$ (60:40); 2 mL/min; 210 nm] 96.8% (0.88 min); MS (ISP): 267 $MH^+$.

cis-4-chlorocarbonyl-2,6-dimethyl-piperazine-1-carboxylic acid tert-butyl ester was prepared in analogy to 4-chlorocarbonyl-piperazine-1-carboxylic acid tert-butyl ester from cis-2,6-dimethylpiperazine-1-carboxylic acid tert-butyl ester (A. Muehlebach, P. Pino, Helv. Chim. Acta 73, 839 (1990)) by a modified procedure of Rhone-Poulenc DE 25 50 111 (Rhone-Poulenc).

Example 51

Piperazine-1-carbothioic acid S-[4-(3-nitrobenzyl)oxy]benzyl ester

Piperazine-1-carbothioic acid S-[4-(3-nitrobenzyl)oxy] benzyl ester: A mixture [(4-tert-butyl-dimethylsilyloxy)benzylsulfanylcarbonyl]-piperazine-4-carboxylic acid tert-butyl ester (0.05 g), 3-nitrobenzyl bromide (0.028 g), cesium fluoride (0.033 g) and DMF (1 mL) was shaken for 48 h then partitioned between water (2 mL) and dichloromethane (2 mL). The separated organic layer was concentrated in vacuo then suspended in trifluoroacetic acid-dichloromethane (1:1, 1 mL) and shaken for 18 h. The mixture was concentrated in vacuo and purified by preparative HPLC [C18, 10 mM aqueous $NH_4OAc$ solution:MeOH] to afford the product (0.011 g, 25%). HPLC: [Xterra, 2.0 mL/min; methanol-10 mM aqueous ammonium acetate solution (50:50) to (80:20) over 5 min then (80:20)] 98% (5.1 min); MS (ISP): 387 $MH^+$.

Example 52

Piperazine-1-carboxylic acid 3-(2-phenylethoxy)-benzyl ester hydrochloride

Piperazine-1,4-dicarboxylic acid (3-tert-butyldimethylsilyloxy)benzyl ester tert-butyl ester: A solution of 3-tert-butyldimethylsilyloxybenzyl alcohol (Tetrahedron Lett. 26, 681 (1985)) (5.0 g), triethylamine (8.7 mL), pyridine (1.65 mL) and 4-chlorocarbonyl-piperazine-1-carboxylic acid tert-butyl ester (5.1 g) in dichloromethane (200 mL) was stirred for 96 h. 4-Dimethylaminopyridine (0.20 g) was added and the mixture was heated to reflux for 4 h. The mixture was cooled to room temperature, washed with water (100 mL), brine (100 mL), dried over magnesium sulfate and concentrated in vacuo. The residue was purified by column chromatography [$SiO_2$; dichloromethane, isopropyl ether: (100:0) to (80:20)] to give the product as a yellow oil (3.8 g, 41%). $^1$H-NMR (400 MHz, $CDCl_3$): 0.19 (6H, s), 0.98 (9H, s), 1.46 (9H, s), 3.36–3.43 (4H, m), 3.44–3.50 (4H, m), 5.08 (2H, s), 6.78 (1H, dd, J=2.5, 8 Hz), 6.82 (1H, t, J=2 Hz), 6.92 (1H, d, J=8 Hz) and 7.20 (1H, t, J=8 Hz).

Piperazine-1,4-dicarboxylic acid (3-hydroxy)benzyl ester tert-butyl ester: a solution of tetrabutylammonium fluoride in THF (1 M, 4.4 mL, 4.4 mmol) and glacial acetic acid (0.76 mL, 13.3 mmol) were added sequentially to a stirred solution of piperazine-1,4-dicarboxylic acid (3-tert-butyldimethylsilyloxy)benzyl ester tert-butyl ester (0.50 g, 1.1 mmol) in anhydrous THF (10 mL) at 0° C. The mixture was stirred for 1 h then poured into water (40 mL) and extracted with ethyl acetate (3×20 mL). The combined organic extracts were washed with water (3×25 mL), saturated aqueous sodium hydrogencarbonate solution (25 mL) and brine (25 mL) then dried over magnesium sulfate and concentrated in vacuo to give the product as a colourless oil which solidified on standing (0.38 g, 100%). $^1$H-NMR (400 MHz, $CDCl_3$): 1.46 (9H, s), 3.38–3.44 (4H, m), 3.45–3.50 (4H, m), 5.09 (2H, s), 6.79 (1H, dd, J 2.5, 8 Hz), 6.83 (1H, m, OH), 6.90 (1H, d, J=8 Hz), 7.22 (1H, t, J=8 Hz) and 7.26 (1H, s). HPLC [Xterra, 2.0 mL/min; methanol-10 mM aqueous ammonium acetate solution (50:50) to (80:20) over 5 min then (80:20)] 100% (3.59 min).

Piperazine-1,4-dicarboxylic acid 3-(2-phenylethoxy)benzyl ester tert-butyl ester: potassium carbonate (0.072 g, 0.52 mmol) was added to a solution of piperazine-1,4-dicarboxylic acid (3-hydroxy)benzyl ester tert-butyl ester (0.16 g, 0.48 mmol) in acetone (5 mL) at 0° C. and the reaction mixture was stirred at 0° C. for 30 min. (2-Bromoethyl)-benzene (0.097 g, 0.52 mmol) was added and the reaction mixture was allowed to warm to room temperature and then heated under reflux for 24 h. After cooling, the reaction mixture was concentrated in vacuo and the residue was partitioned between water (20 mL) and ethyl acetate (20 mL). The organic phase was separated, washed with saturated brine (25 mL), dried ($MgSO_4$) and concentrated in vacuo to give an oil which was purified by column chromatography [$SiO_2$; heptane-ethyl acetate (3:1)] to yield the title compound (0.10 g, 48%) as a colourless oil. $^1$H-NMR (400 MHz, $CDCl_3$): 1.46 (9H, s), 3.10 (2H, t, J=7.0 Hz), 3.40 (4H, m), 3.46 (4H, m), 4.18 (2H, t, J=7.0 Hz), 5.09 (2H, s), 6.84 (1H, m), 6.88 (1H, m), 6.91 (1H, m) and 7.22–7.34 (6H, m).

Piperazine-1-carboxylic acid 3-(2-phenylethoxy)-benzyl ester hydrochloride: 4M HCl in 1,4-dioxane (2.3 mL, 9.2 mmol) was added to a solution of piperazine-1,4-dicarboxylic acid 3-(2-phenylethoxy)benzyl ester tert-butyl ester (0.10 g, 0.23 mmol) in methanol (2 mL) and ether (2 mL) and the solution was left to stand with occasional swirling at room temperature for 3 h. The solution was concentrated in vacuo and the residue was triturated with ether to yield the title compound (0.08 g, 93%) as a white solid. $^1$H-NMR (400 MHz, $d_6$-DMSO): 3.03 (2H, t, J=6.8 Hz), 3.08 (4H, m), 3.61 (4H, m), 4.19 (2H, t, J=7.0 Hz), 5.06 (2H, s), 6.88–6.94 (3H, m), 7.20–7.33 (6H, m) and 9.19 (2H, br s).

Example 53

3-[2-(3-Chlorophenyl)ethyl]oxybenzylpiperazine-1-carboxylate hydrochloride

3-[2-(3-Chlorophenyl)ethyl]oxybenzyl-4-tert-butoxycarbonylpiperazine-1-carboxylate was prepared from piperazine-1,4-dicarboxylic acid (3-hydroxy)benzyl ester tert-butyl ester and (2-bromoethyl)-3-chlorobenzene using the method described for Example 52 to yield the product (0.24 g, 85%) as a colourless oil; $^1$H NMR (400 MHz, $CDCl_3$) 1.46 (9H, s), 3.25 (2H, t, J 7.0 Hz), 3.41 (4H, m), 3.46 (4H, m), 4.20 (2H, t, J 7.0 Hz), 5.10 (2H, s), 6.84 (1H, m), 6.88 (1H, m), 6.92 (1H, m), 7.14–7.24 (3H, m) and 7.28–7.36 (2H, m); HPLC retention time 8.12 min (λ=220 nm).

3-[2-(3-Chlorophenyl)ethyl]oxybenzylpiperazine-1-carboxylate hydrochloride was prepared from 3-[2-(3-chlorophenyl)ethyl]oxybenzyl-4-tert-butoxycarbonylpiperazine-1-carboxylate using the method described for Example 52 to yield the title compound (0.14 g, 67%) as a white solid; $^1$H NMR (400 MHz, $d_6$-DMSO) 3.05 (2H, t, J 7.0 Hz), 3.08 (4H, m), 3.62 (4H, m), 4.20 (2H, t, J 6.5 Hz), 5.06 (2H, s), 6.88–6.95 (3H, m), 7.25–7.35 (4H, m), 7.42 (1H, m) and 9.20 (2H, br s); HPLC retention time 5.67 min (λ=220 nm).

Example 54 cis-2,6-dimethyl-piperazine-1-carboxylic acid 6-(2-fluoro-benzyloxy)-pyridin-3-ylmethyl ester hemifumarate 6-(2-Fluorobenzyloxy)nicotinic acid: to a stirred suspension of sodium hydride (60%, 0.63 g) in DMF (10 ml) at 0° C. was added portionwise over 10 min 6-chloronicotinic acid (1.0 g). The mixture was stirred for 30 min then a solution of 2-fluorobenzyl alcohol (0.84 g) in DMF (5 ml) was added dropwise over 10 min. The mixture was warmed to room temperature, stirred for 1 h then heated to 100° C. and stirred for a further 18 h then cooled to room temperature. To the mixture were added dropwise water (10 ml) and hydrochloric acid (2M, 10 ml). The emerging precipitate was washed with water and dried to give the product as an off-white solid (1.34 g); $^1$H-NMR (400 MHz, $CDCl_3$) $\delta_H$ 8.75 (1H, dd, J 2.5, 1 Hz), 8.17 (1H, dd, J 8.5, 2.5 Hz), 7.56 (1H, dt, J 7.5, 1.5 Hz), 7.43 (1H, m), 7.27 (1H, dd, J 8.5, 1 Hz), 7.22 (1H, dd, J 7.5, 1 Hz), 6.97 (1H, dd, J 8.5, 1 Hz) and 5.48 (2H, s); [XTERRA; methanol-10 mM aqueous $NH_4OAc$ (50:50); 2 mL/min; 220 nm] 98%, 0.80 min.

2-(2-Fluorobenzyloxy)-5-pyridylmethanol: to a stirred solution of 6-(2-fluorobenzyloxy)nicotinic acid (0.89 g) in THF (10 ml) at 0° C. under Ar was added dropwise a solution of lithium aluminium hydride (1.0 M, 5.5 ml). The mixture was warmed to room temperature and stirred for 2 h. Saturated potassium sodium tartrate solution (1 ml) was added to the mixture followed by ethyl acetate (10 ml). The mixture was stirred for 30 min, filtered and concentrated in vacuo to give the product as a clear oil (0.63 g) which was used without further purification; $\delta_H$ (400 MHz, $CDCl_3$) 8.14 (1H, d, J 1.5 Hz), 7.63 (1H, dd, J 8.5, 2.5 Hz), 7.49 (1H, dt, J 7.5, 1 Hz), 7.29 (1H, m), 7.13 (1H, dt, J 7.5, 1 Hz), 7.02

(1H, dt, J 10, 1 Hz), 6.81 (1H, d, J 8 Hz), 5.45 (2H, s) and 4.63 (2H, s); LC 73%, 2.24 min.

cis-2,6-dimethyl-piperazine-1-carboxylic acid 6-(2-fluoro-benzyloxy)-pyridin-3-ylmethyl ester: to a stirred suspension of sodium hydride (0.084 g) in DMF (2 ml) was added dropwise a solution of 2-(2-fluorobenzyloxy)-5-pyridylmethanol (0.41 g) and cis 1-chlorocarbonyl-2,6-dimethyl-4-tert-butoxycarbonylpiperazine (0.45 g) in DMF (4 ml). The mixture was stirred for 18 h then poured into water (20 ml). The aqueous layer was extracted with two portions of ethyl acetate (20 ml). The combined organic extracts were washed (water, brine), dried (sodium sulfate) and concentrated in vacuo. The residue was purified by flash column chromatography [$SiO_2$; toluene-ether (4:1)] to give the product as a pale oil (0.28 g); 1H-NMR (400 MHz, $CDCl_3$) $\delta_H$ 8.19 (1H, d, J 2 Hz), 7.62 (1H, dd, J 8.5, 2.5 Hz), 7.50 (1H, dt, J 7.5, 1.5 Hz), 7.30 (1H, m), 7.14 (1H, dt, J 7.5, 1 Hz), 7.08 (1H, ddd, J 10, 8.5, 1.5 Hz), 6.80 (1H, d, J 8.5 Hz), 5.45 (2H, s), 5.09 (2H, s), 4.20 (2H, m), 4.05–3.80 (2H, m), 3.10–2.80 (2H, m), 1.48 (9H, s) and 1.22 (6H, d, J 6.5 Hz); HPLC [XTERRA; methanol-10 mM aqueous $NH_4OAc$ (50:50); 2 mL/min; 220 nm] 98%, 7.24 min.

cis-2,6-dimethyl-piperazine-1-carboxylic acid 6-(2-fluoro-benzyloxy)-pyridin-3-ylmethyl ester hemifumarate: cis-2,6-dimethyl-piperazine-1-carboxylic acid 6-(2-fluoro-benzyloxy)-pyridin-3-ylmethyl ester (0.25 g) and HCl-dioxane (4M, 0.6 ml) were combined as described below for Example 58 to give the product as a white solid (0.18 g); $^1$H-NMR (400 MHz, DMSO-$d_6$) 8.20 (1H, d, J 2 Hz), 7.75 (1H, d, J 8.5, 2.5 Hz), 7.53 (1H, dt, J 7.5, 1.5 Hz), 7.40 (1H, dddd, J 9, 7.5, 5.5, 1.5 Hz), 7.25 (1H, dd, J 9.5, 1 Hz), 7.20 (1H, dd, J 7.5, 1 Hz), 6.89 (1H, d, J 8.5 Hz), 6.57 (1H, s), 5.40 (2H, s), 5.04 (2H, s), 3.95 (2H, m), 2.74 (2H, d, J 12 Hz), 2.68 (2H, dd, J 12, 4.5 Hz) and 1.18 (6H, d, J 7 Hz); HPLC [XTERRA; methanol-10 mM aqueous $NH_4OAc$ (50:50); 2 mL/min; 220 nm] 99%, 4.23 min.

Example 55

4-Bromo-2-fluorobenzyl cis-2,6-dimethylpiperazine-1-carboxylate hydrochloride was synthesized from cis 1-chlorocarbonyl-2,6-dimethyl-4-tert-butoxycarbonylpiperazine and 4-bromo-2-fluorobenzyl alcohol according to the methods described in Examples 52 and 54 to give the product as a white solid: $\delta_H$ (400 MHz, DMSO-$d_6$) 1.3 (6H, d J, 7.2 Hz), 3.0–3.2 (4H, m), 4.3 (2H, sextet, J 7.2 Hz), 5.15 (2H, s), 7.42 (2H, m), 7.6 (1H, m), 9.15 (1H, br) and 9.80 (1H, br); LC (XTERRA, 50/80, 220 nm) 89.8% (3.62 min).

Example 56

Benzyl cis-2,6-dimethylpiperazine-1-carboxylate hydrochloride was prepared from cis 1-chlorocarbonyl-2,6-dimethyl-4-tert-butoxycarbonylpiperazine and benzyl alcohol according to the methods described for Examples 52 and 54 to give the product as a cream solid (0.0833 g, 15% overall); $\nu_{max}$ (nujol)/cm−1 2776, 2672, 2568, 2527, 1706, 1581, 1415, and 1329; $\delta_H$ (400 MHz, DMSO-$d_6$) 9.89 (1 H, br), 9.19 (1 H, br), 7.41–7.31 (5H, m), 5.13 (2 H, s), 4.34 (2 H, m), 3.17–3.08 (4 H, m), and 1.31 (6 H, d, J 7.2).

Example 57

2-Chlorobenzyl cis-2,6-dimethylpiperazine-1-carboxylate hydrochloride was prepared from cis 1-chlorocarbonyl-2,6-dimethyl-4-tert-butoxycarbonylpiperazine and 2-chlorobenzyl alcohol according to the methods described for Examples 52 and 54 to give the product as a white solid (0.0901 g, 14% overall); $\nu_{max}$ (nujol)/cm−1 3375, 2689, 2577, 1699, 1592, 1380, 1328, and 1300; $\delta_H$ (400 MHz, DMSO-$d_6$) 9.62 (2 H, br), 7.50 (2 H, m), 7.40 (2 H, m), 5.19 (2 H, s), 4.33 (2 H, m), 3.18–3.06 (4 H, m), and 1.31 (6 H, d, J 7.2).

Example 58

(R)-2-Fluorobenzyl 2-methylpiperazine-1-carboxylate hydrochloride

To a stirred solution of (R) 1-tert-butoxycarbonyl-4-chlorocarbonyl-2-methylpiperazine (348 mg, 1.32 mmol), triethylamine (550 uL, 3 eq) and 2-fluorobenzyl alcohol (420 uL, 2 eq) in dichloromethane (8 mL) were added pyridine (110 uL, 1 eq) and DMAP (cat.). The resultant mixture was stirred at ambient temperature for 5 days. Purification by flash column chromatography [$SiO_2$; ethyl acetate-heptane (1:3)] afforded a colourless oil (692 mg). This material was dissolved in MeOH (12 mL) and treated with a solution of HCl in dioxane (4 M; 3.3 mL, ~10 equiv.), with overnight stirring. Purification by flash column chromatography [$SiO_2$; ethyl acetate-methanol-ammonium hydroxide (90:8:2)] afforded a colourless oil. Dissolution in dichloromethane (4 mL) and treatment with HCl in dioxane (4 M; 1 mL) afforded, after evaporation the desired product (368 mg, 79%) as a white solid: $\delta_H$(400 MHz; $d_6$-DMSO) 1.26 (3H, d, J 7.0 Hz), 2.81–2.94 (1H, m), 3.01–3.27 (4H, m), 3.90–3.98 (1H, m), 4.31–4.40 (1H, m), 5.13 (1H, d, J 12.5 Hz), 5.17 (1H, d, J 12.5 Hz), 7.20–7.26 (2H, m), 7.38–7.50 (2H, m), 9.13 (1H, br s) and 9.59 (1H, br s); LC (XTERRA, 30/70, 210 nm) 99.6% (2.01 min).

Example 59

2-Fluoro-4-propylbenzyl cis-2,6-dimethylpiperazine-1-carboxylate hydrochloride 2-Fluoro-4-propylbenzyl 4-tert-butoxycarbonyl-cis-2,6-dimethylpiperazine-1-carboxylate: tetrakis(triphenylphosphine)palladium(0) (0.029 g) was added to a solution of 4-bromo-2-fluorobenzyl 4-tert-butoxycarbonyl-2,6-dimethylpiperazine-1-carboxylate (from Example 55, 0.223 g, 0.5 mmol) and n-propylzinc bromide (0.5 M THF, 3.0 ml) in dry THF (5 ml) under Ar. The reaction mixture was heated to reflux for 19 h, then cooled to ambient temperature and partitioned between ethyl acetate (50 ml) and saturated aqueous ammonium chloride solution (50 ml). The organic phase was separated, washed with water and brine, dried (sodium sulfate) and the solvent evaporated under reduced pressure to afford the crude product as an oil, which was purified by silica gel chromatography (DIPE:heptane, 1:1) and used immediately.

2-Fluoro-4-propylbenzyl cis-2,6-dimethylpiperazine-1-carboxylate hydrochloride was prepared from 2-fluoro-4-propylbenzyl 4-tert-butoxycarbonyl-cis-2,6-dimethylpiperazine-1-carboxylate according to the method described in Example 52: $\delta_H$ (400 MHz; $d_6$-DMSO) 0.9 (3H, t, J 7.3 Hz), 1.3 (6H, d, J 7.2 Hz), 1.59 (2H, sextet, J 7.3 Hz), 2.58 (2H, t, J 7.3 Hz), 3.0–3.2 (4H, m), 4.25 (2H, sextet, J 7.2 Hz), 5.15 (2H, s), 7.0–7.1 (2H, m), 7.38 (1H, t, J 7.9 Hz) and 9.0–10.0 (2H, br); HPLC (XTERRA, 50/80, 220 nm) 91% (4.93 min).

Example 60

S-4-[(Ethylamino)carbonyl]oxybenzyl piperazine-1-thiocarboxylate hydrochloride was prepared from S-4-hydroxybenzyl 4-tert-butoxycarbonylpiperazine-1-thiocarboxylate and ethyl isocyanate according to the method described in Example 71 to give the product as a white solid (58.6%); melting point 153.1–157.6° C.; NMR $\delta_H$ (400 MHz, DMSO-$d_6$) 1.069 (3H, t, J=7.0 Hz), 3.116 (6H, m), 3.667(4H, bs), 4.140(2H, s), 7.020(2H, d, J 8.5 Hz), 7.325(2H, d, J 8.5 Hz), 7.744(1H, t, J 5.5 Hz) and 9.117(2H, bs).

Example 61

S-4-[[(2-Chloroethyl)amino]carbonyl]oxybenzyl piperazine-1-thiocarboxylate hydrochloride was prepared from S-4-hydroxybenzyl 4-tert-butoxycarbonylpiperazine-1-thiocarboxylate and 2-chloroethyl isocyanate according to the method described in Example 71 to give the product as a white solid (73.8%); melting point 206.3–206.4° C.; NMR $\delta_H$ (400 MHz, DMSO-$d_6$) 3.120(4H, bt), 3.385 (3H, q, J 6.0 Hz), 3.367(6H, m), 4.146(2H, s), 7.040(2H, d, J 9.0 Hz), 7.337(2H, d, J 8.5 Hz), 8.045(1H, t, J 5.5 Hz) and 8.987(2H, bs).

Example 62

S-4-[(Butylamino)carbonyl]oxybenzyl piperazine-1-thiocarboxylate hydrochloride was prepared from S-4-hydroxybenzyl 4-tert-butoxycarbonylpiperazine-1-thiocarboxylate and butyl isocyanate according to the method described in Example 71 to give the product as a white solid (65.7%); melting point 176.7–177.7° C.; NMR $\delta_H$ (400 MHz, DMSO-$d_6$) 0.884(3H, t, J 7.0 Hz), 1.310(2H, m), 1.436(2H, m), 3.041(2H, q, J 6.0 Hz), 3.105(4H, bt), 3.638(4H, bs), 4.132 (2H, s), 7.015(2H, d, J 8.5 Hz), 7.323(2H, d, J 9.0 Hz) 7.736(2H, t, J 6.0 Hz) and 8.733(2H, bs).

Example 63

S-4-[(2-Propylamino)carbonyl]oxybenzyl piperazine-1-thiocarboxylate hydrochloride was prepared from S-4-hydroxybenzyl 4-tert-butoxycarbonylpiperazine-1-thiocarboxylate and propyl isocyanate according to the method described in Example 71 to give the product as a white solid (83.7%); HPLC (XTERRA, 50/80, 220 nm) 87% (1.15 min), NMR $\delta_H$ (400 MHz, DMSO-$d_6$) 1.113(6H, d, J 6.5 Hz), 3.108(4H, bt), 3.638(5H, bm), 4.138(2H, s), 7.020(2H, d, J 8.5 Hz), 7.321(2H, d, J 8.5 Hz), 7.682(1H, bd) and 8.721 (2H, bs).

Example 64

S-4-[(Benzylamino)carbonyl]oxybenzyl piperazine-1-thiocarboxylate hydrochloride was prepared from S-4-hydroxybenzyl 4-tert-butoxycarbonylpiperazine-1-thiocarboxylate and benzyl isocyanate according to the method described in Example 71 to give the product as a white solid (62.1%); HPLC (XTERRA, 50/80, 220 nm) 89% (1.15 min); NMR $\delta_H$ (400 MHz, DMSO-$d_6$) 3.113(4H, bs), 3.634(4H, bs), 4.144(2H, s), 4.256(2H, s), 7.110(2H, d, J 8.5 Hz), 7.328(7H, m), 8.328(1H, bs) and 8.890(2H, bs).

Example 65

S-4-[[(2-Methylbenzyl)amino]carbonyl]oxybenzyl piperazine-1-thiocarboxylate hydrochloride was prepared from S-4-hydroxybenzyl 4-tert-butoxycarbonylpiperazine-1-thiocarboxylate and 2-methylbenzyl isocyanate according to the method described in Example 71 to give the product as a white solid (62.1%); HPLC (XTERRA, 50/80, 220 nm) 89% (1.15 min); NMR $\delta_H$ (400 MHz, DMSO-$d_6$) 3.113(4H, bs), 3.634(4H, bs), 4.144(2H, s), 4.256(2H, s), 7.110(2H, d, J 8.5 Hz), 7.328(7H, m), 8.328(1H, bs) and 8.890(2H, bs).

Example 66

4-Difluoromethoxybenzyl cis-2,6-dimethylpiperazine-1-carboxylate hydrochloride

4-Difluoromethoxybenzyl alcohol: to a stirred solution of 4-difluoromethoxybenzaldehyde (1.0 g) in methanol (20 ml) was added sodium borohydride (0.11 g). The mixture was stirred for 2 h then concentrated in vacuo and partitioned between dichloromethane (50 ml) and dilute aqueous sodium hydroxide solution (50 ml). The organic layer was washed (water, brine), dried (sodium sulfate) and concentrated in vacuo to give the product as an oil (0.89 g), which was used without further purification.

4-Difluoromethoxybenzyl cis-2,6-dimethylpiperazine-1-carboxylate hydrochloride was prepared from cis 1-chlorocarbonyl-2,6-dimethyl-4-tert-butoxycarbonylpiperazine and 4-difluoromethoxybenzyl alcohol according to the methods described for Examples 52 and 54 to give the product as a white solid (0.202 g, 58% overall); (Found: C, 51.4; H, 6.2; N, 8.0%. $C_{15}H_{20}F_2N_2O_3$.HCl requires C, 51.4; H, 6.0; N, 8.0%); $\delta_H$ (400 MHz, DMSO-$d_6$) 9.87 (2H, br), 7.44 (2H, d, J 8.8 Hz), 7.24 (1H, t, J 74 Hz), 7.19 (2H, d, J 8.8 Hz), 5.11 (2H, s), 4.32 (2H, m), 3.14 (2H, d, J 13.2 Hz), 3.06 (2H, dd, J 5.2 and 13.2 Hz), and 1.31 (6H, d, J 7.2 Hz).

Example 67 cis-2,6-Dimethyl-piperazine-1-carboxylic acid 6-(3-methyl-butoxy)-pyridin-3-ylmethyl ester fumarate 6-(3-Methylbutoxy)nicotinic acid was prepared from 6-chloronicotinic acid (0.50 g), 3-methyl-1-butanol (0.36 ml) and sodium hydride (60%, 0.32 g) according to the method described in Example 54 to give the product as a white solid (0.25 g, 38%): $\delta_H$ (400 MHz, DMSO-$d_6$) 12.97 (1H, m), 8.71 (1H, d, J 2.5 Hz), 8.12 (1H, dd, J 8.5, 2.5 Hz), 6.87 (1H, d, J 8.5 Hz), 4.36 (2H, t, J 7 Hz), 1.75 (1H, nonet, J 6.5 Hz), 1.62 (2H, q, J 6.5 Hz) and 0.93 (6H, d, J 6.5 Hz); HPLC (XTERRA, 20/50, 220 nm) 99% (3.90 min).

[6-(3-Methyl-butoxy)-pyridin-3-yl]-methanol was prepared from 6-(3-methylbutoxy)nicotinic acid (0.24 g) and lithium aluminium hydride (0.5M, THF, 3.5 ml) according to the method described in Example 54 to give the product as a yellow oil (0.19 g, 86%): $\delta_H$ (400 MHz, $CDCl_3$) 8.08 (1H, d, J 2.5 Hz), 7.59 (1H, dd, J 8.5, 2.5 Hz), 6.71 (1H, d, J 8.5 Hz), 4.60 (2H, s), 4.30 (2H, t, J 6.5 Hz), 1.81 (1H, nonet, J 6.7 Hz), 1.66 (3H, q, J 7 Hz) and 0.96 (6H, d, J 6.5 Hz); HPLC (XTERRA, 50/80, 235 nm) 86% (2.54 min).

cis-2,6-Dimethyl-piperazine-1-carboxylic acid 6-(3-methyl-butoxy)-pyridin-3-ylmethyl ester was prepared from [6-(3-Methyl-butoxy)-pyridin-3-yl]-methanol (0.19 g), sodium hydride (60%, 0.048 g) and 4-tert-butoxycarbonyl-1-chlorocarbonyl-cis-2,6-dimethylpiperazine (0.25 g) according to the method described in Example 54 to give the product as a pale oil (0.052 g, 13%): $\delta_H$ (400 MHz, $CDCl_3$) 8.15 (1H, d, J 2.5 Hz), 7.58 (1H, dd, J 8.5, 2.5 Hz), 6.71 (1H, d, J 8.5 Hz), 5.07 (2H, s), 4.32 (2H, t, J 7 Hz), 4.18 (2H, m), 3.95 (2H, m), 2.95 (2H, m), 1.81 (1H, nonet, J 7 Hz), 1.67 (2H, q, J 7 Hz), 1.47 (9H, s), 1.22 (6H, d, J 7 Hz) and 0.96 (6H, d, J 6.5 Hz); HPLC (XTERRA, 50/80, 235 nm) 91% (7.19 min).

cis-2,6-dimethyl-piperazine-1-carboxylic acid 6-(3-methyl-butoxy)-pyridin-3-ylmethyl ester fumarate was prepared from cis-2,6-dimethyl-piperazine-1-carboxylic acid 6-(3-methyl-butoxy)-pyridin-3-ylmethyl ester (0.05 g) and HCl (4M, dioxane, 0.2 ml) according to the method described in Example 48 to give the product as a white solid (0.012 g, 28%): □$_H$ (400 MHz, DMSO-$d_6$) 8.15 (1H, d, J 2.5 Hz), 7.69 (1H, dd, J 8.5, 2 Hz), 6.79 (1H, d, J 8.5 Hz), 6.60 (2H, s), 5.02 (2H, s), 4.27 (2H, t, J 7 Hz), 3.95 (2H, m), 2.75 (2H, d, J 12 Hz), 2.68 (2H, dd, J 12, 4 Hz), 1.74 (1H, nonet, J 6.7 Hz), 1.60 (2H, q, J 7 Hz), 1.18 (6H, d, J 7 Hz) and 0.92 (6H, d, J 6.5 Hz); HPLC (XTERRA, 50/80, 235 nm) 95% (4.46 min).

Example 68 cis-2,6-Dimethyl-piperazine-1-carboxylic acid 6-(3-methyl-butoxy)-pyridin-3-ylmethyl ester hemifumarate 6-(Cyclohexylmethoxy)nicotinic acid was prepared from 6-chloronicotinic acid (0.50 g), cyclohexylmethanol (0.41 ml) and sodium hydride (60%, 0.32 g) according to the method described in Example 54 to give the product as a white solid (0.42 g, 56%): $\delta_H$ (400 MHz, DMSO-$d_6$) 12.97 (1H, br), 8.70 (1H, d, J 2.5 Hz), 8.12 (1H, dd, J 8.5, 2.5 Hz), 6.88 (1H, d, J 8.5 Hz), 4.14 (2H, d, J 6 Hz), 1.81–1.60 (6H, m), 1.20 (3H, sept of triplets, J 12, 2.5 Hz) and 1.03 (2H, dq, J 11, 2.5 Hz); HPLC (XTERRA, 50/80,220 nm) 100% (1.47 min).

[5-(2-Cyclohexylmethoxy)pyridyl]methanol was prepared from 6-cyclohexylmethoxynicotinic acid (0.39 g) and lithium aluminium hydride (0.5M, THF, 3.5 ml) according to the procedure described for Example 54 to give the product as a yellow oil (0.36 g, 96%): $\delta_H$ (400 MHz, $CDCl_3$) 8.07 (1H, d, J 2.5 Hz), 7.60 (1H, dd, J 8.5, 2.5 Hz), 6.72 (1H, d, J 8.5 Hz), 4.60 (2H, s), 4.08 (2H, d, J 6.5 Hz), 1.88–1.67 (6H, m), 1.24 (3H, septet of triplets, J 12, 3 Hz) and 1.04 (2H, dq, J 12, 3 Hz); HPLC (XTERRA, 50/80, 235 nm) 77% (4.49 min).

cis-2,6-Dimethyl-piperazine-1-carboxylic acid 6-(3-methyl-butoxy)-pyridin-3-ylmethyl ester was prepared from [5-(2-cyclohexylmethoxy)pyridyl]methanol (0.36 g), sodium hydride (60%, 0.77 g) and 4-tert-butoxycarbonyl-1-chlorocarbonyl-cis-2,6-dimethylpiperazine (0.40 g) according to the method described for Example 54 to give the product as a pale oil (0.035 g, 5%): $\delta_H$ (400 MHz, $CDCl_3$) 8.14 (1H, d, J 2.5 Hz), 7.58 (1H, dd, J 8.5, 2.5 Hz), 6.72 (1H, d, J 8.5 Hz), 5.07 (2H, s), 4.18 (2H, m), 4.09 (2H, d, J 6.5 Hz), 3.92 (2H, m), 2.95 (2H, m), 1.88–1.65 (6H, m), 1.47 (9H, s), 1.24 (3H, septet of triplets, J 12.5, 3 Hz), 1.22 (6H, d, J 7 Hz) and 1.05 (2H, dq, J 13, 3 Hz); HPLC (XTERRA, 50/80, 235 nm) 91% (8.06 min).

cis-2,6-Dimethyl-piperazine-1-carboxylic acid 6-(3-methyl-butoxy)-pyridin-3-ylmethyl ester hemifumarate was prepared from [5-(2-cyclohexylmethoxy)pyridyl]methyl 4-tert-butoxycarbonyl-cis-2,6-dimethylpiperazine-1-carboxylate (0.03 g) and HCl (4M, dioxane, 0.2 ml) according to the method described in Example 48 to give the product as a white solid (0.011 g, 45%): $\delta_H$ (400 MHz, DMSO-$d_6$) 8.14 (1H, d, J 2.5 Hz), 7.69 (1H, dd, J 8.5, 2.5 Hz), 6.80 (1H, d, J 8.5 Hz), 6.58 (1H, s), 5.01 (2H, s), 4.06 (2H, d, J 6 Hz), 3.93 (2H, m), 2.73 (2H, d, J 12 Hz), 2.67 (2H, dd, J 12, 4.5 Hz), 1.80–1.60 (6H, m), 1.19 (3H, septet of triplets, J 12, 3 Hz), 1.17 (6H, d, J 7 Hz) and 1.02 (2H, m); HPLC (XTERRA, 50/80, 235 nm) 100% (5.83 min).

Example 69

4-Ethyl-2-fluorobenzyl cis-2,6-dimethylpiperazine-1-carboxylate

4-Ethyl-2-fluorobenzyl 4-tert-butoxycarbonyl-cis-2,6-dimethylpiperazine-1-carboxylate was prepared from 4-bromo-2-fluorobenzyl 4-tert-butylpiperazine-1-carboxylate and diethylzinc according to the method described for Example 59.

4-Ethyl-2-fluorobenzyl cis-2,6-dimethylpiperazine-1-carboxylate was prepared from 4-ethyl-2-fluorobenzyl 4-tert-butoxycarbonyl-cis-2,6-dimethylpiperazine-1-carboxylate according to the methods described for Example 54 to give the product as a yellow oil: $\delta_H$ (400 MHz, DMSO-$d_6$) 1.18 (3H, t, J 7.7 Hz), 1.28 (6H, d, J 7.2 Hz), 2.62 (2H, q, J 7.7 Hz), 3.05–3.2 (4H, m), 4.28 (2H, sextet, J 7.1 Hz), 5.15 (2H, s), 7.05–7.1 (2H, m), 7.39 (1H, t, J 7.9 Hz) and 9.0–10.0 (2H, br); HPLC (XTERRA, 50/80, 220 nm) 96% (3.65 min).

Example 70

2-Fluoro-4-pentylbenzyl cis-2,6-dimethylpiperazine-1-carboxylate

2-Fluoro-4-pentylbenzyl 4-tert-butoxycarbonyl-cis-2,6-dimethylpiperazine-1-carboxylate was prepared from 4-bromo-2-fluorobenzyl 4-tert-butylpiperazine-1-carboxylate and dipentylzinc according to the method described for Example 59.

2-Fluoro-4-pentylbenzyl cis-2,6-dimethylpiperazine-1-carboxylate was prepared from 2-fluoro-4-pentylbenzyl 4-tert-butoxycarbonyl-cis-2,6-dimethylpiperazine-1-carboxylate according to the methods described for Example 54 to give the product as a yellow oil: $\delta_H$ (400 MHz, DMSO-$d_6$) 0.85 (3H, t, J 7.0 Hz), 1.27 (10H, m), 1.55 (2H, sextet, J 7.0 Hz), 2.60 (2H, t, J 7.0 Hz), 3.03–3.2 (4H, m), 4.30 (2H, sextet, J 7.1 Hz), 5.15 (2H, s), 7.05–7.1 (2H, m), 7.39 (1H, t, J 7.9 Hz) and 8.8–9.8 (2H, br); HPLC (XTERRA, 50/80, 220 nm) 96% (6.46 min).

Example 71

S-4-[(tert-Butylamino)carbonyl]oxybenzyl piperazine-1-thiocarboxylate hydrochloride S-4-[(tert-Butylamino)carbonyl]oxybenzyl 4-tert-butoxycarbonylpiperazine-1-thiocarboxylate: to a stirred solution of S-4-hydroxybenzyl 4-tert-butoxycarbonylpiperazine-1-thiocarboxylate (1.35 g, 3.7 mmol) in dichloromethane (50 mL) were added tert-butyl isocyanate (0.85 ml, 7.4 mmol) and triethylamine (0.1 ml). The mixture was stirred for 18 h then diluted with isohexane (30 mL) and concentrated in vacuo. The solid residue was washed with isohexane to give the crude product as a white solid (1.74 g, >100%) which was used without further purification.

To a stirred solution of the crude product from above (3.7 mmol) in methanol (10 mL) was added dropwise HCl-dioxane (4M, 9.2 ml, 10 eq.). The mixture was stirred at room temperature for 4 h then concentrated in vacuo. Diethyl ether (10 mL) was added to the residue which was left to stand for 18 h. The precipitate formed was filtered-off, washed with ether and dried to give the title compound as a white, crystalline solid (1.15 g, 80%): HPLC (XTERRA, 50/80,220 nm) 91.4% (1.81 min); NMR $\delta_H$ (400 MHz, DMSO-$d_6$) 1.269(9H, s), 3.119(4H, bt), 3.673(4H, bs), 4.141(2H, s), 6.998(2H, d, J 8.5 Hz), 7.322(2H, d, J 8.5 Hz) and 7.522(1H, s).

Example 72

2,5-Difluorobenzyl cis-2,6-dimethylpiperazine-1-carboxylate hydrochloride was prepared from cis 1-chlorocarbonyl-2,6-dimethyl-4-tert-butoxycarbonylpiperazine and 2,5-difluorobenzyl alcohol according to the methods described for Examples 52 and 54 to give the product as a white solid (0.247 g, 77% overall); (Found: C, 52.5; H, 6.1; N, 8.7%. $C_{14}H_{18}F_2N_2O_2$.HCl requires C, 52.4; H, 6.0; N, 8.7%); $\delta_H$ (400 MHz, DMSO-$d_6$), 9.98 (2H, br),7.29 (3H, m), 5.15 (2H, s), 4.31 (2H, m), 3.15 (2H, d, J 12.8 Hz), 3.06 (2H, dd, J 5 and 13 Hz), and 1.31 (6H, d, J 7.2 Hz).

Example 73

2,3-Difluorobenzyl cis-2,6-dimethylpiperazine-1-carboxylate hydrochloride was prepared from cis 1-chlorocarbonyl-2,6-dimethyl-4-tert-butoxycarbonylpiperazine and 2,3-difluorobenzyl alcohol according to the methods described for Examples 52 and 54 to give the product as a white solid (0.1846 g, 57% overall); (Found: C, 52.4; H, 6.0; N, 8.6%. $C_{14}H_{18}F_2N_2O_2$.HCl requires C, 52.4; H, 6.0; N, 8.7%); $\delta_H$ (400 MHz, DMSO-$d_6$) 10.07 (1H, br), 9.33 (1H, br), 7.44 (1H, m), 7.28 (2H, m), 5.21 (2H, s), 4.30 (2H, m), 3.14 (2H, d, J 13.2 Hz), 3.06 (2H, m), and 1.31 (6 H, d, J 7.2 Hz).

Example 74

2,6-Difluorobenzyl cis-2,6-dimethylpiperazine-1-carboxylate hydrochloride 2,6-Difluorobenzyl 4-tert-butoxycarbonyl-cis-2,6-dimethylpiperazine-1-carboxylate was prepared from cis 1-chlorocarbonyl-2,6-dimethyl-4-tert-butoxycarbonylpiperazine and 2,6-difluorobenzyl alcohol according to the method described for Example 54 to give the product as a colourless gum (0.251 g, 65%); $R_f$ (Silica, isopropyl ether) 0.35; $\delta_H$ (400 MHz, $CDCl_3$) 7.29 (1H, m), 6.90 (2H, m), 5.23 (2H, s), 4.16 (2H, m), 3.92 (2H, br), 2.95 (2H, br), 1.47 (9H, s), 1.21 (6H, d, J 6.8 Hz).

2,6-Difluorobenzyl cis-2,6-dimethylpiperazine-1-carboxylate hydrochloride was prepared from 2,6-difluorobenzyl 4-tert-butoxycarbonyl-cis-2,6-dimethylpiperazine-1-carboxylate according to the method described for Example 52 to give the title compound as a white solid (0.1585 g, 76%); (Found: C, 52.5; H, 6.3; N, 8.7%. $C_{14}H_{18}F_2N_2O_2$.HCl requires C, 52.4; H, 6.0; N, 8.7%); $\delta_H$ (400 MHz, DMSO-$d_6$) 10.02 (1H, br, s), 9.29 (1H, br, s), 7.51 (1H, m), 7.16 (2H, m), 5.18 (2H, s), 4.24 (2H, m), 3.12 (2H, d, J 12.8 Hz), 3.04 (2H, dd, J 5 and 12.8 Hz), and 1.28 (6H, d, J 7.2 Hz).

Example 75

2,4-Dimethylbenzyl cis-2,6-dimethylpiperazine-1-carboxylate hydrochloride was prepared from cis 1-chlorocarbonyl-2,6-dimethyl-4-tert-butoxycarbonylpiperazine and 2,4-dimethylbenzyl alcohol according to the methods described for Examples 52 and 54 to give the product as a hygroscopic white solid (0.1384 g, 44% overall); (Found: C, 60.9; H, 8.1; N, 8.9%. $C_{16}H_{24}N_2O_2$.HCl.0.25$H_2O$ requires C, 60.6; H, 8.1; N, 8.8%); $\delta_H$ (400 MHz, DMSO-$d_6$) 9.53 (2H, br), 7.19 (1H, d, J 7.6 Hz), 7.03 (1H, s), 6.99 (1H, d, J 7.6 Hz), 5.07 (2H, s), 4.29 (2H, m), 3.13 (2H, d, J 13.2 Hz), 3.04 (2H, dd, J 5.2 and 13.2 Hz), 2.27 (3H, s), 2.26 (3H, s) and 1.29 (6H, d, J 7.2 Hz).

Example 76

S-4-[(Propylamino)carbonyl]oxybenzyl piperazine-1-thiocarboxylate hydroxide was prepared from S-4-hydroxybenzyl 4-tert-butoxycarbonylpiperazine-1-thiocarboxylate and propyl isocyanate according to the method described in Example 71 to give the product as a white solid (25.3%); HPLC (XTERRA, 50/80) 98% (1.18 min); NMR $\delta_H$ (400 MHz, DMSO-$d_6$) 0.877(3H, t, J 7.5 Hz), 1.470(2H, m), 3.006(2H, q, J 6.5 Hz), 3.112(4H, bt), 3.673(4H, bt), 4141 (2H, s), 7.017(2H, d, J 8.5 Hz), 7.323(2H, d, J 8.5 Hz), 7.715(1H, t) and 9.126 (2H, bs).

Example 77

S-4-[(Cyclohexylamino)carbonyl]oxybenzyl piperazine-1-thiocarboxylate hydrochloride was prepared from S-4-hydroxybenzyl 4-tert-butoxycarbonylpiperazine-1-thiocarboxylate and cyclohexyl isocyanate according to the method described in Example 71 to give the product as a white solid (41.4%); HPLC (XTERRA, 50/80) 89% (3.63 min); NMR $\delta_H$ (400 MHz, DMSO-$d_6$) 1.234(6H, m), 1.554(1H, bd), 1.700(2H, bd), 1.808(2H, bd), 3.113(4H, bt), 3.677(4H, bs), 4.142(2H,s), 7.012(2H, d, J 8.5 Hz), 7.316(2H, d, J 8.0 Hz), 7.661(1H, d) and 9.189(1H, bs).

Example 78

2-Fluoro-4-difluoromethoxybenzyl cis-2,6-dimethylpiperazine-1-carboxylate fumarate 2-Fluoro-4-hydroxybenzyl alcohol: to a stirred solution of 3-fluorophenol (10.4 g) and potassium hydroxide (85%, 6.1 g) in water (20 ml) at 60° C. was added dropwise over 1 h a solution of 37% aqueous formaldehyde solution (14.3 ml) in added water (20 ml). The mixture was cooled to 40° C., stirred for 18 h then cooled to room temperature and acidified with dilute hydrochloric acid. The mixture was extracted with ethyl acetate (2×100 ml). The combined organic extracts were washed (water, brine), dried (sodium sulfate), concentrated in vacuo and purified by column chromatography ($SiO_2$; ethyl acetate-isohexane, 1:1) to give the product as a white, crystalline solid (1.0 g, 8%): $\delta_H$ (400 MHz, DMSO-$d_6$) 9.70 (1H, m, OH), 7.21 (1H, t, J 8.5 Hz), 6.58 (1H, dd, J 8, 2, Hz), 6.51 (1H, dd, J 12, 2 Hz), 4.98 (1H, m, OH) and 4.41 (2H, s); HPLC (XTERRA, 50/80, 235 nm) 93% (0.54 min).

4-Difluoromethoxy-2-fluorobenzyl alcohol: to a stirred solution of powdered potassium hydroxide (85%, 2.2 g) in 2-propanol (20 ml) was added dropwise a solution of 2-fluoro-4-hydroxybenzyl alcohol (1.0 g) in 2-propanol (5 ml). The mixture was cooled to −10° C. and chlorodifluoromethane was bubbled into the stirred mixture for 10 min. The reaction vessel was sealed and the mixture was stirred for 30 min at −10° C. then warmed slowly to room temperature and stirred for 18 h. The mixture was partitioned between ethyl acetate (2×30 ml) and water (30 ml). The combined organic extracts were washed (water, brine), dried (sodium sulfate), concentrated in vacuo and purified by column chromatography [$SiO_2$, isohexane-ethyl acetate (9:1→4:1)] to give the product as a clear oil (0.47 g, 35%): $\delta_H$ (400 MHz, $CDCl_3$) 7.43 (1H, t, J 8 Hz), 6.94 (1H, dd, J 8, 2.5 Hz), 6.87 (1H, dd, J 10.5, 2.5 Hz), 6.50 (1H, t, J 73 Hz) and 4.74 (2H, d, J 6 Hz).

4-Difluoromethoxy-2-fluorobenzyl cis-2,6-dimethylpiperazine-1-carboxylate fumarate was prepared from cis 1-chlorocarbonyl-2,6-dimethyl-4-tert-butoxycarbonylpiperazine and 4-difluoromethoxy-2-fluorobenzyl alcohol according to the methods described for Example 48 to give the product as an off-white solid (0.072 g, 41% overall); $\nu_{max}$ (nujol)/cm−1 3391, 2595, 1702, 1630, 1511, 1420, 1378, and 1342; $\delta_H$ (400 MHz, DMSO-$d_6$) 7.48 (1H, m), 7.30 (1H, t), 7.18–7.14 (2H, m), 6.58 (2H, s), 5.10 (2H, s), 3.97 (2H, t, J 6 Hz), 2.79 (2H, d, J 12.5 Hz), 2.72 (2H, dd, J 4.3 and 12.3 Hz), and 1.19 (6H, d, J 6.9 Hz).

Example 79

3-Benzyloxybenzyl cis-2,6-dimethylpiperazine-1-carboxylate hydrochloride was prepared from cis 1-chlorocarbonyl-2,6-dimethyl-4-tert-butoxycarbonylpiperazine and 3-benzyloxybenzyl alcohol according to the methods described for Examples 52 and 54 to give the product as a white solid (0.254 g, 65% overall); $\nu_{max}$ (nujol)/cm−1 3320, 2684, 2587, 1716, 1694, 1599, 1415, and 1312; $\delta_H$ (400 MHz, DMSO-$d_6$) 10.02 (1H, br), 9.27 (1H, br), 7.45–7.28 (6H, m), 7.01–6.94 (3H, m), 5.11 (2H, s), 5.09 (2H, s), 4.33 (2H, m), 3.15 (2H, d, J 13.2 Hz), 3.07 (2H, m), and 1.31 (6H, d, J 7.6 Hz).

Example 80

2,6-Difluoro-4-difluoromethoxybenzyl cis-2,6-dimethylpiperazine-1-carboxylate hydrochloride 2,6-Difluoro-4-difluoromethoxybenzyl alcohol: to a stirred solution of powdered potassium hydroxide (85%, 7.2 g) in 2-propanol (60 ml) was added dropwise a solution of 2,6-difluoro-4-hydroxybenzyl alcohol (3.5 g) in 2-propanol (20 ml). The mixture was cooled to −10° C. and chlorodifluoromethane was bubbled into the stirred mixture for 10 min. The reaction vessel was sealed and the mixture was stirred for 30 min at −10° C. then warmed slowly to room temperature and stirred for 18 h. The mixture was partitioned between ethyl acetate (2×100 ml) and water (100 ml). The combined organic extracts were washed (water, brine), dried (sodium sulfate), concentrated in vacuo and purified by column chromatography [$SiO_2$, isohexane-ethyl acetate (9:1→4:1)] to give the product as a clear oil (1.83 g, 40%): $\delta_H$ (400 MHz, $CDCl_3$) 6.74 (1H, t, J 4 Hz), 6.70 (1H, t, J 4 Hz), 6.51 (1H, t, J 73 Hz) and 4.75 (2H, d, J 6.5 Hz).

2,6-Difluoro-4-difluoromethoxybenzyl cis-2,6-dimethyl-4-tert-butoxycarbonyl-piperazine-1-carboxylate hydrochloride: to a stirred suspension of sodium hydride (60%, 86 mg, 1.5 eq.) in DMF (2 mL) at 0° C. was added dropwise a solution of cis-2,6-dimethyl-1-(chlorocarbonyl)-4-(tert-butoxycarbonyl)piperazine (0.40 g, 1 eq.) and 4-difluoromethoxy-2,6-difluorobenzyl alcohol (0.30 g, 1 eq.) in DMF (5 mL). The mixture was warmed to room temperature, stirred for 2 hours then partitioned between water (20 mL) and ethyl acetate (2×20 mL). The combined organic layers were washed (water, brine), dried (sodium sulfate) and concentrated to give a yellow oil (0.72 g), which was used without further purification.

2,6-Difluoro-4-difluoromethoxybenzyl cis-2,6-dimethylpiperazine-1-carboxylate hydrochloride was prepared from cis 1-chlorocarbonyl-2,6-dimethyl-4-tert-butoxycarbonylpiperazine and 2,6-difluoro-4-difluoromethoxybenzyl alcohol according to the method described for Example 54 to give the product as a, white solid (0.1406 g, 65% overall); $\nu_{max}$ (nujol)/cm−1 3342, 1684, 1640, 1599, 1378, 1308, 1166, and 1089; $\delta_H$ (400 MHz, DMSO-$d_6$) 9.69 (2H, br), 7.38 (1H, t, J 73 Hz), 7.15–7.10 (2H, m), 5.14 (2H, s), 4.24 (2H, m), 3.13 (2H, d, J 13 Hz), 3.05 (2H, dd, J 5.2 and 13 Hz), and 1.27 (6H, d, J 7.2 Hz).

Example 81

(+/−)-S-4-[(2-Butylamino)carbonyl]oxybenzyl piperazine-1-thiocarboxylate hydrochloride, was prepared from S-4-hydroxybenzyl 4-tert-butoxycarbonylpiperazine-1-thiocarboxylate and (+/−) sec-butyl isocyanate according to the method described in Example 71 to give the product as a white solid (41.2%); melting point 185.7–205.6° C.; NMR $\delta_H$ (400 MHz, DMSO-$d_6$) 0.871(3H, t, J 7.5 Hz), 1.090(3H, d, J 7.0 Hz), 1.440(2H, m), 3.115(4H, t), 3.455(1H, m), 3.672(4H, bt) 4.142(2H, s), 7.012(2H, d, J 8.5 Hz), 7.325 (2H, d, J 8.5 Hz), 7.584(1H, d) and 9.085(1H, bs).

Example 82

S-4-[(Cyclopentylamino)carbonyl]oxybenzyl piperazine-1-thiocarboxylate hydrochloride was prepared from S-4-hydroxybenzyl 4-tert-butoxycarbonylpiperazine-1-thiocarboxylate and cyclopentyl isocyanate according to the method described in Example 71 to give the product as a white solid (88.2%); melting point 196.5–197.6° C.; NMR $\delta_H$ (400 MHz, DMSO-$d_6$) 1.499(4H, m), 1.652(2H, m), 1.828(2H, m), 3.116(4H, bt), 3.312(5H, bs), 3.678(4H, bt), 3.818(1H, m), 4.142(2H, s), 7.017(2H, d, J 8.0 Hz), 7.321 (2H, d, J 8.5 Hz), 7.736(1H, d) and 9.157(2H, bs).

Example 83

S-4-[(1-Adamantylamino)carbonyl]oxybenzyl piperazine-1-thiocarboxylate hydrochloride was prepared from S-4-hydroxybenzyl 4-tert-butoxycarbonylpiperazine-1-thiocarboxylate and adamantanyl isocyanate according to the method described in Example 71 to give the product as a white solid (38.2%); melting point 200.7–200.8° C.; NMR $\delta_H$ (400 MHz, DMSO-$d_6$) 1.612(6H, m), 1.905(6H, m), 2.027(3H, bs), 3.119(4H, bt), 3.669(4H, bs), 4.138(2H, s), 6.987(2H, d, J 8.5 Hz), 7.321(2H, d, J 8.5 Hz), 7.449(1H, bs) and 9.070(2H, s).

Example 84

S-4-[(2-Propenylamino)carbonyl]oxybenzyl piperazine-1-thiocarboxylate hydrochloride was prepared from S-4-hydroxybenzyl 4-tert-butoxycarbonylpiperazine-1-thiocarboxylate and allyl isocyanate according to the method described in Example 71 to give the product as a white solid (18.6%); melting point 193.8–193.9° C.; NMR $\delta_H$ (400 MHz, DMSO-$d_6$) 3.101(4H, bt), 3.689(4H, bs), 3.757(2H, bs), 4.147(2H, s), 5.102(1H, dd, J 1.5, 10.5 Hz), 5.201(1H, d, J 1.5, 17.5 Hz), 7.026(2H, d, J 8.5 Hz), 7.332(2H, d, J 8.5 Hz), 7.925(1H, t) and 9.431(2H, bs).

Example 85

S-4-[(Phenylamino)carbonyl]oxybenzyl piperazine-1-thiocarboxylate hydrochloride was prepared from S-4-hydroxybenzyl 4-tert-butoxycarbonylpiperazine-1-thiocarboxylate and cyclohexyl isocyanate according to the method described in Example 71 to give the product as a white solid (8.0%); melting point 177.9–201.9° C.; NMR $\delta_H$ (400 MHz, DMSO-$d_6$) 3.127(4H, bt), 3.687(4H, bs), 4.180(2H, s), 7.055(1H, t, J 7.5 Hz), 7.144(2H, d, J 8.5 Hz), 7.323(2H, t, J 8.5 Hz), 7.391(2H, d, J 8.5 Hz), 7.495(2H, d, J 7.5 Hz), 9.078(2H, s) and 10.191(1H, s).

Example 86

S-4-[[4-(2-Propyl)phenylamino]carbonyl]oxybenzyl piperazine-1-thiocarboxylate hydrochloride was prepared from S-4-hydroxybenzyl 4-tert-butoxycarbonylpiperazine-1-thiocarboxylate and 4-(2-propyl)phenyl isocyanate according to the method described in Example 71 to give the product as a white solid (4.8%); melting point 234.2–234.3° C.; NMR $\delta_H$ (400 MHz, DMSO-$d_6$) 1.179(6H, d, J 7.0 Hz), 3.121(4H, bt), 3.647(4H, bs), 4.168(2H, s), 7.141(2H, d, J 8.5 Hz), 7.183(2H, d, J 8.5 Hz), 7.387(4H, m), (9.019(2H, bs) and 10.089(1H, s).

Example 87

(+/−)-S-4-[[(1-Phenylethyl)amino]carbonyl]oxybenzyl piperazine-1-thiocarboxylate hydrochloride was prepared from S-4-hydroxybenzyl 4-tert-butoxycarbonylpiperazine-1-thiocarboxylate and 1-phenylethyl isocyanate according to the method described in Example 71 to give the product as a white solid (54.2%); melting point 231.9–232.0° C.; NMR $\delta_H$ (400 MHz, DMSO-$d_6$) 1.411(3H, d, J 7.0 Hz), 3.101(4H, bt), 3.668(4H, bs), 4.132(2H, s), 4.701(1H, m), 7.00(2H, d, J 8.0 Hz), 7.327(6H, m), 8.297(1H, bd) and 9.175(2H, bs).

Example 88

S-4-[[(4-Ethoxycarbonyl)phenylamino]carbonyl]oxybenzylpiperazine-1-thiocarboxylate hydrochloride was prepared from S-4-hydroxybenzyl 4-tert-butoxycarbonylpiperazine-1-thiocarboxylate and 4-(ethoxycarbonyl)phenyl isocyanate according to the method described in Example 71 to give the product as a white solid (77.3%); melting point 201.0–201.5□C; NMR δ H (400 MHz, DMSO-$d_6$) 1.308 (3H, t, J 7.0 Hz), 3.122(4H, bt), 3.680(4H, bt), 4.175(2H, s), 4.277(2H, q, J 7.0 Hz), 7.183(2H, d, J 8.5 Hz), 7.396(2H, d, J 8.5 Hz), 7.626(2H, d, J 9.0 Hz), 7.923(2H, d, J 9.0 Hz), 9.085(2H, bs) and 10.619(1H, bs).

Example 89

S-4-[[(3-Chloro-4-fluorophenyl)amino]carbonyl]oxybenzyl piperazine-1-thiocarboxylate hydrochloride was prepared from S-4-hydroxybenzyl 4-tert-butoxycarbonylpiperazine-1-thiocarboxylate and 3-chloro-4-fluorophenyl isocyanate according to the method described in Example 71 to give the product as a white solid (39.5%); melting point 204.1–204.2□C; NMR $\delta_H$ (400 MHz, DMSO-$d_6$) 3.113(4H, bt), 3.686(4H, bs), 4.168(2H, s), 7.401(2H, d, J 8.5 Hz), 7.593(4H, m), 7.718(1H, dd, J 2.5, 7.0 Hz), 9.229(2H, bs) and 10.458(1H, bs).

Example 90

S-4-[[(4-Difluoromethoxyphenyl)amino]carbonyl]oxybenzylpiperazine-1-thiocarboxylate hydrochloride was prepared from S-4-hydroxybenzyl 4-tert-butoxycarbonylpiperazine-1-thiocarboxylate and 4-difluoromethoxyphenyl isocyanate according to the method described in Example 71 to give the product as a white solid (30.7%); melting point 203.7–203.8□C; NMR $\delta_H$ (400 MHz, DMSO-$d_6$) 3.116(4H, bt), 3.683(4H, bs), 4.171(2H, s), 7.155(4H, d, J 8.5 Hz), 7.387(2H, d, J 8.5 Hz), 7.520(2H, d, J 9.0 Hz), 9.206(2H, s) and 10.285(1H, bs).

Example 91

4-Methylbenzyl cis-2,6-dimethylpiperazine-1-carboxylate hydrochloride was prepared from cis 1-chlorocarbonyl-2,6-dimethyl-4-tert-butoxycarbonylpiperazine and 4-methylbenzyl alcohol according to the methods described for Examples 52 and 54 to give the product as a white solid (0.2614 g, 87% overall); $\lambda_{max}$ (diffuse reflectance)/cm−1 2749, 2656, 2541, 1697, 1594, 1518, 1330, and 1112; $\delta_H$ (400 MHz, DMSO-$d_6$) 10.05 (1H, br), 9.32 (1H, br), 7.26 (2H, d, J 8.0 Hz), 7.18 (2H, d, J 8.0 Hz), 5.07 (2H, s), 4.30 (2H, m), 3.14 (2H, d, J 12.8 Hz), 3.05 (2H, m), 2.30 (3H, s), and 1.30 (6H, d, J 7.2 Hz).

Example 92

(+/−)-4-Difluoromethoxybenzyl 2-ethylpiperazine-1-carboxylate fumarate (RS) 4-Tert-butoxycarbonyl-2-ethylpiperazine: to a stirred solution of 2-ethylpiperazine dihydrochloride (J. Org. Chem., 1987, 52(6), 1045, 5.0 g) and triethylamine (9.3 ml) in DCM (50 ml) at 0° C. was added di-tert-butyl-dicarbonate (6.5 g). The mixture was warmed to room temperature, stirred for 2 h, washed successively with water, dilute sodium hydroxide solution, water and brine then dried (sodium sulfate) and concentrated in vacuo to give the product as a clear oil (5.1 g); $\delta_H$ (400 MHz, $CDCl_3$) 3.78 (1H, m), 3.71 (1H, d, J 12.5 Hz), 2.81 (1H, dt, J 11.5, 2.5 Hz), 2.69 (1H, t, J 10.5 Hz), 2.48 (1H, td, J 11.5, 3 Hz), 2.29 (1H, m), 2.17 (1H, m), 1.39 (9H, s), 1.31 (1H, dd, J 7.5, 6 Hz), 1.25 (1H, dd, J 7.5, 6 Hz) and 0.87 (3H, t, J 7 Hz); GC (150° C.-10 min-320° C.) 93%, 5.13 min.

(RS) 1-Chlorocarbonyl-2-ethyl-4-tert-butoxycarbonylpiperazine: a solution of (RS) 4-tert-butoxycarbonyl-2-ethylpiperazine (3.95 g) and pyridine (1.64 ml) in DCM (35 ml) was added dropwise to a stirred solution of triphosgene (2.1 g) in DCM (100 ml) at 0° C. under Ar. The mixture was warmed to room temperature, stirred for 30 min then washed with water (100 ml) and brine (100 ml). The organic solution was dried (sodium sulfate) and concentrated in vacuo. The residue was dissolved in isohexane, filtered and concentrated in vacuo to give the product as a clear oil (3.73 g) which was used without further purification; $\delta_H$ (400 MHz, $CDCl_3$) 4.39–3.80 (4H, m), 3.39–2.69 (3H, m), 1.66 (2H, m), 1.47 (9H, s), 0.96 (2.7H, d, J 7 Hz) and 0.89 (0.3H, d, J 7 Hz); GC (150° C.-10 min-320° C.) 83%, 8.72 min.

(+/−) 4-Difluoromethoxybenzyl-2-ethyl-4-tert-butoxycarbonylpiperazine-1-carboxylate: sodium borohydride (0.11 g) was added to stirred 4-difluoromethoxybenzaldehyde (1.0 g) in methanol (20 ml). The mixture was stirred for 2 h then concentrated in vacuo. The residue was partitioned between DCM (30 ml) and aqueous sodium hydroxide solution (2M, 30 ml). The organic layer was filtered through a PTFE membrane and concentrated in vacuo to give a clear oil (0.89 g). The residue was combined with (RS) 1-chlorocarbonyl-2-ethyl-4-tert-butoxycarbonylpiperazine (1.1 g) and sodium hydride (0.31 g) according to the method described for Example 54 to give the product as a yellow oil (1.46 g), which was used without further purification.

(+/−)-4-Difluoromethoxybenzyl 2-ethylpiperazine-1-carboxylate fumarate: (+/−) 4-difluoromethoxybenzyl-2-ethyl-4-tert-butoxycarbonylpiperazine-1-carboxylate (0.045 g) and HCl-dioxane (4M, 0.2 ml) were combined according to the method described for Example 48 to give the product as a white solid (0.023 g); $\delta_H$ (400 MHz, DMSO-$d_6$) 7.41 (1H, d, J=8 Hz), 7.21 (1H, t, J 74 Hz), 7.17 (1H, d, J 8.5 Hz), 6.56 (2H, s), 5.08 (1H, d, J 13 Hz), 5.04 (1H, d, J 13 Hz), 3.91 (1H, m), 3.78 (1H, m), 2.90 (3H, m), 2.73 (1H, m), 2.57 (1H, m), 1.70 (1H, m), 1.62 (1H, m) and 0.77 (3H, t, J 7 Hz).

Example 93

S-4-[[(4-Methoxyphenyl)amino]carbonyl]oxybenzyl piperazine-1-thiocarboxylate hydrochloride was prepared from S-4-hydroxybenzyl 4-tert-butoxycarbonylpiperazine-1-thiocarboxylate and 4-methoxyphenyl isocyanate according to the method described in Example 71 to give the product as a white solid (22.4%); NMR $\delta_H$ (400 MHz, DMSO-$d_6$) 2.272(3H, s), 3.354(4H, bm), 3.445(4H, bs), 4.162(2H, s), 6.860(1H, d, J 7.5 Hz), 7.139(2H, d, J 9.0 Hz), 7.192(1H, t, J 7.5 Hz), 7.293(2H, d, J 8.5 Hz), 7.370(2H, d, J 8.5 Hz) and 10.104(1H, bs).

Example 94

S-4-[[(3-Methylbenzyl)amino]carbonyl]oxybenzyl piperazine-1-thiocarboxylate hydrochloride was prepared from S-4-hydroxybenzyl 4-tert-butoxycarbonylpiperazine-1-thiocarboxylate and 3-methylbenzyl isocyanate according to the method described in Example 71 to give the product as a white solid (58.4%); NMR $\delta_H$ (400 MHz, DMSO-$d_6$) 2.302 (3H, s), 3.344(4H, bm), 3.436(4H, bs), 4.125(2H, s), 4.231 (2H, d, J 6.5 Hz), 7.071(5H, m), 7.228(1H, t, J 7.5 Hz), 7.318(2H, d, J 8.5 Hz) and 8.232(1H, t, J 6.5 Hz).

Example 95

S-4-[[(4-Methoxybenzyl)amino]carbonyl]oxybenzyl piperazine-1-thiocarboxylate hydrochloride was prepared from S-4-hydroxybenzyl 4-tert-butoxycarbonylpiperazine-1-thiocarboxylate and 4-difluoromethoxyphenyl isocyanate according to the method described in Example 71 to give the product as a white solid (66.0%); $\delta_H$ (400 MHz, DMSO-$d_6$) 3.338(4H, bm), 3.437(4H, bs), 3.737(3H, s), 4.116(2H, s), 4.184(2H, d, J 6.0 Hz), 6.902(2H, d, J 8.5 Hz), 7.024(2H, d, J 8.5 Hz), 7.227(2H, d, J 9.0 Hz), 7.318(2H, d, J 8.5 Hz) and 8.193(1H, t, J 6.0 Hz).

Example 96

2,6-Difluoro-4-(2-propyl)oxybenzyl cis-2,6-dimethylpiperazine-1-carboxylate fumarate 2,6-Difluoro-4-(2-propoxy)benzyl alcohol: a mixture of 2,6-difluoro-4-hydroxybenzyl alcohol (0.20 g), cesium carbonate (0.22 g) and 2-iodopropane (0.14 ml) in DMF (10 ml) was heated to 40° C. and stirred for 18 h. The mixture was cooled to room temperature then poured into water (30 ml) and extracted with ethyl acetate (2×20 ml). The combined organic extracts were washed (water, brine), dried (sodium sulfate) and concentrated in vacuo to give the product as a yellow oil (0.25 g) which was used without further purification: $\delta_H$ (400 MHz, $CDCl_3$) 6.44 (1H, t, J 4 Hz), 6.40 (1H, t, J 4 Hz), 4.69 (2H, d, J 5.5 Hz), 4.48 (1H, hept., J 6 Hz) and 1.33 (6H, d, J 6 Hz).

2,6-Difluoro-4-(2-propoxy)benzyl cis-2,6-dimethylpiperazine-1-carboxylate fumarate was prepared from cis 1-chlorocarbonyl-2,6-dimethyl-4-tert-butoxycarbonylpiperazine and 2,6-difluoro-4-(2-propoxy)benzyl alcohol according to the methods described for Examples 48 and 54 to give the product as a white solid: $\delta_H$ (400 MHz, DMSO-$d_6$) 1.16 (6H, d, J 6.9 Hz), 1.26 (6H, d, J 6.0 Hz), 2.65–2.8 (4H, m), 3.90 (2H, m), 4.68 (1H, heptet, J 6.0 Hz), 5.02 (2H, s), 6.6 (2H, s, fumarate) and 6.75 (2H, m), NH not observed; HPLC (XTERRA, 50/80, 220 nm) 94% (4.00 min).

Example 97

S-4-(2-Oxo-2-phenylethoxy)benzyl piperazine-1-thiocarboxylate 4-(2-Oxo-2-phenylethoxy)benzyl 4-tert-butoxycarbonylpiperazine-1-thiocarboxylate: a mixture of 4-hydroxybenzyl 4-tert-butoxycarbonylpiperazine-1-thiocarboxylate (100 mg, 0.28 mmol), cesium carbonate (140 mg, 1.5 eq) and α-bromoacetophenone (84 mg, 1.5 eq) in DMF was shaken at ambient temperature for 16 h. The reaction mixture was poured into water (30 mL) and extracted with ethyl acetate (3×20 mL). The organic extracts were washed with water (30 mL), dried ($MgSO_4$) and condensed to give the desired product (129 mg, 96%) as a yellow oil: NMR $\delta_H$(400 MHz; $d_6$-DMSO) 1.40 (9H, s), 3.30–3.36 (4H, m), 3.43 (4H, br s), 4.07 (2H, s), 5.54 (2H, s), 6.86–6.91 (2H, m), 7.20–7.26 (2H, m), 7.54–7.60 (2H, m) and 7.66–7.72 (1H, m); HPLC (XTERRA, 50/80, 220 nm) 96.1% (6.56 min).

4-(2-Oxo-2-phenylethoxy)benzyl piperazine-1-thiocarboxylate: a solution of HCl in dioxane (4 M; 380 uL, 10 eq) was added to a solution of 4-(2-oxo-2-phenylethoxy)benzyl 4-tert-butoxycarbonylpiperazine-1-thiocarboxylate (72.1 mg) in ethyl acetate (2 mL) and the resultant mixture was shaken at ambient temperature for 16 h. The solvent was removed in vacuo and the resultant crude material was suspended in dichloromethane (4 mL) and shaken with MP—$CO_3$ (1 g, 17 eq) at ambient temperature for 1 h. Purification by ion-exchange chromatography [SCX-2 (500 mg); DCM, MeOH, $NH_3$—MeOH] afforded the desired product (44.7 mg, 79%) as a colourless oil: NMR $\delta_H$(400 MHz; $CDCl_3$) 2.82–2.86 (4H, m), 3.41–3.63 (4H, br s), 4.12 (2H, s), 5.23 (2H, s), 6.84–6.90 (2H, m), 7.24–7.29 (2H, m), 7.46–7.52 (2H, m) and 7.58–7.64 (1H, m); HPLC (XTERRA, 50/80, 235 nm) 97.7% (2.05 min).

Example 98

(R)-4-Difluoromethoxybenzyl 2-ethylpiperazine-1-carboxylate fumarate (R) 4-Difluoromethoxybenzyl-2-ethyl-4-tert-butoxycarbonylpiperazine-1-carboxylate: a sample of crude (+/−) 4-difluoromethoxybenzyl-2-ethyl-4-tert-butoxycarbonylpiperazine-1-carboxylate (Example 92, 0.1 g) in solution in isohexane-2-propanol (9:1, 0.7 ml) was separated by HPLC [Chiralcel AD; isohexane-2-propanol (9:1)] to give the product as a clear oil (0.053 g); $\delta_H$ (400 MHz, $CDCl_3$) 7.35 (2H, d, J 8.5 Hz), 7.11 (1H, d, J 8.5 Hz), 6.51 (1H, t, J 74 Hz), 5.13 (1H, d, J 12.5 Hz), 5.09 (1H, d, J 12.5 Hz), 4.19–3.82 (4H, m), 3.09–2.70 (3H, m), 1.57 (2H, m), 1.46 (9H, m) and 0.88 (3H, m); HPLC [Chiralcel AD 300×4.6 mm; hexane-2-propanol (9:1), 1.0 ml/min, 220 nm] 98% (10.51 min).

(R) 4-Difluoromethoxybenzyl-2-ethylpiperazine-1-carboxylate fumarate: (R) 4-difluoromethoxybenzyl-2-ethyl-4- tert-butoxycarbonylpiperazine-1-carboxylate (0.045 g) was prepared from (R) 4-difluoromethoxybenzyl-2-ethyl-4-tert-butoxycarbonylpiperazine-1-carboxylate according to the method described in Example 48 to give the product as a white solid (0.023 g); m.p. 164° C. (decomp.); $\delta_H$ (400 MHz, DMSO-$d_6$) 7.41 (1H, d, J 8 Hz), 7.21 (1H, t, J 74 Hz), 7.17 (1H, d, J 8.5 Hz), 6.56 (2H, s), 5.08 (1H, d, J 13 Hz), 5.04 (1H, d, J 13 Hz), 3.91 (1H, m), 3.78 (1H, m), 2.90 (3H, m), 2.73 (1H, m), 2.57 (1H, m), 1.70 (1H, m), 1.62 (1H, m) and 0.77 (3H, t, J 7 Hz).

Example 99

S-4-Benzenesulfonyloxybenzyl piperazine-1-thiocarboxylate hydrochloride

4-Benzenesulfonyloxybenzyl 4-tert-butoxycarbonylpiperazine-1-thiocarboxylate: triethylamine (57 uL, 0.41 mmol) and benzenesulfonyl chloride (38 uL) was added to a stirred solution of 4-hydroxybenzyl 4-tert-butoxycarbonylpiperazine-1-thiocarboxylate (0.10 g) in dichloromethane (3 mL) at ice-bath temperature. The reaction mixture was warmed to room temperature and stirred for 4 hours. The mixture was diluted with water (25 mL) and extracted with dichloromethane (2×30 mL). The combined organics were dried ($MgSO_4$), filtered and concentrated under vacuum to reveal a brown gum. Trituration with isohexane afforded the product as a white solid (44 mg, 32%) which was used without further purification.

4-Benzenesulfonyloxybenzyl piperazine-1-thiocarboxylate hydrochloride: to a stirred solution of 4-benzenesulfonyloxybenzyl 4-tert-butoxycarbonylpiperazine-1-thiocarboxylate (44 mg) in ethyl acetate (2 mL) was added hydrogen chloride solution (4M, dioxane, 0.23 mL). The mixture was stirred for 18 h then concentrated under vacuum to give the product as a white crystalline solid (31 mg, 78%): HPLC (XTERRA, 50/80, 220 nm) 98.4% (2.54 min); NMR $\delta_H$ (400 MHz, DMSO-$d_6$) 3.100(4H, bt), 3.672(4H, bt), 4.123(2H, s), 6.976(2H, d, J 8.5 Hz), 7.341(2H, d, J 9.0 Hz), 7.680(2H, t, J 8.0 Hz), 7.826(1H, t, J 7.5 Hz), 7.870(2H, d, J 7.0 Hz) and 9.258(2H, bs).

Example 100

(+/−)-2,6-Difluoro-4-propoxybenzyl 2-ethylpiperazine-1-carboxylate fumarate was prepared from (+/−) 1-chlorocarbonyl-2-ethyl-4-tert-butoxycarbonylpiperazine, 1-iodopropane and 2,6-difluoro-4-hydroxybenzyl alcohol according to the methods described for Examples 54 and 96 to give the product as a white solid (0.13 g, 42%); m.p. 145–165° C. (decomp.); $\delta_H$ (400 MHz, DMSO-$d_6$) 6.77 (1H, t, J 3.5 Hz), 6.73 (1H, t, J, 3.5 Hz), 5.07 (1H, d, J 12 Hz), 5.01 (1H, d, J 12 Hz), 3.97 (2H, t, J 6.5 Hz), 3.85 (1H, m), 3.72 (1H, m), 2.95–2.85 (3H, m), 2.74 (1H, dd, J 13, 4.5 Hz), 2.57 (1H, td, J 12.5, 3 Hz), 1.71 (2H, sept., J 7 Hz), 1.70 (1H, m), 1.57 (1H, sept. J 6.5 Hz), 0.96 (3H, t, J=7 Hz) and 0.73 (3H, t, J 6.5 Hz).

Example 101

(+/−)-2,6-Difluoro-4-difluoromethoxybenzyl 2-ethylpiperazine-1-carboxylate fumarate was prepared from (+/−) 1-chlorocarbonyl-2-ethyl-4-tert-butoxycarbonylpiperazine and 2,6-difluoro-4-difluoromethoxybenzyl alcohol according to the methods described for Examples 54 to give the product as a white solid (0.084 g, 38%); m.p. 145° C. (decomp.); Found: C, 49.04; H, 4.78; N, 5.87%. $C_{19}H_{22}F_4N_2O_7$ requires: C, 48.93; H, 4.75; N, 6.00%.

Example 102

2-Fluoro-5-methoxybenzyl cis-2,6-dimethylpiperazine-1-carboxylate hydrochloride

2-Fluoro-5-methoxybenzyl alcohol: sodium borohydride (0.061 g) was added to stirred 2-fluoro-5-methoxybenzaldehyde (0.5 g) in methanol (10 ml). The mixture was stirred for 2 h then concentrated in vacuo. The residue was partitioned between DCM (2×15 ml) and aqueous sodium hydroxide solution (2M, 10 ml). The combined organic layers were washed (water, brine), dried (sodium sulfate) and concentrated in vacuo to give a clear oil (0.5 g), which was used without further purification.

2-Fluoro-5-methoxybenzyl cis-2,6-dimethylpiperazine-1-carboxylate hydrochloride was prepared from cis 1-chlorocarbonyl-2,6-dimethyl-4-tert-butoxycarbonylpiperazine and 2-fluoro-5-methoxybenzyl alcohol according to the methods described for Examples 54 to give the product as white crystals (0.2714 g, 82% overall); (Found: C, 53.95; H, 6.7; N, 8.3%. $C_{15}H_{21}FN_2O_3$.HCl requires C, 54.1; H, 6.7; N, 8.4%); $\delta_H$ (400 MHz, DMSO-$d_6$) 9.84 (2H, br), 7.16 (1H, t, J 9.2 Hz), 6.99 (1H, m), 6.94 (1H, m), 5.13 (2H, s), 4.31 (2H, m, J 6 Hz), 3.73 (3H, s), 3.14 (2H, d, J 13 Hz), 3.06 (2H, dd, J 5.2 and 13 Hz), and 1.31 (6H, d, J 7.2 Hz).

Example 103

3-Difluoromethoxybenzyl cis-2,6-dimethylpiperazine-1-carboxylate fumarate was prepared from cis 1-chlorocarbonyl-2,6-dimethyl-4-tert-butoxycarbonylpiperazine and 3-difluoromethoxybenzyl alcohol according to the methods described for Examples 48 and 54 to give the product as a white solid (0.2816 g, 65% overall); (Found: C, 53.0; H, 5.8; N, 6.4%. $C_{15}H_{20}F_2N_2O_3.C_4H_4O_4$ requires C, 53.0; H, 5.6; N, 6.5%); $\delta_H$ (400 MHz, DMSO-$d_6$) 7.43 (1H, t, J 8.0 Hz), 7.24 (1H, s), 7.21 (1H, t, J 74 Hz), 7.13(2H, m, J 8.0 Hz), 6.59 (2H, s), 5.11 (2H, s), 4.02 (2H, m, J 6 Hz), 2.82–2.72 (4H, m), and 1.22 (6H, d, J 6.8 Hz).

Example 104

S-4-Propanesulfonyloxybenzyl piperazine-1-thiocarboxylate hydrochloride was prepared from S-4-hydroxybenzyl 4-tert-butoxycarbonylpiperazine-1-thiocarboxylate and 1-propylsulfonyl chloride according to the method described in Examples 71 and 99 to give the product as a colourless gum (51.6%); HPLC (XTERRA, 50/80, 220 nm) 96.3% (1.11 min); $\delta_H$ (400 MHz, DMSO-$d_6$) 1.033(3H, t, J 7.5 Hz), 1.846(2H, m), 3.117(4H, bs), 3.480(2H, t, J 7.5 Hz), 3.685 (4H, bs), 4.179(2H, s), 7.269(2H, d, J 9.0 Hz), 7.438(2H, d, J 8.5 Hz) and 9.236(2H, bs).

Example 105 cis-2,6-Dimethyl-piperazine-1-carboxylic acid 2,6-difluoro-4-(pyridin-3-ylmethoxy)-benzyl ester fumarate was prepared from 2,6-difluoro-4-hydroxybenzyl alcohol, 3-picolyl chloride hydrochloride and cis 1-chlorocarbonyl-2,6-dimethyl-4-tert-butoxycarbonylpiperazine according to the methods described for Examples 54 and 96 to give the product as a white solid: $\delta_H$ (400 MHz, DMSO-$d_6$) 1.25 (6H, d, J 6.9 Hz), 2.78–2.90 (4H, m), 4.04 (2H, m), 5.05 (2H, s), 5.10 (2H, s), 6.55 (2H, m), 7.34 (1H, dd, J 0.8, 4.8 Hz), 7.75 (1H, m), 8.62 (1H, dd, J 1.6, 4.8 Hz) and 8.67 (1H, m), NH not observed; HPLC (XTERRA, 50/80, 220 nm) 99.6% (1.82 min).

Example 106

(R)-2,6-Difluoro-4-propoxybenzyl 2-methylpiperazine-1-carboxylate fumarate was prepared from (R) 1-chlorocarbonyl-2-methyl-4-tert-butoxycarbonylpiperazine, 1-iodopropane and 2,6-difluoro-4-hydroxybenzyl alcohol according to the methods described for Examples 54 and 96 to give the product as a white solid (19.2%); melting point 193.9–194.0° C.; NMR $\delta_H$ (400 MHz, DMSO-$d_6$) 0.958(3H, t, J 7.5 Hz), 1.140(3H, d, J 7.0 Hz), 1.715(2H, m), 2.817(2H, m), 2.982(2H, m), 3.687(2H, m), 4.097(1H, bs), 5.027(2H, q, J 11.0 Hz), 6.573(2H, s) and 6.773(2H, d, J 10.0 Hz).

Example 107

(R)-4-Difluoromethoxybenzyl 2-methylpiperazine-1-carboxylate fumarate was prepared from (R) 1-chlorocarbonyl-2-methyl-4-tert-butoxycarbonylpiperazine and 4-difluoromethoxybenzyl alcohol according to the methods described for Examples 48 and 54 to give the product as a white solid (24.0%); melting point 123.9–124.5° C.; NMR $\delta_H$ (400 MHz, DMSO-$d_6$) 1.174(3H, d, J 7.0 Hz), 2.622(1H, m), 3.003(2H, m), 3.766(1H, dd, J 2.5, 13 Hz), 4.187(1H, m), 5.067(2H, m), 6.542 (2H, s), 7.178(2H, d, J 9.0 Hz), 7.244(1H, t, J 74.0) and 7.424(2H, d, J 8.5 Hz).

Example 108

5-Benzyloxy-2-fluorobenzyl cis-2,6-dimethylpiperazine-1-carboxylate hydrochloride was prepared from cis 1-chlorocarbonyl-2,6-dimethyl-4-tert-butoxycarbonylpiperazine, benzyl chloride and 2-fluoro-5-hydroxybenzyl alcohol according to the methods described for Examples 52, 54 and 96 to give the product as a white solid (0.229 g, 56% overall); (Found; C, 61.5; H, 6.5; N, 6.8%. $C_{21}H_{25}FN_2O_3$.HCl requires C, 61.7; H, 6.4; N, 6.85%); $\delta_H$ (400 MHz, DMSO-$d_6$) 9.86 (1H, br), 9.17 (1H, br), 7.45–7.33 (5H, m), 7.17 (1H, t, J 9 Hz), 7.08 (1H, m, J 2.8 Hz), 7.02 (1H, m), 5.12 (2H, s), 5.09 (2H, s), 4.29 (2H, m), 3.15 (2H, d, J 12.8 Hz), 3.06 (2H, dd, J 4.8 and 12.8 Hz), and 1.29 (6H, d, J 7.2 Hz).

Example 109

2,6-Difluoro-4-(3-phenyl)propoxybenzyl cis-2,6-dimethylpiperazine-1-carboxylate fumarate was prepared from 2,6-difluoro-4-hydroxybenzyl alcohol, 3-phenylpropyl bromide and cis 1-chlorocarbonyl-2,6-dimethyl-4-tert-butoxycarbonylpiperazine according to the methods described for Examples 48, 54 and 96 to give the product as a white solid: $\delta_H$ (400 MHz, DMSO-$d_6$) 1.25 (6H, d, J 6.9 Hz), 2.00 (2H, m), 2.64–2.80 (6H, m), 3.88, (2H, m), 4.02 (2H, t, J 6.4 Hz), 5.03 (2H, s), 6.60 (2H, s, fumarate), 6.76 (2H, m) and 7.18–7.30 (5H, m), NH not observed; HPLC (XTERRA, 50/80, 220 nm) 99% (6.75 min).

Example 110

4-Bromo-2-fluorobenzyl piperazine-1-carboxylate hydrochloride was prepared from 4-bromo-2-fluorobenzyl alcohol and 1-chlorocarbonyl-4-tert-butoxycarbonylpiperazine according to the methods described for Examples 52 and 54 to give the product as a white solid (26.5%); melting point 209.5–209.6° C.; NMR $\delta_H$ (400 MHz, DMSO-$d_6$) 3.078(4H, bt), 3.594(4H, bt), 5.118(2H, s), 7.455(2H, m), 7.592(1H, m) and 9.147(2H, bs).

Example 111

2,6-Difluoro-4-(2-propenyl)oxybenzyl cis-2,6-dimethylpiperazine-1-carboxylate was prepared from 2,6-difluoro-4-hydroxybenzyl alcohol, allyl bromide and cis 1-chlorocarbonyl-2,6-dimethyl-4-tert-butoxycarbonylpiperazine according to the methods described for Examples 54 and 96: NMR $\delta_H$ (400 MHz, DMSO-$d_6$) 1.25 (6H, d, J 6.9 Hz), 2.75–2.87 (4H, m), 4.04 (2H, m), 4.51 (2H, dt, J 5.3, 1.5 Hz), 5.14 (2H, s), 5.32 (1H, dq, J 10.5, 1.5 Hz), 5.41 (1H, dq, J 17.3, 1.5 Hz), 6.00 (1H, ddt, J 17.3, 10.5, 5.3 Hz) and 6.45 (2H, m), NH not observed; HPLC (XTERRA, 50/80, 220 nm) 97.3% (3.89 min).

Example 112

(R)-2,6-Difluoro-4-difluoromethoxybenzyl 2-methylpiperazine-1-carboxylate fumarate was prepared from 2,6-difluoro-4-difluoromethoxybenzyl alcohol and (R) 1-chlorocarbonyl-2-methyl-4-tert-butoxycarbonylpiperazine according to the methods described for Examples 54 to give the product as a white solid (2.9%); HPLC (XTERRA, 50/80, 220 nm) 86.0% (1.55 min); NMR $\delta_H$ (400 MHz, DMSO-$d_6$) 1.154(3H, d, J 7.0 Hz), 2.639(1H, bm), 2.863 (2H, bm), 3.007(2H, bm), 3.714(1H, bd), 4.122(1H, bs), 5.106(2H, q), 6.590(2H, s), 7.108(2H, d, J 8.5 Hz) and 7.360(1H, t, J 73 Hz).

Example 113

2-Fluoro-5-difluoromethoxybenzyl cis-2,6-dimethylpiperazine-1-carboxylate hydrochloride 2-Fluoro-5-difluoromethoxybenzyl alcohol: to a stirred solution of powdered potassium hydroxide (85%, 6.56 g) in 2-propanol (70 ml) was added dropwise a solution of 2-fluoro-5-hydroxybenzyl alcohol (1.43 g) in 2-propanol (5 ml). The mixture was cooled to −10° C. and chlorodifluoromethane was bubbled into the stirred mixture for 10 min. The reaction vessel was sealed and the mixture was stirred for 30 min at −10° C. then warmed slowly to room temperature and stirred for 18 h. The mixture was partitioned between isopropyl ether (2×100 ml) and water (350 ml). The combined organic extracts were washed (water, brine), dried (sodium sulfate), concentrated in vacuo and purified by column chromatography [$SiO_2$, isopropyl ether-pentane (1:4→1:0)] to give the product as a clear oil (0.86 g, 44%): $\delta_H$ (400 MHz, $CDCl_3$) 7.25 (1H, m), 7.03 (2H, m), 6.46 (1H, t, J 74 Hz), 4.76 (2H, d, J 6 Hz) and 1.85 (1H, t, J 6 Hz).

2-Fluoro-5-difluoromethoxybenzyl cis-2,6-dimethylpiperazine-1-carboxylate hydrochloride was prepared from 2-fluoro-5-difluoromethoxybenzyl alcohol and cis 1-chlorocarbonyl-2,6-dimethyl-4-tert-butoxycarbonylpiperazine according to the methods described for Examples 52 and 54 to give the product as a white solid (0.1473 g, 84%); $\nu_{max}$ (diffuse reflectance)/$cm^{-1}$ 2780, 2314, 1697, 1593, 1501, 1327, 1209, and 1101; $\delta_H$ (400 MHz, DMSO-$d_6$) 9.74 (1H, br), 9.18 (1H, br), 7.35–7.22 (3H, m), 7.20 (1H, t, J 74 Hz), 5.17 (2H, s), 4.31 (2H, m, J 6.4 Hz), 3.16 (2H, d, J 13 Hz), 3.08 (2H, dd, J 5.2 and 13 Hz), and 1.30 (6H, d, J 7.2 Hz).

Example 114

5-Ethoxy-2-fluorobenzyl cis-2,6-dimethylpiperazine-1-carboxylate fumarate was prepared from 2-fluoro-5-hydroxybenzyl alcohol, ethyl iodide and cis 1-chlorocarbonyl-2,6-dimethyl-4-tert-butoxycarbonylpiperazine according to the methods described for Examples 54 and 96 to give the product as a white solid (23.4%); melting point 142.9–143.3° C.; NMR $\delta_H$ (400 MHz, DMSO-$d_6$) 1.046(3H, d, J 6.0 Hz), 1.98(6H, d, J 7.0 Hz), 1.306(3H, t, J 7.0 Hz), 2.745(4H, m), 3.985(4H, m), 5.080(2H, s), 6.584(2H, s), 6.917(2H, m) and 7.129(1H, t, J 9.0 Hz).

Example 115

2-Fluoro-5-propoxybenzyl piperazine-1-carboxylate fumarate was prepared from 2-fluoro-5-hydroxybenzyl alcohol, 1-iodopropane and 1-chlorocarbonyl-4-tert-butoxycarbonylpiperazine according to the methods described for Examples 54 and 96 to give the product as a white solid (28.9%); melting point 155.9–156.1° C.; NMR $\delta_H$ (400 MHz, DMSO-$d_6$) 0.966(3H, t, J 7.5 Hz), 1.711(2H, m), 2.793(4H, bt), 3.397(4H, bt), 3.897(2H, t, J 6.5 Hz), 5.077 (2H, s), 6.549(2H, s), 6.937(2H, m) and 7.129(1H, t, J 9.0 Hz).

Example 116

(R)-2-Fluoro-5-propoxybenzyl 2-methylpiperazine-1-carboxylate fumarate was prepared from 2-fluoro-5-hydroxybenzyl alcohol, 1-iodopropane and (R) 1-chlorocarbonyl-2-methyl-4-tert-butoxycarbonylpiperazine according to the methods described for Examples 54 and 96 to give the product as a white solid (26.4%); melting point 162.6–162.7° C.; NMR $\delta_H$ (400 MHz, DMSO-$d_6$) 0.963(3H, t, J 7.5 Hz), 1.173(3H, d, J 7.0 Hz), 1.709(2H, m), 2.582(1H, m), 2.801(2H, bs), 2.991(2H, bm), 3.731(1H, bdd), 3.895 (2H, t, J 6.5 Hz), 4.142(1H, bm), 5.077(2H,q), 6.556(2H, s), 6.931(2H, m) and 7.126(1H, t, J 9.0 Hz).

Example 117

2-Fluoro-5-propoxybenzyl cis-2,6-dimethylpiperazine-1-carboxylate fumarate diethyl etherate was prepared from 2-fluoro-5-hydroxybenzyl alcohol, 1-iodopropane and 1-chlorocarbonyl-cis-2,6-dimethyl-4-tert-butoxycarbonylpiperazine according to the methods described for Examples 54 and 96 to give the product as a white solid (14.4%); melting point 142.6–144.1° C.; NMR $\delta_H$ (400 MHz, DMSO-$d_6$) 0.958(3H, t, J 7.0 Hz), 1.039(2H, d, J 6.0 Hz), 1.199(6H, d, J 7.0 Hz), 1.707(2H, m), 2.756(4H, bm), 3.891(2H, t, J 6.5 Hz), 3.978(2H, bm), 5.083(2H, s), 6.571 (2H, s), 6.932(2H, m) and 7.126(1H, t, J 9.0 Hz).

Example 118

5-Butoxy-2-fluorobenzyl piperazine-1-carboxylate fumarate was prepared from 2-fluoro-5-hydroxybenzyl alcohol, 1-iodobutane and 1-chlorocarbonyl-4-tert-butoxycarbonylpiperazine according to the methods described for Examples 54 and 96 to give the product as a white solid (15.2%); melting point 142.4–143.5° C.; NMR $\delta_H$ (400 MHz, DMSO-$d_6$) 0.927(3H, t, J 7.5 Hz), 1.423(2H, m, J 7.5 Hz), 1.679(2H, m, J 8.0 Hz), 2.798(4H, bt), 3.402(4H, bt), 3.939(3H, t, J 6.5 Hz), 6.537(2H, s), 6.928(2H, m) and 7.125(1H, t, J 9.0 Hz).

Example 119

(R)-5-Butoxy-2-fluorobenzyl 2-methylpiperazine-1-carboxylate fumarate was prepared from 2-fluoro-5-hydroxybenzyl alcohol, 1-iodobutane and (R) 1-chlorocarbonyl-2-methyl-4-tert-butoxycarbonylpiperazine according to the methods described for Examples 54 and 96 to give the product as a white solid (18%); melting point 171.6–171.7° C.; NMR $\delta_H$ (400 MHz, DMSO-$d_6$) 0.928(3H, t, J 7.0 Hz), 1.167(3H, d, J 7.0 Hz), 1.421(2H, m, J 7.5 Hz), 1.676(2H, m, J 7.5 Hz), 2.564(2H, bm), 2.787(2H, bs), 2.982(2H, bm), 3.717(1H, bdd), 3.931(2H, t, J 6.5 Hz), 4.122(1H, bm), 5.078(2H, q), 6.566(2H, s), 6.929(2H, m) and 7.123(1H, t, J 9.0 Hz).

Example 120

5-Butoxy-2-fluorobenzyl cis-2,6-dimethylpiperazine-1-carboxylate fumarate was prepared from 2-fluoro-5-hydroxybenzyl alcohol, 1-iodobutane and 1-chlorocarbonyl-cis-2,6-dimethyl-4-tert-butoxycarbonylpiperazine according to the methods described for Examples 54 and 96 to give the product as a white solid (24.4%); melting point 153.2–153.5° C.; NMR $\delta_H$ (400 MHz, DMSO-$d_6$) 0.923(3H, t, J7.5 Hz), 1.199(6H, d, J 7.0 Hz), 1.418(2H, m, J 7.5 Hz), 1.675(2H, m, J 7.5 Hz), 2.761(4H, bm), 3.960(4H, bm), 5.084(2H, s), 6.586(2H, s), 6.935(2H, m) and 7.125(1H, t, J 9.5 Hz).

Example 121 cis-2,6-Dimethyl-piperazine-1-carboxylic acid 4-(3,5-dimethyl-isoxazol-4-ylmethoxy)-2,6-difluoro-benzyl esterfumarate

[4-(3,5-Dimethyl-isoxazol-4-ylmethoxy)-2,6-difluoro-phenyl]-methanol: PS-BEMP (1.5 g, 2 eq) was added to a solution of 2,6-difluoro-4-hydroxybenzyl alcohol (400 mg, 1.5 eq) in acetonitrile (4 mL) and the mixture was shaken for 5 min. 4-(Chloromethyl)-3,5-dimethylisoxazole (210 uL, 1.67 mmol) was added and the resultant mixture was shaken at ambient temperature for 16 h. The mixture was filtered, the resin washed with dichloromethane (4×4 mL) and evaporated to afford the desired product (380 mg, 85%) as a white solid: NMR $\delta_H$(400 MHz; $d_6$-DMSO) 2.20 (3H, s), 2.40 (3H, s), 4.42 (2H, d, J 5.5 Hz), 5.95 (2H, s), 5.08 (1H, t, J 5.5 Hz) and 6.76–6.83 (2H, m); HPLC (XTERRA, 50/80, 220 nm) 94.5% (1.03 min).

cis-2,6-Dimethyl-piperazine-1-carboxylic acid 4-(3,5-dimethyl-isoxazol-4-ylmethoxy)-2,6-difluoro-benzyl ester: a solution of 4-tert-butoxycarbonyl-1-chlorocarbonyl-2,6-dimethylpiperazine (307 mg, 1 eq) and 4-[4-(3,5-dimethyl-isoxazolyl)]methoxybenzyl alcohol (300 mg, 1.11 mmol) in DMF (3 mL) was added to a suspension of sodium hydride (60%; 67 mg, 1.5 eq) in DMF (2 mL) pre-cooled in dry-ice for 2 min. The vented mixture was left shaking at ambient temperature for 16 h. The reaction mixture was poured onto ice-water (15 mL) and the resultant solid was filtered and washed with water (2×10 mL). Drying in a vacuum oven afforded the desired product (489 mg, 87%) as a low-melting pale yellow solid: NMR $\delta_H$(400 MHz; $d_6$-DMSO) 1.08 (6H, d, J 6.5 Hz), 1.40 (9H, s), 2.21 (3H, s), 2.41 (3H, s), 2.48–2.52 (2H, m), 3.68–3.85 (2H, br d, J 12 Hz), 3.95–4.06 (2H, m), 4.97 (2H, s), 5.07 (2H, s) and 6.83–6.92 (2H, m); HPLC (XTERRA, 50/80, 220 nm) 85.7% (6.26 min).

cis-2,6-Dimethyl-piperazine-1-carboxylic acid 4-(3,5-dimethyl-isoxazol-4-ylmethoxy)-2,6-difluoro-benzyl esterfumarate: a solution of HCl in dioxane (4 M; 2.3 mL, 10 eq) was added to a solution cis-2,6-dimethyl-piperazine-1-carboxylic acid 4-(3,5-dimethyl-isoxazol-4-ylmethoxy)-2,6-difluoro-benzyl ester (463 mg, 0.91 mmol) in methanol (15 mL) and the resultant mixture was stirred at ambient temperature for 8 h. The solvent was removed in vacuo and the residue was suspended in aqueous sodium hydroxide solution (2 N; 30 mL) and extracted with diethyl ether (2×20 mL) and ethyl acetate (1×20 mL). The combined organics were washed with brine (20 mL), dried ($MgSO_4$) and concentrated in vacuo to afford the free-base (195 mg) as a pale yellow solid. This material was dissolved in hot IPA (3 mL) and added to a stirred solution of fumaric acid (78 mg, 1.5 eq) in hot IPA (2 mL). The resultant suspension was allowed to cool to ambient temperature, then cooled in ice-water. Diethyl ether (5 mL) was added and the suspension was heated to give a solution, then allowed to cool. The resultant solution was cooled in ice-water and filtration afforded the desired product (155 mg, 32%) as a white, crystalline solid: NMR $\delta_H$(400 MHz; $d_6$-DMSO) 1.17 (6H, d, J 7.0 Hz), 2.21 (3H, s), 2.41 (3H, s), 2.71 (2H, dd, J 12.5, 4.5 Hz), 2.77 (2H, d, J 12.5 Hz), 3.88–3.96 (2H, m), 4.97 (2H, s), 5.06 (2H, s), 6.58 (2H, s) and 6.83–6.91 (2H, m); HPLC (XTERRA, 50/80, 220 nm) 99% (2.39 min).

Example 122

2-Fluoro-5-(2-methylpropyl)-oxybenzyl cis-2,6-dimethylpiperazine-1-carboxylate fumarate was prepared from 2-fluoro-5-hydroxybenzyl alcohol, 1-iodo-2-methylpropane and 1-chlorocarbonyl-4-tert-butoxycarbonylpiperazine according to the methods described for Examples 54 and 96 to give the product as a white solid (31.3%); melting point 178.6–178.70C; NMR $\delta_H$ (400 MHz, DMSO-$d_6$) 0.961(6H, d, J 7.0 Hz), 1.193(6H, d, J 7.0 Hz) 1.994(1H, m, J 6.5 Hz), 2.726(4H, bm), 3.709(2H, d, J 6.5 Hz), 3.966(2H, q), 5.084(2H, s), 6.593(2H, s), 6.933(2H, m) and 7.124(1H, t, J 9.0 Hz).

Example 123

2-Chloro-6-fluorobenzyl cis-2,6-dimethylpiperazine-1-carboxylate hydrochloride was prepared from 2-chloro-6-fluorobenzyl alcohol and 1-chlorocarbonyl-cis-2,6-dimethyl-4-tert-butoxycarbonylpiperazine according to the methods described for Examples 52 and 54 to give the product as a white solid (0.2713 g, 80% overall); (Found: C, 49.8; H, 5.7; N, 8.0%. $C_{14}H_{18}ClN_2O_2$.HCl requires C, 49.9; H, 5.7; N, 8.3%); $\delta_H$ (400 MHz, DMSO-$d_6$) 10.01 (1H, br), 9.27 (1H, br), 7.49 (1H, m, J 8.0 Hz), 7.40 (1H, d, J 8.0 Hz), 7.30 (1H, t, J 9 Hz), 5.22 (2H, d, J 1.6 Hz), 4.24 (2H, m, J 6.5 Hz), 3.17–3.06 (4H, m), and 1.28 (6H, d, J 7.2 Hz).

Example 124

(R)-2,6-Difluorobenzyl 2-methylpiperazine-1-carboxylate hydrochloride was prepared from 2,6-difluorobenzyl alcohol and (R) 1-chlorocarbonyl-2-methyl-4-tert-butoxycarbonylpiperazine according to the methods described for Examples 52 and 54 to give the product as a white solid (0.217 g, 70% overall); (Found: C, 50.7; H, 5.65; N, 9.0. $C_{13}H_{16}F_2N_2O_2$.HCl requires C, 50.9; H, 5.6; N, 9.1%); $\delta_H$ (400 MHz, DMSO-$d_6$) 9.39 (2H, br), 7.50 (1H, m), 7.18–7.12 (2H, m), 5.17 (2H, m, J 12.4 Hz), 4.29 (2H, m), 3.88 (1H, d, J 13 Hz), 3.24–3.03 (4H, m, J 13 Hz), 2.86 (1H, m, J 12.4 Hz), and 1.24 (3H, d, J 7.2 Hz).

Example 125

(R,R)-4-Difluoromethoxybenzyl 2,6-dimethylpiperazine-1-carboxylate (S)N-Benzyl-1-amino-2-propanol hydrochloride: a mixture of (S) 1-amino-2-propanol (9.0 g), benzaldehyde (14.7 ml), magnesium sulfate and THF (200 ml) was stirred for 18 h then filtered and concentrated in vacuo. The residue was dissolved in ethanol (200 ml) and sodium borohydride (1.1 g) was added. The mixture was stirred for 2 h then a further portion of sodium borohydride (1.1 g) was added. The mixture was stirred for 18 h then concentrated in vacuo. The residue was partitioned between dilute hydrochloric acid (2M, 200 ml) and ether (100 ml). The aqueous layer was basified with sodium hydroxide solution and extracted with two portions of ethyl acetate (100 ml). The combined ethyl acetate layers were washed (water), dried (sodium sulfate) and concentrated in vacuo. The residue was dissolved in ether (50 ml) and HCl-dioxane (4M, 35 ml) was added dropwise. The precipitate was filtered off, washed with ether and dried to give the product as a white solid (17.0 g); $\delta_H$ (400 MHz, DMSO-$d_6$) 9.43 (1H, m), 9.12 (1H, m), 7.58 (2H, dd, J 7.5, 2 Hz), 7.45–7.39 (3H, m), 5.35 (1H, m), 4.14 (2H, s), 4.01 (1H, m), 2.87 (1H, d, J 12 Hz), 2.67 (1H, t, J 8.5 Hz) and 1.08 (3H, d, J 6 Hz); HPLC [XTERRA; $NH_4OAc_{(aq)}$-MeOH (9:1)] 97% (1.08 min).

(S)N-Benzyl-1-amino-2-propanol (R)N-tert-butoxycarbonyl-alanine amide: carbonyldiimidazole (12.1 g) was added to a stirred solution of (R)N-tert-butoxycarbonyl-alanine (14.1 g) in DCM (200 ml). The mixture was stirred for 90 min then (S)N-benzyl-1-amino-2-propanol hydrochloride (15.0 g) was added portionwise. The mixture was stirred for 96 h then concentrated in vacuo. The residue was purified by flash column chromatography [$SiO_2$; ethyl acetate-isohexane(1:1)] to give the product as a gum (11.5 g); $\delta_H$ (400 MHz, $CDCl_3$) 7.39–7.16 (5H, m), 5.37 (1H, m), 4.90–4.55 (3H, m), 4.09 (0.5H, m), 3.97 (0.5H, m), 3.59 (1H, m), 3.42 (1H, m), 3.22 (1H, m), 1.44 (4.5H, s), 1.42 (4.5H, s), 1.36 (1.5H, d, J 6.5 Hz), 1.26 (1.5H, d, J 6.5 Hz), 1.20 (1.5H, d, J 6 Hz) and 1.12 (1.5H, d, J 6 Hz); HPLC (XTERRA, 50/80, 220 nm) 97% (1.77 min).

(R,R) 1-Benzyl-3,5-dimethylpiperazine-2-one: trifluoroacetic acid (50 ml) was added dropwise to a stirred solution of (S)N-benzyl-1-amino-2-propanol (R)N-tert-butoxycarbonyl-alanine amide (10.7 g) in DCM (100 ml) at 0° C. The mixture was stirred for 2 h then concentrated in vacuo. The residue was partitioned between sodium hydroxide solution (2M, 200 ml) was dichloromethane (200 ml). The organic layer was washed (water), dried (sodium sulfate) and concentrated in vacuo to give a viscous oil (7.15 g). To the oil were added triphenylphosphine (9.4 g) and THF (150 ml) and the stirred mixture was cooled to 0° C. under Ar. To the stirred solution was added di-tert-butyldiazodicarboxylate (8.6 g). The mixture was warmed to room temperature, stirred for 18 h then concentrated in vacuo. Dilute hydrochloric acid (1M, 100 ml) and conc. hydrochloric acid (10 ml) were added to the mixture. The mixture was stirred for 3 h then filtered. The filtrate was washed with ether (50 ml) then made basic using sodium hydroxide solution and extracted with two portions of ethyl acetate (100 ml). The combined ethyl acetate extracts were washed (water, brine), dried (sodium sulfate), concentrated in vacuo and purified by flash column chromatography [$SiO_2$; ethyl acetate-methanol-$NH_4OH$ (95:5)→(79:20:1)] to give the product as clear oil (1.38 g); $\delta_H$ (400 MHz, $CDCl_3$) 7.35–7.22 (5H, m), 4.66 (1H, d, J 14.5 Hz), 4.49 (1H, d, J 14.5 Hz), 3.78 (1H, q, J 7 Hz), 3.33 (1H, m), 3.16 (1H, dd, J 12, 4 Hz), 2.97 (1H, dd, J 12, 9 Hz) and 1.49 (3H, d, J 7 Hz); LC 96%, 0.67 min.

(R,R) 1-Benzyl-3,5-dimethylpiperazine: a solution of (R,R) 1-benzyl-3,5-dimethylpiperazine-2-one (1.3 g) in THF (10 ml) was added dropwise to a stirred suspension of lithium aluminium hydride (0.68 g) in THF (30 ml) at 0° C. under Ar. The mixture was stirred for 30 min then heated under reflux for a further 18 h. The mixture was cooled to 0° C. and diluted with ether (50 ml). To the stirred mixture were added water (2 ml) sodium hydroxide solution (2 ml) and water (2 ml). The mixture was stirred for 1 h then filtered through a pad of kieselguhr, washing with DCM. The filtrate was concentrated in vacuo to give the product as a clear oil (0.99 g); $\delta_H$ (400 MHz, $CDCl_3$) 7.35–7.20 (5H, m), 3.48 (1H, d, J 13 Hz), 3.38 (1H, d, J 13 Hz), 3.19 (1H, m), 2.49 (2H, dd, J 10.5, 3 Hz), 2.09 (2H, dd, J 10, 6.5 Hz) and 1.14 (6H, d, J 6.5 Hz); LC 93%, 1.91 min.

(R,R) 2,6-Dimethylpiperazine dihydrochloride: a mixture of (R,R) 4-Benzyl-2,6-dimethylpiperazine (0.95 g), palladium hydroxide/carbon (20%, 0.35 g) and methanol (30 ml) was shaken under hydrogen (45 p.s.i.) for 18 h. The mixture was filtered through a pad of kieselguhr, washing with methanol. The filtrate was treated with HCl-dioxane (4M, 5 ml), left to stand for 30 min then concentrated in vacuo. The residue was crystallised under diisopropyl ether to give the product as an off-white crystalline solid (0.17 g); $\delta_H$ (400 MHz, DMSO-$d_6$) 10.02–9.72 (4H, m), 3.72 (2H, m), 3.33 (2H, dd, J 13.5, 4 Hz), 3.15 (2H, dd, J 13.5, 7 Hz) and 1.40 (6H, d, J 7 Hz); $\delta_C$ (167 MHz, DMSO-$d_6$) 43.8, 43.7 and 14.3.

(R,R) 1-Chlorocarbonyl-2,6-dimethyl-4-tert-butoxycarbonylpiperazine; to a stirred mixture of (R,R) 2,6-dimethylpiperazine dihydrochloride (0.50 g) and triethylamine (0.93 ml) in DCM (50 ml) at 0° C. was added dropwise a solution of di-tert-butyl-dicarbonate (0.58 g) in DCM (5 ml). The mixture was warmed to room temperature, stirred for 2 h then concentrated in vacuo. The residue was dissolved in ethyl acetate, filtered through a PTFE membrane and concentrated in vacuo to give a clear oil (0.47 g). To the oil were added pyridine (0.6 ml) and DCM (6 ml). The mixture was added dropwise to a stirred solution of triphosgene (0.25 g) in DCM (20 ml) at 0° C. The mixture was stirred for 1 h, washed with two portions of water (20 ml) then dried over sodium sulfate and concentrated in vacuo to give the product as a yellow oil (0.43 g); $\delta_H$ (400 MHz, $CDCl_3$) 4.29 (1.6H, m), 4.07 (0.4H, m), 3.62 (2H, m), 3.54 (2H, m), 1.49 (7H, s), 1.48 (2H, s), 1.37 (2.5H, m) and 1.23 (0.5H, m).

(R,R) 4-Difluoromethoxybenzyl-2,6-dimethylpiperazine-1-carboxylate fumarate was prepared from (R,R) 1-chlorocarbonyl-2,6-dimethyl-4-tert-butoxycarbonylpiperazine (0.20 g) and 4-difluoromethoxybenzyl alcohol (0.13 g) according to the procedures described for Example 48 to give the product as a white solid (0.14 g); $\delta_H$ (400 MHz, DMSO-$d_6$) 7.43 (2H, d, J 9 Hz), 7.23 (1H, t, J 74 Hz), 7.18 (2H, d, J 9 Hz), 6.53 (2H, s), 5.10 (1H, d, J 12.5 Hz), 5.03 (1H, d, J 12.5 Hz), 3.92 (2H, m), 3.16 (2H, dd, J 13, 4 Hz), 2.84 (2H, dd J 12.5, 3.5 Hz) and 1.23 (6H, d, J 6.5 Hz); HPLC (XTERRA, 50/80, 220 nm) 96% (1.22 min).

Example 126

(R)-2-Fluoro-5-(2-propenyl)oxybenzyl 2-methylpiperazine-1-carboxylate

In a sealed 7 mL glass vial a mixture of 2-fluoro-5-hydroxybenzyl alcohol (50 mg, 0.35 mmol), PS-BEMP (2 g, 2.2 mmol/g, 0.46 mmol) and acetonitrile (3 mL) was shaken for 30 minutes. allyl bromide (18 uL, 0.22 mmol) was added and the mixture was shaken for 18 h. The mixture was filtered through a PTFE frit, washing with dichloromethane. The filtrate was concentrated under vacuum to give the product as a colourless oil which was used without further purification.

To a stirred solution of disuccinimidyl carbonate (3 mmol) in acetonitrile (18 mL) was added 2-fluoro-5-(2-propenyl)benzyl alcohol (3 mmol) then triethylamine (6 mmol). The mixture was stirred for 150 minutes at room temperature. To a polypropylene 10 mL tube were sequentially added (R) 2-methylpiperazine loaded resin (0.2 g, 0.05 mmol) and a portion of the benzyl alcohol/DSC mixture (3 mL, 5 mmol). The mixture was heated to 60° C. and agitated for 16 h. The mixture was cooled to room temperature then drained. The resin was washed 3× each with THF, methanol and dichloromethane using the following automated sequence: 5 mL solvent added, wash for 5 minutes, drain for 2 minutes. To the washed resin was added 5% trifluoroacetic acid in dichloromethane (5 mL). The mixture was agitated for 1 h then drained. More TFA/DCM (5 mL) was added and the mixture was agitated for a further hour then drained again. The combined TFA/DCM washes were concentrated under vacuum to give the product as a pale brown solid (7.5%); HPLC (XTERRA, 50/80, 220 nm) 86.2% (1.91 min); NMR $\delta_H$ (400 MHz, DMSO-$d_6$) 1.149(3H, d, J 7.0 Hz), 2.455(1H, td, J 3.5, 8.5 Hz), 2.676(2H, d, J 3.0 Hz), 2.834(1H, bdd), 2.938(1H, td), 3.645(1H, dd), 4.045(1H, m), 4.542(2H, dt, J 1.5, 5.5 Hz), 5.064(2H, m), 5.240(1H, m), 5.380(1H, m), 6.020(1H, m), 6.937(2H, m) and 7.136 (1H, t, J 9.0 Hz).

Example 127

2-Fluoro-5-(2-propenyl)oxybenzyl cis-2,6-dimethylpiperazine-1-carboxylate was prepared from 2-fluoro-5-hydroxybenzyl alcohol, allyl bromide and 1-chlorocarbonyl-cis-2,6-dimethyl-4-tert-butoxycarbonylpiperazine according to the methods described for Examples 54 and 121 to give the product as a yellow oil (8.4%); HPLC (XTERRA, 50/80, 220 nm) 95.7% (2.87 min); NMR $\delta_H$ (400 MHz, DMSO-$d_6$) 1.183(6H, d, J 6.5 Hz), 2.673(4H, m), 3.294(2H, bs), 3.910 (2H, m), 4.572(2H, m), 5.078(2H, s), 5.252(1H, m), 5.371 (1H, m), 6.022(1H, m), 6.948(2H, m) and 7.138(1H, t, J 9.5 Hz).

Example 128

5-Cyclohexylmethoxy-2-fluorobenzyl cis-2,6-dimethylpiperazine-1-carboxylate was prepared from 2-fluoro-5-hydroxybenzyl alcohol, cyclohexylmethyl bromide and 1-chlorocarbonyl-cis-2,6-dimethyl-4-tert-butoxycarbonylpiperazine according to the methods described for Examples 54 and 121 to give the product as a yellow oil (10.8%); HPLC (XTERRA, 50/80, 220 nm) 91.4% (6.77 min); NMR $\delta_H$ (400 MHz, DMSO-$d_6$) 1.016(2H, m), 1.204 (8H, m), 1.735(5H, m), 2.681(4H, m), 3.291(2H, s), 3.737 (2H, d, J 6.5 Hz), 3.905(2H, m) 5.078(2H, s), 6.931(2H, m) and 7.119(1H, t, J 9.0 Hz).

Example 129

2-Fluoro-5-(2-phenyl)ethoxybenzyl cis-2,6-dimethylpiperazine-1-carboxylate was prepared from 2-fluoro-5-hydroxybenzyl alcohol, 2-phenylethyl bromide and 1-chlorocarbonyl-cis-2,6-dimethyl-4-tert-butoxycarbonylpiperazine according to the methods described for Examples 54 and 121 to give the product as a yellow oil (2.2%); HPLC (XTERRA, 50/80, 220 nm) 87.7% (5.58 min); NMR $\delta_H$ (400 MHz, DMSO-$d_6$) 1.168(6H, d, J 7.0 Hz), 2.685(4H, m), 3.020(2H, t, J 7.0 Hz), 3.915(2H, m), 4.175(2H, t, J 7.0 Hz), 5.079(2H, s), 6.940(2H, m), 7.132(1H, t, J 9.0 Hz), 7.224 (1H, m) and 7.308(4H, m).

Example 130

2-Fluoro-5-(3-phenyl)propoxybenzyl piperazine-1-carboxylate was prepared from 2-fluoro-5-hydroxybenzyl alcohol, 3-phenylpropyl bromide and piperazine resin according to the methods described for Example 126 to give the product as a yellow oil (12.8%); HPLC (XTERRA, 50/80, 220 nm) 95.6% (5.30 min); NMR $\delta_H$ (400 MHz, DMSO-$d_6$) 2.006 (2H, m), 2.621 (4H, bs), 2.727 (2H, t, J 7.5 Hz), 3.282 (5H, bt), 3.936 (2H, t, J 6.5 Hz), 5.068 (2H, s), 6.932 (2H, m) and 7.167 (6H, m).

Example 131

(R)-2-Fluoro-5-(3-phenyl)propoxybenzyl 2-methylpiperazine-1-carboxylate was prepared from 2-fluoro-5-hydroxybenzyl alcohol, 3-phenylpropyl bromide and (R)-2-methylpiperazine resin according to the methods described for Example 126 to give the product as a yellow oil (6.5%); HPLC (XTERRA, 50/80, 220 nm) 89.0% (5.68 min); NMR $\delta_H$ (400 MHz, DMSO-$d_6$) 1.142 (3H, d. J 7.0 Hz), 2.001 (2H, m), 2.439 (1H, m), 2.657 (2H, m), 2.730 (2H, t, J 6.5 Hz), 2.845 (1H, bd), 2.930 (2H, bt), 3.633 (1H, bd), 3.939 (2H, t, J 6.5 Hz), 4.010 (1H, m), 5.065 (2H, m), 6.922 (2H, m) and 7.207 (6H, m).

Example 132

2-Fluoro-5-(3-phenyl)propoxybenzyl cis-2,6-dimethylpiperazine-1-carboxylate was prepared from 2-fluoro-5-hydroxybenzyl alcohol, 3-phenylpropyl bromide and 1-chlorocarbonyl-cis-2,6-dimethyl-4-tert-butoxycarbonylpiperazine according to the methods described for Examples 54 and 121 to give the product as a yellow oil (2.3%); HPLC (XTERRA, 50/80, 220 nm) 91.1% (6.29 min); NMR $\delta_H$ (400 MHz, DMSO-$d_6$) 7.32–7.10 (6H, m), 6.95 (1H, q, J 3 Hz), 6.91 (1H, dt, J 9, 4 Hz), 5.08 (2H, s), 3.93 (2H, t, J 6.5 Hz), 3.91 (2H,m), 2.73 (2H, t, J 7 Hz), 2.71 (2H, d, J 8.5 Hz), 2.65 (2H, dd, J 12.5, 4.5 Hz), 2.00 (2H, m) and 1.18 (6H, d, J 7 Hz).

Example 133

2-Fluoro-5-(3-trifluoromethylbenzyl)oxybenzyl cis-2,6-dimethylpiperazine-1-carboxylate was prepared from 2-fluoro-5-hydroxybenzyl alcohol, 3-trifluoromethylbenzyl bromide and 1-chlorocarbonyl-cis-2,6-dimethyl-4-tert-butoxycarbonylpiperazine according to the methods described for Examples 54 and 121 to give the product as a yellow oil (10.5%); HPLC (XTERRA, 50/80, 220 nm) 96.9% (6.20 min); NMR $\delta_H$ (400 MHz, DMSO-$d_6$) 1.164(6H, d, J 6.5 Hz), 2.668(4H, m), 3.889(2H, m), 5.082(2H, s), 5.199(2H, s), 7.057(2H, m), 7.175(1H, t, J 6.5 Hz) and 7.688(4H, m).

Example 134

2-Fluoro-5-(2-pyridylmethyl)oxybenzyl cis-2,6-dimethylpiperazine-1-carboxylate was prepared from 2-fluoro-5-hydroxybenzyl alcohol, 2-pyridylmethyl chloride hydrochloride and 1-chlorocarbonyl-cis-2,6-dimethyl-4-tert-butoxycarbonylpiperazine according to the methods described for Examples 54 and 121 to give the product as a yellow oil (10.4%); HPLC (XTERRA, 50/80, 220 nm) 91.1% (2.02 min); NMR $\delta_H$ (400 MHz, DMSO-$d_6$) 1.174 (6H, d, J 6.5 Hz), 2.676 (4H, m), 3.902 (2H, m), 5.069 (2H, s), 5.165 (2H, s), 7.018 (2H, m), 7.161 (1H, t, J 9.0 Hz), 7.350 (1H, m), 7.493 (1H, d, J 7.0 Hz), 7.825 (1H, m) and 8.575 (1H, m).

Example 135

2-Fluoro-5-(3-pyridylmethyl)oxybenzyl cis-2,6-dimethylpiperazine-1-carboxylate was prepared from 2-fluoro-5-hydroxybenzyl alcohol, 3-pyridylmethyl chloride hydrochloride and 1-chlorocarbonyl-cis-2,6-dimethyl-4-tert-butoxycarbonylpiperazine according to the methods described for Examples 54 and 121 to give the product as a yellow oil (5.4%); HPLC (XTERRA, 50/80, 220 nm) 91% (1.64 min); $\delta_H$ (400 MHz, DMSO-$d_6$) 1.172 (6H, d, J 7.0 Hz), 2.673 (4H, m), 3.294 (3H, s), 3.900 (2H, m), 5.075 (2H, s), 5.138 (2H, s), 7.052 (2H, m), 7.172 (1H, t, J 9.0 Hz), 7.424 (1H, m), 7.849 (1H, m), 8.546 (1H, m) and 8.654 (1H, m).

Example 136

(+/−)-2,6-Difluoro-4-(2-pyridylmethyl)oxybenzyl 2-methylpiperazine-1-carboxylate was prepared from 2,6-difluoro-4-hydroxybenzyl alcohol, 2-pyridylmethyl chloride hydrochloride and (+/−) 2-methylpiperazine resin according to the methods described for Example 126 to give the product as a yellow oil: $\delta_H$ (400 MHz, DMSO-$d_6$) 1.19 (3H, d, J 7.1 Hz), 2.85 (1H, m), 3.05–3.20 (4H, m), 3.90 (1H, m), 4.35 (1H, m), 5.10 (2H, m), 5.28 (2H, s), 6.92 (2H, m), 7.48 (1H, m), 7.62 (1H, m), 7.96 (1H, m), 8.65 (1H, m) and 9.15 (1H, br); HPLC (XTERRA, 50/80, 220 nm) 92% (1.35 min).

Example 137

(+/−)-2,6-Difluoro-4-(3-pyridylmethyl)oxybenzyl 2-methylpiperazine-1-carboxylate was prepared from 2,6-difluoro-4-hydroxybenzyl alcohol, 3-pyridylmethyl chloride hydrochloride and (+/−) 2-methylpiperazine resin according to the methods described for Example 126 to give the product as a yellow oil: $\delta_H$ (400 MHz, DMSO-$d_6$) 1.19 (3H, d, J 7.1 Hz), 2.85 (1H, m), 3.05–3.20 (4H, m), 3.90 (1H, m), 4.35 (1H, m), 5.10 (2H, m), 5.28 (2H, s), 6.92 (2H, m), 7.78 (1H, m), 8.25 (1H, m), 8.78 (1H, m), 8.84 (1H, m) and 9.20 (1H, br); HPLC (XTERRA, 50/80, 220 nm) 90.5% (1.12 min).

Example 138

(+/−)-2-Methyl-piperazine-1-carboxylic acid 4-(3,5-dimethyl-isoxazol-4-ylmethoxy)-2,6-difluoro-benzyl ester was prepared from 2,6-difluoro-4-hydroxybenzyl alcohol, 4-(3,5-dimethylisoxazolylmethyl chloride and (+/−) 2-methylpiperazine resin according to the methods described for Example 126 to give the product as a yellow oil: $\delta_H$ (400 MHz, DMSO-$d_6$) 1.20 (3H, d, J 7.1 Hz), 2.22 (3H, s), 2.42 (3H, s), 2.85 (1H, m), 3.05–3.20 (4H, m), 3.90 (1H, m), 4.35 (1H, m), 5.0 (2H, s), 5.10 (2H, m), 6.89 (2H, m), 8.60 (1H, br) and 9.20 (1H, br); HPLC (XTERRA, 50/80, 220 nm) 87.7% (1.61 min).

Example 139

5-tert-Butylaminocarbonyloxy-2-fluorobenzyl cis-2,6-dimethylpiperazine-1-carboxylate hydrochloride 2-Fluoro-5-[2-(trimethylsilyl)ethoxymethoxy]benzyl alcohol: to a stirred mixture of 2-fluoro-5-hydroxybenzaldehyde (0.28 g), N,N-di-isopropylethylamine (0.52 ml) and DCM (2 ml) at 0° C. was added dropwise 2-(trimethylsilyl) ethoxymethyl chloride (0.45 ml). The mixture was stired 1 h then partitioned between DCM (25 ml) and water (25 ml). The organic layer was washed (water, brine), dried (sodium sulfate) and concentrated in vacuo. The residue was dissolved in 2-propanol (20 ml) and sodium borohydride (0.15 g) was added. The mixture was stirred 1 h then partitioned between isopropyl ether (2×50 ml) and water (50 ml). The combined organics were washed (water), concentrated in vacuo and purified by column chromatography [$SiO_2$; DCM-isopropyl ether(1:0→0:1)] to give the product as a colourless oil (0.54 g, 99%) which was used without further purification.

2-Fluoro-5-[2-(trimethylsilyl)ethoxymethoxy]benzyl-4-tert-butoxycarbonyl-cis-2,6-dimethylpiperazine-1-carboxylate was prepared from 2-fluoro-5-[2-(trimethylsilyl) ethoxymethoxy]benzyl alcohol and 1-chlorocarbonyl-2,6-dimethyl-4-tert-butoxycarbonylpiperazine according to the procedures described for Example 54 to give the product as a clear oil which was used immediately without further purification.

2-Fluoro-5-hydroxybenzyl-cis-2,6-dimethylpiperazine-1-carboxylate hydrochloride: a mixture of crude 2-fluoro-5-[2-(trimethylsilyl)ethoxymethoxy]benzyl-4-tert-butoxycarbonyl-cis-2,6-dimethylpiperazine-1-carboxylate (0.61 g) hydrogen chloride solution (4.0 M, dioxane, 2 ml) and methanol (4 ml) was stirred for 3 h then concentrated in vacuo. The residue was left to stand under ether (10 ml) for 1 h; the white precipitate was filtered off, washed with ether and dried to give the product as a white solid (0.23 g, 71%): $\delta_H$ (400 MHz, DMSO-$d_6$) 9.84 (1H, br), 9.51 (1H, br), 9.15 (1H, br), 7.01 (1H, t, J 9 Hz), 6.81 (1H, dd, J 6, 3 Hz), 6.73 (1H, m), 5.08 (2H, s), 4.30 (2H, m), 3.16 (2H, d, J 11 Hz), 3.10 (2H, m) and 1.30 (6H, d, J 7 Hz).

2-Fluoro-5-hydroxybenzyl-cis-2,6-dimethyl-4-tert-butylcarbonylpiperazine-1-carboxylate: to a stirred solution of 2-fluoro-5-hydroxybenzyl-cis-2,6-dimethylpiperazine-1-carboxylate (free-base, 1.93 g) in DCM (70 ml) was added dropwise di-tert-butyl di-carbonate (1.68 ml). The mixture was stirred for 18 h then concentrated in vacuo and purified by column chromatography [$SiO_2$; isopropyl ether-isohexane (2:3→1:0)] to give the product as a white solid (2.24 g, 84%): $\delta_H$ (400 MHz, DMSO-$d_6$) 6.92 (1H, t, J 9 Hz), 6.87 (1H, m), 6.76 (1H, m), 6.10 (1H, m, OH), 5.15 (2H, s), 4.20 (2H, t, J 5.5 Hz), 3.93 (2H, m), 2.97 (2H, m), 1.48 (9H, s) and 1.23 (6H, d, J 7 Hz); HPLC XTERRA, 50–80%, 220 nm, 98.5% (4.86 min).

5-tert-Butylaminocarbonyloxy-2-fluorobenzyl-4-tert-butoxycarbonyl-cis-2,6-dimethylpiperazine-1-carboxylate: triethylamine (0.02 ml) was added to a stirred mixture of 2-fluoro-5-hydroxybenzyl-cis-2,6-dimethyl-4-tert-butylcarbonylpiperazine-1-carboxylate (0.19 g) and tert-butylisocyanate (0.12 ml) in DCM (2 ml). The mixture was stirred 18 h the concentrated in vacuo and purified by column chromatography [$SiO_2$: isopropyl ether-isohexane (2:3→1:0)] to give the product as a colourless partially solidified gum (0.2445 g, 102%). Rf (Silica, isopropyl ether) 0.20; $\delta_H$ (400 MHz, $CDCl_3$) 7.14 (1H, m), 7.06–7.03 (2H, m), 5.18 (2H, s), 4.98 (1H, br), 4.20 (2H, br), 3.96 (1H, br), 3.87 (1H, br), 3.00 (1H, br), 2.93 (1H, br), 1.48 (9H, s), 1.38 (9H, s), and 1.24 (6H, d, J 6.4 Hz).

5-tert-Butylaminocarbonyloxy-2-fluorobenzyl cis-2,6-dimethylpiperazine-1-carboxylate hydrochloride was prepared from 5-tert-butylaminocarbonyloxy-2-fluorobenzyl-4-tert-butoxycarbonyl-cis-2,6-dimethylpiperazine-1-carboxylate according to the method described for Example 52 to give the product as a white solid (0.1538 g, 72% overall); (Found: C, 54.4; H, 7.0; N, 9.9%. $C_{19}H_{28}FN_3O_4$.HCl requires C, 54.6; H, 7.0; N, 10.05%); $\delta_H$ (400 MHz, DMSO-$d_6$) 9.8 (1H, br), 9.2 (1H, br), 7.64 (1H, s), 7.24 (1H, t, J 9.2 Hz), 7.18 (1H, m), 7.11 (1H, br), 5.15 (2H, s), 4.30 (2H, m, J 6 Hz), 3.16 (2H, d, J 13 Hz), 3.07 (2H, dd, J 5 and 13 Hz), and 1.30–1.27 (15H, m).

Example 140

2-Fluoro-5-(4-difluoromethoxybenzyl)oxybenzyl cis-2,6-dimethylpiperazine-1-carboxylate hydrochloride was prepared from 2-fluoro-5-hydroxybenzyl alcohol, 4-difluoromethoxybenzyl chloride and 1-chlorocarbonyl-2,6-dimethyl-4-tert-butoxycarbonylpiperazine according to the methods described for Examples 52 and 54 to give the product as a white solid (0.224 g, 94% overall); (Found: C, 55.7; H, 5.7; N, 5.9. $C_{22}H_{25}F_3N_2O_4$.HCl requires C, 55.6; H, 5.5; N, 5.9%); $\delta_H$ (400 MHz, DMSO-$d_6$) 9.8 (1H, br), 9.3 (1H, br), 7.50 (2H, d, J 8.4 Hz), 7.26(1H, t, J 74 Hz), 7.21–7.15 (3H, m), 7.09 (1H, m), 7.03 (1H, m, J 3.2 Hz), 5.12 (2H, s), 5.08 (2H, s), 4.28 (2H, m, J 6 Hz), 3.15 (2H, d, J 13 Hz), 3.06 (2H, dd, J 5 and 13 Hz), and 1.29 (6H, d, J 7.2 Hz).

Example 141

Piperazine-1-carboxylic acid 2,6-difluoro-4-(5-thiophen-2-yl-[1,2,4]oxadiazol-3-ylmethoxy)-benzyl ester was prepared from 2,6-difluoro-4-hydroxybenzyl alcohol, 3-chloromethyl-5-thiophen-2-yl-[1,2,4]oxadiazole and piperazine resin according to the methods described for Example 126 to give the product as a yellow oil: $\delta_H$ (400 MHz; $d_6$-DMSO) 2.60 (4H, br s), 3.30 (4H, br s), 5.04 (2H, s), 5.42 (2H, s), 6.92–7.01 (2H, m), 7.36 (1H, dd, J 5.0, 4 Hz), 8.06 (1H, dd, J 4, 1 Hz) and 8.12 (1H, dd, J 5.0, 1 Hz); HPLC (XTERRA, 50–80%, 235 nm) 99.4% (3.71 min).

Example 142

(R)-2-Methyl-piperazine-1-carboxylic acid 2,6-difluoro-4-(5-thiophen-2-yl-[1,2,4]oxadiazol-3-ylmethoxy)-benzyl ester was prepared from 2,6-difluoro-4-hydroxybenzyl alcohol, 3-chloromethyl-5-thiophen-2-yl-[1,2,4]oxadiazole and (R) 2-methylpiperazine resin according to the methods described for Example 126 to give the product as a yellow oil: $\delta_H$(400 MHz; $d_6$-DMSO) 1.10 (3H, d, J 7.0 Hz), 2.40 (1H, td, J 12.0, 3.5 Hz), 2.62 (2H, br d, J, 2.5 Hz), 2.75–2.82 (1H, br d, J 12 Hz), 2.88 (1H, td, J 12.5, 3.5 Hz), 3.55 (1H, br d, J 12 Hz), 3.96 (1H, br s), 5.02 (1H, d, J 12.5 Hz), 5.07 (1H, d, J 12.5 Hz), 5.42 (2H, s), 6.93–7.01 (2H, m), 7.36(1H, dd, J 5.0 and 4 Hz), 8.06 (1H, dd, J4, 1.0 Hz) and 8.12 (1H, dd, J 5.0, 1 Hz); HPLC (XTERRA, 50–80%, 235 nm) 99.8% (4.22 min).

Example 143 cis-2,6-Dimethyl-piperazine-1-carboxylic acid 2,6-difluoro-4-(5-thiophen-2-yl-[1,2,4]oxadiazol-3-ylmethoxy)- benzyl ester was prepared from 2,6-difluoro-4-hydroxybenzyl alcohol, 3-chloromethyl-5-thiophen-2-yl-[1,2,4] oxadiazole and cis-1-chlorocarbonyl-2,6-dimethyl-4-tert-butoxycarbonylpiperazine according to the methods described for Example 54 and 121 to give the product as a yellow oil: $\delta_H$(400 MHz; $d_6$-DMSO) 1.14 (6H, d, J 6.5 Hz), 2.60 (2H, dd, J 12, 5 Hz), 2.66 (2H, d, J 12 Hz), 3.77–3.87 (2H, m), 5.05 (2H, s), 5.42 (2H, s), 6.93–7.01 (2H, m), 7.36 (1H, dd, J 5.0, 4 Hz), 8.06 (1H, dd, J 4, 1.0 Hz) and 8.12 (1H, dd, J 5.0, 1.0 Hz); HPLC (XTERRA, 50–80%, 235 nm) 99.4% (5.04 min).

Example 144

2,6-Difluoro-4-(3-fluorobenzyl)oxybenzyl cis-2,6-dimethylpiperazine-1-carboxylate was prepared from 2,6-difluoro-4-hydroxybenzyl alcohol, 3-fluorobenzyl chloride and 1-chlorocarbonyl-2,6-dimethyl-4-tert-butoxycarbonylpiperazine according to the methods described for Example 54 and 121 to give the product as a yellow oil: $\delta_H$ (400 MHz; $d_6$-DMSO) 1.13 (6H, d, J 7.0 Hz), 2.60 (2H, dd, J 12, 4.5 Hz), 2.66 (2H, d, J 12 Hz), 3.77–3.86 (2H, m), 5.03 (2H, s), 5.18 (2H, s), 6.84–6.93 (2H, m), 7.16–7.22 (1H, m), 7.27–7.32 (2H, m) and 7.42–7.49 (1H, m); HPLC (XTERRA, 50–80%, 220 nm) 99.8% (5.96 min).

Example 145

2,6-Difluoro-4-(3,4-difluorobenzyl)oxybenzyl cis-2,6-dimethylpiperazine-1-carboxylate was prepared from 2,6-difluoro-4-hydroxybenzyl alcohol, 3,4-difluorobenzyl chloride and 1-chlorocarbonyl-2,6-dimethyl-4-tert-butoxycarbonylpiperazine according to the methods described for Example 54 and 121 to give the product as a yellow oil: $\delta_H$ (400 MHz; $d_6$-DMSO) 1.13 (6H, d, J 7.0 Hz), 2.60 (2H, dd, J 12.0, 4.5 Hz), 2.66 (2H, d, J 12.0 Hz), 3.77–3.85 (2H, m), 5.04 (2H, s), 5.13 (2H, s), 6.84–6.92 (2H, m), 7.29–7.35 (1H, m), 7.48 (1H, dt, J 11.0, 8.5 Hz) and 7.55 (1H, ddd, J 11.5, 7.5, 2.5 Hz); HPLC (XTERRA, 50–80%, 220 nm) 99.5% (6.17 min).

Example 146

2-Fluoro-5-(2,4-difluorobenzyl)oxybenzyl cis-2,6-dimethylpiperazine-1-carboxylate was prepared from 2,6-difluoro-4-hydroxybenzyl alcohol, 2,4-difluorobenzyl chloride and 1-chlorocarbonyl-2,6-dimethyl-4-tert-butoxycarbonylpiperazine according to the methods described for Example 54 and 121 to give the product as a yellow oil: $\delta_H$ (400 MHz; $d_6$-DMSO) 1.26 (6H, d, J 6.9 Hz), 2.75–2.90 (4H, m), 4.10 (2H, br), 4.98 (2H, s), 5.20 (2H, s), 6.85 (1H, m), 6.98 (2H, m) and 7.10–7.30 (3H, m), NH not observed; HPLC (XTERRA, 50/80%, 220 nm) 93.8% (5.68 min).

Example 147

2-Fluoro-5-(3,4-difluorobenzyl)oxybenzyl cis-2,6-dimethylpiperazine-1-carboxylate was prepared from 2,6-difluoro-4-hydroxybenzyl alcohol, 3,4-difluorobenzyl chloride and 1-chlorocarbonyl-2,6-dimethyl-4-tert-butoxycarbonylpiperazine according to the methods described for Example 54 and 121 to give the product as a yellow oil: $\delta_H$ (400 MHz; $d_6$-DMSO) 1.29 (6H, d, J 6.9 Hz), 2.77–2.90 (4H, m), 4.10 (2H, br), 5.04 (2H, s), 5.18 (2H, s), 6.80–7.02 (5H, m) and 7.42 (1H, m), NH not observed; HPLC (XTERRA, 50/80%, 220 nm) 89.5% (5.5 min).

Example 148

2,6-Difluoro-4-(3-furylmethyl)oxybenzyl cis-2,6-dimethylpiperazine-1-carboxylate fumarate 2,6-Difluoro-4-(furan-3-methoxy)benzyl alcohol: methanesulfonyl chloride (0.9 ml) was added dropwise to a stirred solution of 3-furan-methanol (1.0 g) and triethylamine (2.1 ml) in dichloromethane (30 ml) at 0° C. The mixture was stirred for 30 min. then warmed to room temperature and stirred for a further 2 h. The mixture was partitioned between ether (100 ml) and water (100 ml). The organic layer was washed (water, brine), dried (sodium sulfate) and concentrated in vacuo to give a pale yellow oil (0.77 g). To the oil were added 2,6-difluoro-4-hydroxybenzyl alcohol (0.56 g), cesium carbonate (1.1 g) and DMF (30 ml). The mixture was stirred for 18 h then partitioned between ethyl acetate (20 ml) and water (50 ml). The layers were separated; the aqueous layer was extracted with more ethyl acetate (20 ml). The combined organic layers were washed (water, brine), dried (sodium sulfate) and concentrated in vacuo. The residue was purified by flash column chromatography [$SiO_2$: isohexane-ethyl acetate (3:1)] to give the product as a clear oil (0.16 g); $\delta_H$ (400 MHz, $CDCl_3$) 7.51 (1H, d, J 1 Hz), 7.45 (1H, t, J 2 Hz), 6.54 (1H t, J 4 Hz), 6.50 (1H, t, J 4 Hz), 6.47 (1H, d, J 1.5 Hz), 4.91 (2H, s) and 4.71 (2H, d, J 6.5 Hz); HPLC (XTERRA, 50/80, 220 nm) 1.76 min (74%).

2,6-Difluoro-4-(3-furanmethoxy)benzyl-2,6-dimethylpiperazine-1-carboxylate fumarate: to a stirred suspension of sodium hydride (60%, 0.015 g) in DMF (1 ml) was added dropwise a solution of 2,6-difluoro-4-(furan-3-methoxy) benzyl alcohol (0.06 g) and cis 1-chlorocarbonyl- 2,6-dimethyl-4-tert-butoxycarbonylpiperazine (0.07 g) in DMF (2 ml). The mixture was stirred for 2 h then partitioned between ethyl acetate (20 ml) and water (20 ml). The organic layer was washed (water, brine), dried (sodium sulfate) and concentrated in vacuo to give a yellow oil (0.11 g). To the residue were added methanol (2 ml) and hydrogen chloride in dioxane (4M, 0.3 ml). The mixture was stirred for 4 h then partitioned between water (20 ml) and ether (20 ml). The aqueous layer was basified with aqueous sodium hydroxide solution (2M, 5 ml) and extracted with ethyl acetate (20 ml). The ethyl acetate layer was washed (water, brine), dried (sodium sulfate) and concentrated in vacuo to give a pale oil (0.036 g). To the oil were added fumaric acid (0.013 g) and 2-propanol (1 ml). The mixture was heated to reflux then cooled to room temperature and diluted with ether (5 ml). The emerging precipitate was filtered-off, washed (ether) and dried to give the product as a white solid (0.027 g); $\delta_H$ (400 MHz, DMSO-$d_6$) 7.81 (1H, t, J 1.5 Hz), 7.67 (1H, t, J 2 Hz), 6.86 (1H, t, J 3 Hz), 6.82 (1H, t, J 3 Hz), 6.59 (2H, s), 6.57 (1H, d, J 1.5 Hz), 5.04 (2H, s), 5.01 (2H, s), 3.95–3.86 (2H, m), 2.80–2.65 (4H, m) and 1.16 (6H, d, J 7 Hz); HPLC (XTERRA, 50/80, 220 nM) 82% (4.00 min).

Example 149

(+/−)-2,6-Difluoro-4-(3-furylmethyl)oxybenzyl 2-ethylpiperazine-1-carboxylate fumarate was prepared from 1-chlorocarbonyl-2,6-dimethyl-4-tert-butoxycarbonylpiperazine (0.07 g), and 2,6-difluoro-4-(furan-3-methoxy)benzyl alcohol (0.06 g) according to the procedures described for Example 148 to give the product as a white solid (0.03 g); □$_H$ (400 MHz, DMSO-$d_6$) 7.81 (1H, d, J 1 Hz), 7.67 (1H, t, J 2 Hz), 6.86 (1H, t, J 3.5 Hz), 6.82 (1H, t, J 3.5 Hz), 6.57 (3H, s), 4.07 (1H, d, J 11 Hz), 5.01 (2H, s), 5.00 (1H, d, J 11 Hz), 3.81 (1H, m), 2.91–2.80 (4H, m), 2.74–2.66 (1H, m), 2.59–2.50 (1H, m), 1.76–1.63 (1H, m), 1.61–1.48 (1H, m) and 0.73 (3H, t, J 7.5 Hz); HPLC (XTERRA, 50/80, 220 nM) 86% (3.71 min).

Example 150

(+/−)-piperazine-1-carboxylic acid 2,6-difluoro-4-(tetrahydro-furan-2-ylmethoxy)-benzyl ester fumarate (+/−)-[2,6-Difluoro-4-(tetrahydro-furan-2-ylmethoxy)-phenyl]-methanol: a stirred mixture of 2,6-difluoro-4-hydroxybenzyl alcohol (0.5 g), (+/−)-tetrahydrofurfuryl bromide (0.36 ml), cesium carbonate (0.56 g) and sodium iodide (0.005 g) in DMF (5 ml) was heated to 60° C. for 18 h then cooled to room temperature. The mixture was partitioned between ethyl acetate (30 ml) and aqueous sodium hydroxide solution (2M, 30 ml). The organic layer was washed (water, brine), dried (sodium sulfate) and concentrated in vacuo. The residue was purified by flash column chromatography [$SiO_2$; isohexane-ethyl acetate (4:1)] to give the product as a clear oil (0.17 g); $\delta_H$ (400 MHz, $CDCl_3$) 6.50 (1H, t, J 3.5 Hz), 6.46 (1H, t, J 3.5 Hz), 4.69 (2H, d, J 6.5 Hz), 4.28–4.21 (1H, m), 3.92 (2H, d, J 5 Hz), 3.92 (1H, dd, J 15, 6.5 Hz), 3.83 (1H, dt, J 15, 6.5 Hz), 2.12–2.03 (1H, m), 2.00–1.90 (2H, m), 1.83 (1H, t, J 6 Hz) and 1.78–1.69 (1H, m); HPLC (XTERRA, 50/80, 220 nM) 98% (0.91 min).

(+/−)-piperazine-1-carboxylic acid 2,6-difluoro-4-(tetrahydro-furan-2-ylmethoxy)-benzyl ester fumarate was prepared from 1-chlorocarbonyl-4-tert-butoxycarbonylpiperazine (0.076 g), and (+/−)-[2,6-Difluoro-4-(tetrahydro-furan-2-ylmethoxy)-phenyl]-methanol (0.075 g) according to the procedures described for Example 148 to give the product as a white solid (0.058 g); m.p. 199° C. (decomp.); Found: C, 52.81; H, 5.65; N, 5.78%. $C_{21}H_{26}F_2N_2O_8.0.25H_2O$ requires: C, 52.88; H, 5.60; N, 5.87%.

Example 151

(+/−)-Piperazine-1-carboxylic acid 2-fluoro-4-(tetrahydro-furan-2-ylmethoxy)-benzyl ester fumarate (+/−)-[2-Fluoro-4-(tetrahydro-furan-2-ylmethoxy)-phenyl]-methanol was prepared from 2-fluoro-5-hydroxybenzyl alcohol (0.50 g) and (+/−)-tetrahydrofurfuryl bromide (0.40 ml) according to the procedure described for Example 150 to give the product as a clear oil (0.17 g); $\delta_H$ (400 MHz, $CDCl_3$) □H 6.98 (1H, q, J 3 Hz), 6.94 (1H, t, J 9 Hz), 6.79 (1H, dt, J 9, 3 Hz), 4.71 (2H, d, J 4.5 Hz), 4.25 (1H, tt, J 7, 5 Hz), 3.94 (1H, dt, J 8.5, 6.5 Hz), 3.93 (2H, d, J 5 Hz), 3.82 (1H, dt, J 8.5, 7 Hz), 2.11–2.03 (1H, m), 2.01–1.88 (2H, m) and 1.80–1.71 (1H, m); HPLC (XTERRA, 50/80, 220 nM) 96% (0.88 min).

(+/−)-piperazine-1-carboxylic acid 2-fluoro-4-(tetrahydro-furan-2-ylmethoxy)-benzyl ester fumarate was prepared from (+/−)-[2-Fluoro-4-(tetrahydro-furan-2-ylmethoxy)-phenyl]-methanol (0.075 g) and 1-chlorocarbonyl-2,6-dimethyl-4-tert-butoxycarbonylpiperazine (0.092 g) using the procedures described in Example 148 to give the product as a white, crystalline solid (0.086 g); m.p. 141–147° C. (decomp.); Found: C, 57.01; H, 6.58; N, 5.98%. $C_{21}H_{27}FN_2O_8$ requires: C, 57.25; H, 6.48; N, 5.81%.

Example 152

2,6-Difluoro-4-(3-thienylmethyl)oxybenzyl cis-2,6-dimethylpiperazine-1-carboxylate fumarate

[2,6-Difluoro-4-(thiophen-3-ylmethoxy)-phenyl]-methanol: to a stirred solution of thiophene-3-methanol (1.0 g) and triethylamine (1.8 ml) in DCM (10 ml) at 0° C. was added dropwise methanesulfonyl chloride (0.75 ml). The mixture was warmed to room temperature and stirred for 2 h then washed with water (20 ml), filtered through a PTFE membrane and concentrated in vacuo. To the residue were added 2,6-difluoro-4-hydroxybenzyl alcohol (0.5 g), cesium carbonate (0.75 g), sodium iodide (0.01 g) and DMF (5 ml). The mixture was heated to 60° C. and stirred for 18 h. The mixture was cooled to room temperature then partitioned between ethyl acetate (40 ml) and water (20 ml). The organic layer was washed (water), dried (sodium sulfate) and concentrated in vacuo. The residue was purified by flash column chromatography [$SiO_2$; isohexane-ethyl acetate (4:1)] to give the product as a clear oil (0.68 g); $\delta_H$ (400 MHz, $CDCl_3$) 7.35 (1H, dd, J 5, 3 Hz), 7.31 (1H, m), 7.12 (1H, dd, J 5, 1.5 Hz), 6.54 (1H, t, J 3.5 Hz), 6.50 (1H, t, J 3.5 Hz), 5.04 (2H, s) and 4.70 (2H, d, J 6 Hz); HPLC (XTERRA, 50/80, 220 nM) 94% (2.51 min).

2,6-Difluoro-4-(3-thienylmethyl)oxybenzyl cis-2,6-dimethylpiperazine-1-carboxylate fumarate was prepared from [2,6-difluoro-4-(thiophen-3-ylmethoxy)-phenyl]-methanol (0.15 g) and cis 1-chlorocarbonyl-2,6-dimethyl-4-tert-butoxycarbonylpiperazine (0.16 g) according to the procedures described in Example 148 to give the product as a white, crystalline solid (0.084 g); m.p. 162–186° C. (decomp.); $\delta_H$ (400 MHz, DMSO-$d_6$) 7.61 (1H, m), 7.56 (1H, dd, J 5, 3 Hz), 7.17 (1H, dd, J 5, 1 Hz), 5.14 (2H, s), 5.04 (2H, s), 3.90 (2H, m), 2.76 (2H, t, J 11 Hz), 2.68 (2H, dd, J 12, 4.5 Hz) and 1.16 (6H, d, J 7 Hz).

Example 153

2,6-Difluoro-4-(3-thienylmethyl)oxybenzyl piperazine-1-carboxylate fumarate was prepared from [2,6-difluoro-4-(thiophen-3-ylmethoxy)-phenyl]-methanol (0.15 g) and 1-chlorocarbonyl-4-tert-butoxycarbonylpiperazine (0.15 g) according to the procedures described for Example 148 to give the product as a white, crystalline solid (0.084 g); m.p. 161–162° C. (decomp.); $\delta_H$ (400 MHz, DMSO-$d_6$) 7.62 (1H, dd, J 3, 1.5 Hz), 7.57 (1H, dd, J 5, 3 Hz), 7.17 (1H, dd, J 5, 1.5 Hz), 6.87 (1H, t, J 3.5 Hz), 6.83 (1H, t, J 3.5 Hz), 6.54 (2H, s), 5.14 (2H, s), 5.04 (2H, s), 3.35 (4H, m) and 2.77 (4H, m).

Example 154

(R)-2,6-Difluoro-4-(3-thienylmethyl)oxybenzyl 2-methylpiperazine-1-carboxylate fumarate was prepared from [2,6-difluoro-4-(thiophen-3-ylmethoxy)-phenyl]-methanol (0.15 g) and (R) 1-chlorocarbonyl-2-methyl-4-tert-butoxycarbonylpiperazine (0.15 g) according to the procedures described for Example 148 to give the product as a white, crystalline solid (0.028 g); m.p. 121–143° C. (decomp.); $\delta_H$ (400 MHz, DMSO-$d_6$) 7.62 (1H, dd, J 3, 1.5 Hz), 7.57 (1H, dd, J 5, 3 Hz), 7.17 (1H, dd, J 5, 1 Hz), 6.87 (1H, t, J 3.5 Hz), 6.83 (1H, t, J 3.5 Hz), 6.57 (2H, s), 5.14 (2H, s), 5.07 (1H, d, J 12 Hz), 5.01 (1H, d, J 12 Hz), 4.04 (1H, m), 3.63 (1H, m), 3.00–2.86 (3H, m), 2.76 (1H, m), 2.54 (1H, m) and 1.13 (3H, d, J 7 Hz).

Example 155

(+/−)-2,6-Difluoro-4-(3-thienylmethyl)oxybenzyl 2-ethylpiperazine-1-carboxylate fumarate was prepared from [2,6-difluoro-4-(thiophen-3-ylmethoxy)-phenyl]-methanol (0.15 g) and (+/−) 1-chlorocarbonyl-2-ethyl-4-tert-butoxycarbonylpiperazine (0.16 g) according to the procedures described for Example 148 to give the product as a white, crystalline solid (0.057 g); m.p. 133–134° C. (decomp.); $\delta_H$ (400 MHz, DMSO-$d_6$) 7.61 (1H, dd, J 3, 1.5 Hz), 7.56 (1H, dd, J 5, 3 Hz), 7.17 (1H, dd, J 4.5, 1 Hz), 5.14 (2H, s), 5.06 (1H, d, J 12 Hz), 5.01 (1H, d, J 12 Hz), 3.92–3.66 (2H, m), 2.94–2.80 (3H, m), 2.76–2.66 (1H, m), 2.62–2.50 (1H, m), 1.78–1.64 (1H, m), 1.63–1.48 (1H, m) and 0.72 (3H, d, J 7.5 Hz).

Example 156 cis-2,6-Dimethyl-piperazine-1-carboxylic acid 2,6-difluoro-4-(5-methyl-isoxazol-3-ylmethoxy)-benzyl ester was prepared from 2,6-difluoro-4-hydroxybenzyl alcohol, 3-chloromethyl-5-methyl-isoxazoleand 1-chlorocarbonyl-cis-2,6-dimethyl-4-tert-butoxycarbonylpiperazine according to the procedures described for Example 54 and 121 to give the product as a yellow oil: $\delta_H$ (400 MHz; $d_6$-DMSO) 1.14 (6H, d, J 6.5 Hz), 2.41 (H, d, J 1.0 Hz), 2.63 (2H, dd, J 12, 4.5 Hz), 2.68 (2H, d, J 12 Hz), 3.80–3.88 (2H, m), 5.04 (2H, s), 5.21 (2H, s), 6.34 (1H, d, J 1.0 Hz), and 6.84–6.92 (2H, m); HPLC (XTERRA, 50/80%, 220 nm) 96.8% (2.38 min).

Example 157 cis-2,6-Dimethyl-piperazine-1-carboxylic acid 2,6-difluoro-4-(5-methyl-3-phenyl-isoxazol-4-ylmethoxy)-benzyl ester was prepared from 2,6-difluoro-4-hydroxybenzyl alcohol, (5-methyl-3-phenyl-isoxazol-4-yl)-methanol and 1-chlorocarbonyl-cis-2,6-dimethyl-4-tert-butoxycarbonylpiperazine according to the procedures described for Example 54 and 121 to give the product as a yellow oil: $\delta_H$ (400 MHz; $d_6$-DMSO) 1.15 (6H, d, J 7.0 Hz), 2.53 (3H, s), 2.62 (2H, dd, J 12.0, 4.5 Hz), 2.68 (2H, d, J 12.0 Hz), 3.80–3.88 (2H, m), 5.01–5.08 (4H, m), 6.84–6.91 (2H, m), 7.48–7.53 (3H, m) and 7.64–7.68 (2H, m).

Example 158

(+/−)-2-Fluoro-5-(2-propenyl)oxybenzyl 2-ethylpiperazine-1-carboxylate fumarate was prepared from 2-fluoro-5-hydroxybenzyl alcohol, allyl bromide and (+/−) 2-ethyl-1-chlorocarbonyl-4-tert-butoxycarbonylpiperazine according to the procedures described for Example 148 to give the product as a white solid (5.1%); HPLC (XTERRA, 50–80%, 220 nm) 96.8% (2.30 min); NMR $\delta_H$ (400 MHz, DMSO-$d_6$) 0.765 (2H, t, J 7.5 Hz), 1.650 (2H, m), 2.708 (1H, m), 2.878 (2H, bt), 3.767 (1H, bd), 3.883 (1H, bs), 4.536 (2H, d, J 5.0 Hz), 5.069 (2H, q), 5.247 (1H, bd), 5.377 (1H, bd), 6.013 (1H, m), 6.586 (2H, s), 6.955 (2H, m) and 7.138 (1H, t, J 9.0 Hz).

Example 159

2-Fluoro-5-(2-propenyl)oxybenzyl piperazine-1-carboxylate fumarate was prepared from 2-fluoro-5-hydroxybenzyl alcohol, allyl bromide and 1-chlorocarbonyl-4-tert-butoxycarbonylpiperazine according to the procedures described for Example 148 to give the product as a white solid (8.5%); HPLC (XTERRA, 50–80%, 220 nm) 98% (1.29 min); NMR $\delta_H$ (400 MHz, DMSO-$d_6$) 2.774(4H, bs), 3.381(4H, bs), 4.545(2H, d), 5.072(2H, s), 5.251(1H, m), 5.378(1H, m), 6.018(1H, m), 6.557(2H, s), 6.964(2H, m) and 7.139(1H, t, J 9.0 Hz).

Example 160

2,6-Difluoro-4-(2-thienylmethyl)oxybenzyl piperazine-1-carboxylate fumarate was prepared from 2,6-difluoro-4-hydroxybenzyl alcohol, 2-thiophenemethanol and 1-chlorocarbonyl-4-tert-butoxycarbonylpiperazine according to the procedures described for Example 152 to give the product as a white solid (0.6%); HPLC (XTERRA, 50–80%, 220 nm) 90.6% (3.53 min); NMR $\delta_H$ (400 MHz, DMSO-$d_6$) 2.852 (4H, bs), 3.400(4H, bs), 5.058(2H, s), 5.354(2H, s), 6.589 (6H, s), 6.884(2H, d, J 10 Hz), 7.052(1H, m), 7.249(1H, bd) and 7.583(1H, dd, J 1.5, 5.0 Hz).

Example 161

(R)-2,6-Difluoro-4-(2-thienylmethyl)oxybenzyl 2-methylpiperazine-1-carboxylate fumarate was prepared from 2,6-difluoro-4-hydroxybenzyl alcohol, 2-thiophenemethanol and (R) 1-chlorocarbonyl-2-methyl-4-tert-butoxycarbonylpiperazine according to the procedures described for Example 152 to give the product as a white solid (0.24%); HPLC (XTERRA, 50/80%, 220 nm) 100% (4.36 min); NMR $\delta_H$ (400 MHz, DMSO-$d_6$) 1.128(3H, d. J 7.0 Hz), 2.931(1H, bm), 3.655(4H, bd), 4.073(2H, bs), 5.036(2H, q), 5.340(2H, s), 6.60(4H, s), 6.880(1H, d, J 7.0 Hz), 7.051(1H, m), 7.248(2H, m) and 7.581(1H, m).

Example 162 cis-2,6-Dimethyl-piperazine-1-carboxylic acid 2,6-difluoro-4-(thiophen-2-ylmethoxy)-benzyl ester fumarate was prepared from 2,6-difluoro-4-hydroxybenzyl alcohol, 2-thiophenemethanol and 1-chlorocarbonyl-cis-2,6-dimethyl-4-tert-butoxycarbonylpiperazine according to the procedures described for Example 152 to give the product as a white solid (1.8%); HPLC (XTERRA, 50/80%, 220 nm) 94% (5.05 min); NMR $\delta_H$ (400 MHz, DMSO-$d_6$) 1.160(6H, d, J 7.0 Hz), 2.733(4H, bm), 3.912(2H, bs), 5.042(2H, s), 5.348(2H, s), 6.611(3H, s), 6.884(2H, d, J 10 Hz), 7.050(1H, m), 7.242(1H, m) and 7.582(1H, dd, J 1.5, 5.0 Hz).

Example 163

5-Butylaminocarbonyloxy-2-fluorobenzyl cis-2,6-dimethylpiperazine-1-carboxylate hydrochloride 5-Butylaminocarbonyloxy-2-fluorobenzyl-4-tert-butoxycarbonyl-cis-2,6-dimethylpiperazine-1-carboxylate was prepared from 5-hydroxy-2-fluorobenzyl-4-tert-butoxycarbonyl-cis-2,6-dimethylpiperazine-1-carboxylate and butyl isocyanate according to the method described for Example 139 to give the product as a colourless gum (0.177 g, 92%); Rf (Silica, isopropyl ether) 0.175; $\delta_H$ (400 MHz, $CDCl_3$) 7.14 (1H, m), 7.07–7.01 (2H, m), 5.18 (2H, s), 5.01 (1H, br), 4.20 (2H, br), 3.95 (H, br), 3.26 (2H, m, J 7 Hz), 2.96 (2H, br), 1.56 (2H, m, J 7.2 Hz), 1.48 (9H, s), 1.39 (2H, m, J 8 Hz), 1.23 (6H, d, J 7.0 Hz), and 0.96 (3H, t, J 7.3 Hz).

5-Butylaminocarbonyloxy-2-fluorobenzyl cis-2,6-dimethylpiperazine-1-carboxylate hydrochloride was prepared from 5-butylaminocarbonyloxy-2-fluorobenzyl-4-tert-butoxycarbonyl-cis-2,6-dimethylpiperazine-1-carboxylate according to the procedure described in Example 52 to give the product as a white solid (0.1223 g, 85%); (Found: C, 54.6; H, 7.1; N, 9.9%. $C_{19}H_{28}FN_3O_4$.HCl requires C, 54.6; H, 7.0; N, 10.05%); NMR $\delta_H$ (400 MHz, DMSO-$d_6$) 9.7 (1H, br), 9.3 (1H, br), 7.76 (1H, t, J 5.6 Hz), 7.24 (1H, t, J 9.2 Hz), 7.20 (1H, m), 7.12 (1H, m, J 4.0 Hz), 5.15 (2H, s), 4.30 (2H, m), 3.15 (2H, d, J 13 Hz), 3.09–3.02 (4H, m), 1.45 (2H, m, J 7.2 Hz), 1.36–1.29 (8H, m, J 7.2 Hz), and 0.89 (3H, t, J 7.2 Hz).

Example 164

2-Fluoro-5-(2-propynyl)oxybenzyl cis-2,6-dimethylpiperazine-1-carboxylate hydrochloride 2-Fluoro-5-(2-propynyl)oxybenzyl-4-tert-butoxycarbonyl-cis-2,6-dimethylpiperazine-1-carboxylate was prepared from 5-hydroxy-2-fluorobenzyl-4-tert-butoxycarbonyl-cis-2,6-dimethylpiperazine-1-carboxylate and propargyl bromide to give the product as a colourless gum (0.191 g, >100%). Rf (Silica, isopropyl ether) 0.25; $\delta_H$ (400 MHz, $CDCl_3$) 7.00–6.98 (2H, m), 6.90 (1H, m), 5.18 (2H, s), 4.66 (2H, d, J 0.24 Hz), 4.21 (2H, m, J 5.6 Hz), 3.95 (2H, br), 2.97 (2H, br), 2.51 (1H, t, J 0.24 Hz), 1.48 (9H, s), and 1.24 (6H, d, J 6.8 Hz).

2-Fluoro-5-(2-propynyl)oxybenzyl cis-2,6-dimethylpiperazine-1-carboxylate hydrochloride as prepared from 2-fluoro-5-(2-propynyl)oxybenzyl-4-tert-butoxycarbonyl-cis-2,6-dimethylpiperazine-1-carboxylate according to the procedures described in Example 52 to give the product as a white solid (0.1352 g, 95% overall); $\nu_{max}$ (diffuse reflectance)/cm−1 3507, 3292, 3242, 2125, 1700, 1594, 1506, and 1209; $\delta_H$ (400 MHz, DMSO-$d_6$)10.0–9.0 (2H, br), 7.19 (1H, t, J 9.2 Hz), 7.06 (1H, m), 7.00 (1H, m), 5.13 (2H, s), 4.79 (2H, d, J 0.24 Hz), 4.31 (2H, m, J 6 Hz), 3.57 (1H, t, J 0.24 Hz), 3.15 (2H, d, J 13.2 Hz), 3.07 (2H, dd, J 5 and 13.2 Hz), and 1.31 (6H, d, J 7.2 Hz).

Example 165

5-(5-[2,1,3]Benzothiadiazolylmethyl)oxy-2-fluorobenzyl cis-2,6-dimethylpiperazine-1-carboxylate was prepared from 2-fluoro-5-hydroxybenzyl alcohol, 5-[2,1,3]benzothiadiazolylmethyl chloride and 1-chlorocarbonyl-cis-2,6-dimethyl-4-tert-butoxycarbonylpiperazine according to the procedures described for Examples 121 and 54 to give the product as a yellow oil: $\delta_H$ (400 MHz, DMSO-$d_6$) 1.25 (6H, d, J 7.0 Hz), 2.78–2.95 (4H, m), 4.10 (2H, br), 5.20 (2H, s), 5.22 (2H, s), 6.90–7.08 (3H, m), 7.65 (1H, m) and 8.03 (2H, m), NH not observed; HPLC (XTERRA, 50/80%, 220 nm) 90.7% (4.84 min).

Example 166

2-Fluoro-5-(3-fluorobenzyl)oxybenzyl cis-2,6-dimethylpiperazine-1-carboxylate was prepared from 2-fluoro-5-hydroxybenzyl alcohol, 3-fluorobenzyl bromide and 1-chlorocarbonyl-cis-2,6-dimethyl-4-tert-butoxycarbonylpiperazine according to the procedures described for Examples 121 and 54 to give the product as a yellow oil: $\delta_H$ (400 MHz, DMSO-$d_6$) 1.28 (6H, d, J 6.9 Hz), 2.77–2.90 (4H, m), 4.10 (2H, br), 5.03 (2H, s), 5.17 (2H, s), 6.85 (1H, m), 6.95–7.10 (3H, m), 7.15 (2H, m) and 7.35 (1H, m), NH not observed; HPLC (XTERRA, 50/80%, 220 nm) 85% (4.83 min).

Example 167

(R)-2-Fluoro-5-pentyloxybenzyl 2-methylpiperazine-1-carboxylate was prepared from 2-fluoro-5-hydroxybenzyl alcohol, 1-iodopentane and (R) 2-methylpiperazine resin according to the procedures described for Example 126 to give the product as a yellow oil: $\delta_H$ (400 MHz, DMSO-$d_6$) 0.89 (3H, t, J 7.0 Hz), 1.24 (3H, d, J 7.1 Hz), 1.30–1.45 (4H, m), 1.70 (2H, pent, J 6.7 Hz), 2.90 (1H, m), 3.0–3.20 (4H, m), 3.92 (3H, m), 4.38 (1H, m), 5.07 (1H, d, J 12.5 Hz), 5.12 (1H, d, J 12.5 Hz), 6.93 (1H, m), 6.98 (1H, m), 7.14 (1H, m), 8.90 (1H, br) and 9.40 (1H, br); HPLC (XTERRA, 50/80%, 220 nm) 84.6% (4.85 min).

Example 168

5-(Cyclopropylmethyl)oxy-2-fluorobenzyl cis-2,6-dimethylpiperazine-1-carboxylate fumarate was prepared from 2-fluoro-5-hydroxybenzyl alcohol, cyclopropylmethyl bromide and 1-chlorocarbonyl-cis-2,6-dimethyl-4-tert-butoxycarbonylpiperazine according to the procedures described for Examples 121 and 54 to give the product as a white solid: $\delta_H$ (400 MHz, DMSO-$d_6$) 7.13 (1H, t, J 9 Hz), 6.95 (1H, q, J 3 Hz), 6.90 (1H, dt, J 9, 3.5 Hz), 6.58 (2H, s), 5.08 (2H, s), 3.98 (2H, m), 3.78 (2H, d, J 7 Hz), 2.80 (2H, d, J 12 Hz), 2.72 (2H, dd, J 12, 4.5 Hz), 1.20 (6H, d, J 7 Hz), 0.56 (2H, ddd, J 8, 6, 4.5 Hz) and 0.30 (2H, dt, J 6, 4.5 Hz).

Example 169

(R)-2-Methyl-piperazine-1-carboxylic acid 2-fluoro-5-(2-thiophen-2-yl-ethoxy)-benzyl ester fumarate 2-Fluoro-5-[2-(2-thienyl)]ethoxybenzyl alcohol was prepared from 2-thiophene-ethanol (0.5 g) and 2-fluoro-5-hydroxybenzyl alcohol according to the procedure described in Example 152 to give the product as a clear oil (0.12 g); $\delta_H$ (400 MHz, $CDCl_3$) 7.16 (1H, dd, J 5, 1.5 Hz), 6.98–6.92 (3H, m), 6.91 (1H, m), 6.78 (1H, dt, J 9, 3.5 Hz), 4.70 (2H, d, J 6 Hz), 4.15 (2H, t, J 6.5 Hz) and 3.28 (2H, dt, J 6.5, 1 Hz); HPLC (XTERRA, 50/80%, 220 nm) 97% (3.49 min).

(R)-2-Methyl-piperazine-1-carboxylic acid 2-fluoro-5-(2-thiophen-2-yl-ethoxy)-benzyl ester fumarate was prepared from 2-fluoro-5-[2-(2-thienyl)]ethoxybenzyl alcohol and (R) 1-chlorocarbonyl-2-methyl 4-tert-butoxycarbonylpiperazine according to the procedures described in Example 152 to give the product as a white, crystalline solid (0.047 g); $\delta_H$ (400 MHz, DMSO-$d_6$) 7.53 (1H, dd, J 5, 1 Hz), 7.25–7.09 (3H, m), 7.02 (1H, m), 6.91 (1H, m), 6.58 (2H, s), 4.74 (2H, s), 4.56 (2H, s), 4.26 (1H, m), 3.82 (1H, m), 3.14 (1H, m), 3.00 (1H, m), 2.91–2.80 (2H, m), 2.67 (1H, m) and 1.28 (3H, d, J 6.5 Hz); HPLC (XTERRA, 50/80%, 220 nm) 99% (4.15 min).

Example 170 cis-2,6-Dimethyl-piperazine-1-carboxylic acid 3-bromo-2,6-difluoro-benzyl ester hydrochloride 1-Bromo-3-(bromomethyl)-2,4-difluoro-benzene Bromo-2,4-difluoro-3-methyl-benzene (22 g, 0.106 M) and N-bromosuccinimide (22.7 g, 0.128 M) were dissolved in tetrachloromethane (800 mL). Dibenzoylperoxide (0.52 g, 2 mM) was added and the mixture was irradiated for 1 h. Succinimide was removed by filtration of the cooled mixture and the filtrate was washed with water. The water phase was extracted with dichloromethane. Organic phases were pooled, dried with MgSO4 and and evaporated to yield a yellowish oil (32 g). The residue was purified by column chromatography (silica gel; n-hexane) to yield 28.4 g (94%) of the title compound as a colorless oil. MS (EI): 286.0 $(M)^+$.

(3-Bromo-2,6-difluoro-phenyl)-methanol

1-Bromo-3-(bromomethyl)-2,4-difluoro-benzene (45.2 g, 0.158 M) was dissolved in dioxane (800 mL), water (800 mL) and calcium carbonate (80 g, 0.80 M) were added and the mixture was refluxed for 16 h. The mixture was cooled, acidified with 2N HCl and extracted with dichloromethane. Organic phases were pooled, dried with Na2SO4 and and evaporated to yield a brownish oil (40.3 g). The residue was purified by column chromatography (silica gel; n-hexane/ethyl acetate 9:1) to yield 31.2 g (88%) of the title compound as a colorless solid. MS (EI): 224.0 $(M)^+$.

cis-2,6-Dimethyl-piperazine-1,4-dicarboxylic acid 4-tert-butyl ester 1-(3-bromo-2,6-difluoro-benzyl) ester The compound was prepared from (3-bromo-2,6-difluoro-phenyl)-methanol and 4-chlorocarbonyl-cis-3,5-dimethyl-piperazine-1-carboxylic acid tert-butyl ester according to the procedures described in Example 121 and 54 to give the product as a colorless oil (9.75 g); MS (ISP): 482.3 $(M+NH4)^+$.

cis-2,6-Dimethyl-piperazine-1-carboxylic acid 3-bromo-2,6-difluoro-benzyl ester hydrochloride The compound was prepared from cis-2,6-dimethyl-piperazine-1,4-dicarboxylic acid 4-tert-butyl ester 1-(3-bromo-2,6-difluoro-benzyl) ester according to the procedures described in Example 121 and 54 to give the product as a colorless solid (0.159 g); m.p.: 207–210° C.; MS (ISP): 365.1 $(M+H)^+$.

Example 171 cis-2,6-Dimethyl-piperazine-1-carboxylic acid 2,4-difluoro-2'-methoxy-biphenyl-3-ylmethyl ester A mixture of 46.33 mg (0.1 mmol) cis-2,6-dimethyl-piperazine-1,4-dicarboxylic acid 1-(3-bromo-2,6-difluoro-benzyl) ester 4-tert-butyl ester, 16.71 mg (0.11 mmol) 2-methoxyphenylboronic acid, 3.65 mg (0.005 mmol) dichloro(1,1'-bis(diphenylphosphino) ferrocene)palladium (II) dichloromethane adduct and 0.11 ml of a 2M $Na_2CO_3$ aq. solution in 1.2 ml dioxane was heated for 17 h to 85° C. The mixture was filtered and 0.15 ml 4N HCl in dioxane was added and the mixture heated for 3 h to 65° C. After cooling to ambient temperature 0.2 ml triethylamine and water were added to dissolve the mixture. The solution was subjected to reversed phase preparative HPLC eluting with a water/acetonitrile gradient to yield after evaporation of the solvents 28.2 mg (66%) of the title compound. MS (ISP): 391 $MH^+$ In analogy to Example 171 the following Examples 172–176 can be prepared from given starting material that is either commercially available or described in the literature:

Example 172 cis-2,6-Dimethyl-piperazine-1-carboxylic acid 2,4-difluoro-3',4'-dimethoxy-biphenyl-3-ylmethyl ester hydrochloride Following the general procedure of example 171 the title compound was synthesized from cis-2,6-dimethyl-piperazine-1,4-dicarboxylic acid 1-(3-bromo-2,6-difluoro-benzyl) ester 4-tert-butyl ester and 3,4-dimethoxyphenyl boronic acid. MS (ISP): 421 $MH^+$ Example 173 cis-2,6-Dimethyl-piperazine-1-carboxylic acid 2,4-difluoro-3'-hydroxy-4'-methoxy-biphenyl-3-ylmethyl ester hydrochloride Following the general procedure of example 171 the title compound was synthesized from cis-2,6-dimethyl-piperazine-1,4-dicarboxylic acid 1-(3-bromo-2,6-difluoro-benzyl) ester 4-tert-butyl ester and 2-methoxy-5-(4,4,5,5-tetramethyl-[1,3,2]dioxaborolan-2-yl)-phenol. MS (ISP): 407 $MH^+$ Example 174 cis-2,6-Dimethyl-piperazine-1-carboxylic acid 3'-amino-2,4-difluoro-biphenyl-3-ylmethyl ester hydrochloride Following the general procedure of example 171 the title compound was synthesized from cis-2,6-dimethyl-piperazine-1,4-dicarboxylic acid 1-(3-bromo-2,6-difluoro-benzyl) ester 4-tert-butyl ester and 3-aminophenyl boronic acid. MS (ISP): 376 $MH^+$ Example 175 cis-2,6-Dimethyl-piperazine-1-carboxylic acid 4'-acetyl-2,4-difluoro-biphenyl-3-ylmethyl ester hydrochloride Following the general procedure of example 171 the title compound was synthesized from cis-2,6-dimethyl-piperazine-1,4-dicarboxylic acid 1-(3-bromo-2,6-difluoro-benzyl) ester 4-tert-butyl ester and 4-acetyl-phenylboronic acid. MS (ISP): 403 $MH^+$ Example 176 cis-2,6-Dimethyl-piperazine-1-carboxylic acid 3'-acetyl-2,4-difluoro-biphenyl-3-ylmethyl ester hydrochloride Following the general procedure of example 171 the title compound was synthesized from cis-2,6-dimethyl-piperazine-1,4-dicarboxylic acid 1-(3-bromo-2,6-difluoro-benzyl) ester 4-tert-butyl ester and 3-acetyl-phenylboronic acid. MS (ISP): 403 $MH^+$ Example 177

(R)-2-Ethyl-piperazine-1-carboxylic acid 2,6-difluoro-3-methyl-benzyl ester (R)-2-Ethyl-piperazine dihydrochloride:

(3R)-3-Ethyl-1-(phenylmethyl)-piperazine (30.7 g, 0.15 M) was dissolved in ethanol (650 mL), palladium on carbon (10%; 11.5 g) was added and the mixture was hydrogenated (3 bar) at room temperature. The catalyst was removed by filtration and 5.5 N HCl in Ethanol (60 mL) was added to the filtrate. The product crystallized and was filtered off after evaporation of 400 mL of the solvent and subsequent addition of diethylether (400 mL). White solid (25.9 g; 92%); MS (EI): 114.2 $(M)^+$.

(R)-3-Ethyl-piperazine-1-carboxylic acid tert-butyl ester:

(R)-2-Ethyl-piperazine dihydrochloride (25.9 g, 01.38 M) was dissolved in dichloromethane (700 mL) and cooled to 0° C. Triethylamine (48.2 mL, 0.346 M) was added and subsequently di-tert-butyl-dicarbonate (30.2 g, 0.138 M) dissolved in dichloromethane (50 mL) was added within 30 min with cooling (0–5° C.) and stirring. Stirring was continued for another 3 h at room temperature. The mixture was washed with water, the water phase was extracted twice with dichloromethane, organic phases were pooled, dried with Na2SO4 and evaporated to yield a colorless oil (31 g). The residue was purified by column chromatography (silica gel; dichoromethane/methanol 90:10) to yield 26.5 g (89%) of a colorless oil. MS (ISP): 215.5 $(M+H)^+$.

(R)-4-Chlorocarbonyl-3-ethyl-piperazine-1-carboxylic acid tert-butyl ester:

Bis-(trichloromethyl)-carbonate (13.9 g, 47 mM) was dissolved in dichloromethane (500 mL) and cooled to 0° C. A mixture of (R)-3-ethyl-piperazine-1-carboxylic acid tert-butyl ester (26.5 g; 0.124 M) and pyridine (10.9 mL, 0.136 M) in dichloromethane (150 mL) was added dropwise with stirring (0–3° C.). Stirring was continued for another ½ h at room temperature. The mixture was washed with water and brine, the water phases were extracted with dichloromethane, organic phases were pooled, dried with Na2SO4 and evaporated to yield a brown oil (34 g, 99%) which crystallized upon standing; MS (EI): 276.2 $(M)^+$.

(R)-2-Ethyl-piperazine-1,4-dicarboxylic acid 4-tert-butyl ester 1-(3-bromo-2,6-difluoro-benzyl) ester:

The compound was prepared from (3-bromo-2,6-difluoro-phenyl)-methanol and (R)-4-chlorocarbonyl-3-ethyl-piperazine-1-carboxylic acid tert-butyl ester according to the procedures described in Example 121 and 54 to give the product as a colorless oil (9.22 g); MS (ISP): 480.3, 482.3 $(M+H)^+$.

(R)-2-Ethyl-piperazine-1,4-dicarboxylic acid 4-tert-butyl ester 1-(2,6-difluoro-3-methyl-benzyl) ester:

A mixture of (R)-2-ethyl-piperazine-1,4-dicarboxylic acid 4-tert-butyl ester 1-(3-bromo-2,6-difluoro-benzyl) ester (226 mg), tetrakis(triphenylphosphine)palladium (56 mg), trimethylboroxine (122 mg) and potassium carbonate (200 mg) in dioxane (5 mL) was heated to reflux with stirring for 6 h. The cooled was mixture was partitioned between water and ethylacetate. The water phase was extracted once with ethylacetate, organic phases were pooled and dried with Na2SO4 to yield after evaporation a dark oil (259 mg). This residue was purified by column chromatography (silica gel; n-hexane/ethylacetate gradient) to yield 160 mg (82%) of a yellow oil. MS (ISP): 416.4 $(M+H)^+$.

(R)-2-Ethyl-piperazine-1-carboxylic acid 2,6-difluoro-3-methyl-benzyl ester:

(R)-2-Ethyl-piperazine-1,4-dicarboxylic acid 4-tert-butyl ester 1-(2,6-difluoro-3-methyl-benzyl) ester (160 mg) was dissolved in methanol (3 mL), 500 μL 4 N HCl in dioxane was added and the mixture was stirred for 18 h at room temperature. The mixture was added to water (10 mL) made alkaline with 1 N NaOH and extracted with ethylacetate. Organic phases were pooled, dried with Na2SO4 and evaporated to give the product as a yellowish oil (120 mg); MS (ISP): 299.4 $(M+H)^+$.

Example 178

(R)-2-Ethyl-piperazine-1-carboxylic acid 2,6-difluoro-benzyl ester

This compound was prepared from (R)-4-chlorocarbonyl-3-ethyl-piperazine-1-carboxylic acid tert-butyl ester and 2,6-difluorobenzylalcohol via (R)-2-ethyl-piperazine-1,4-dicarboxylic acid 4-tert-butyl ester 1-(2,6-difluoro-benzyl) ester according to the procedures described in Example 177 to give the product as a yellowish oil (69 mg); MS (ISP): 285.2 $(M+H)^+$.

Example 179

(R)-2-Ethyl-piperazine-1-carboxylic acid 4-cyclopropylmethoxy-2,6-difluoro-benzyl ester 3,5-Difluoro-4-hydroxymethyl-phenol 3,5-Difluorophenol (67.2 g, 0.48 M) was added to a solution of potassium hydroxide (35.1 g, 0.53 M) in water (145 mL). The mixture was heated to 60° C. and a mixture of formaldehyde (74 mL, 36% in water) and water (145 mL) was added dropwise. The mixture was stirred for 20 h at 40° C. After cooling to 0–5° C. concentrated HCl (60 mL, 36%) was added. The product precipitated, was filtered off and dried. Colorless solid (35.9 g, 41%); m.p.: 156–160° C. dec.; MS (ISN): 159.2 $(M-H)^-$.

4-Cyclopropylmethoxy-2,6-difluoro-benzylalcohol:

Sodium hydride (82 mg, 55%, 1.87 mM) was added to a solution of 3,5-difluoro-4-hydroxymethyl-phenol (300 mg, 1.87 mM) in dimethylformamide (4 mL). After 1 h stirring at room temperature cyclopropylmethylbromide (135 mg, 1.87 mM) was added and stirring continued for 24 h. The mixture was partitioned between water and diethylether. Organic phases were pooled, washed with brine and dried with MgSO4 to yield after evaporation a yellow oil (673 mg). This residue was purified by column chromatography (silica gel; n-hexane/ethylacetate gradient) to yield 287 mg (71%) of the product as a yellowish oil. MS (EI): 214.1 $(M)^+$.

(R)-2-Ethyl-piperazine-1,4-dicarboxylic acid 4-tert-butyl ester 1-(4-cyclopropylmethoxy-2,6-difluoro-benzyl) ester A mixture of 4-cyclopropylmethoxy-2,6-difluoro-benzylalcohol (270 mg, 1.26 mM) and (R)-4-chlorocarbonyl-3-ethyl-piperazine-1-carboxylic acid tert-butyl ester (349 mg, 1.26 mM) in dimethylformamide (2 mL) was added slowly to a suspension of sodium hydride (83 mg, 55%, 1.89 mM) in dimethylformamide (2 mL). The mixture was stirred at room temperature for 5 h and partitioned between water and diethylether. Organic phases were pooled, washed with brine and dried with MgSO4 to yield after evaporation a yellow oil (585 mg). This residue was purified by column chromatography (silica gel; n-hexane/ethylacetate gradient) to yield 406 mg (71%) of the product as a yellowish oil. MS (ISP): 477.3 $(M+H)^+$.

(R)-2-Ethyl-piperazine-1-carboxylic acid 4-cyclopropylmethoxy-2,6-difluoro-benzyl ester (R)-2-Ethyl-piperazine-1,4-dicarboxylic acid 4-tert-butyl ester 1-(4-cyclopropylmethoxy-2,6-difluoro-benzyl) ester (400 mg) was dissolved in methanol (5 mL), 1100 μL 4 N HCl in dioxane was added and the mixture was stirred for 18 h at room temperature. The mixture was made alkaline with 2 N NaOH and eluted with ethylacetate over a column containing 10 g ChemElut CE1010. The filtrate was collected, solvent was evaporated to give a yellowish oil (237 mg). This residue was purified by column chromatography (silica gel; dichloromethane/methanol gradient) to yield 186 mg (59%) of the product as a colorless oil. MS (ISP): 355.4 $(M+H)^+$.

Example 180

(R)-2-Ethyl-piperazine-1-carboxylic acid 2,6-difluoro-4-propoxy-benzyl ester 2,6-Difluoro-4-propoxy-benzylalcohol:

This compound was prepared from 3,5-difluoro-4-hydroxymethyl-phenol and propylbromide according to the procedure described in Example 179 to give the product as a yellowish oil (168 mg, 44%); MS (EI): 202.1 $(M)^+$.

(R)-2-Ethyl-piperazine-1,4-dicarboxylic acid 4-tert-butyl ester 1-(2,6-difluoro-4-propoxy-benzyl) ester This compound was prepared from 2,6-difluoro-4-propoxy-benzylalcohol and (R)-4-chlorocarbonyl-3-ethyl-piperazine-1-carboxylic acid tert-butyl ester according to the procedure described in Example 179 to give the product as a colorless oil (257 mg; 78%); MS (ISP): 465.4 $(M+Na)^+$.

(R)-2-Ethyl-piperazine-1-carboxylic acid 2,6-difluoro-4-propoxy-benzyl ester

This compound was prepared from (R)-2-ethyl-piperazine-1,4-dicarboxylic acid 4-tert-butyl ester 1-(2,6-difluoro-4-propoxy-benzyl) ester according to the procedure described in Example 179 to give the product as a colorless oil (133 mg; 69%); MS (ISP): 343.4 $(M+H)^+$.

Example 181

(R)-2-Ethyl-piperazine-1-carboxylic acid 4-allyloxy-2,6-difluoro-benzyl ester 4-Allyloxy-2,6-difluoro-benzylalcohol:

This compound was prepared from 3,5-difluoro-4-hydroxymethyl-phenol and allylbromide according to the procedure described in Example 179 to give the product as a yellowish oil (229 mg, 61%); MS (EI): 200.1 $(M)^+$.

(R)-2-Ethyl-piperazine-1,4-dicarboxylic acid 4-tert-butyl ester 1-(4-allyloxy-2,6-difluoro-benzyl) este This compound was prepared from 4-allyloxy-2,6-difluoro-benzylalcohol and (R)-4-chlorocarbonyl-3-ethyl-piperazine-1-carboxylic acid tert-butyl ester according to the procedure described in Example 179 to give the product as a colorless oil (230 mg; 47%); MS (ISP): 441.4 $(M+H)^+$.

(R)-2-Ethyl-piperazine-1-carboxylic acid 4-allyloxy-2,6-difluoro-benzyl ester

This compound was prepared from (R)-2-ethyl-piperazine-1,4-dicarboxylic acid 4-tert-butyl ester 1-(4-allyloxy-2,6-difluoro-benzyl) ester according to the procedure described in Example 179 to give the product as a colorless oil (101 mg; 59%); MS (ISP): 341.4 $(M+H)^+$.

Example 182

(R)-2-Ethyl-piperazine-1-carboxylic acid 2,6-difluoro-4-prop-2-ynyloxy-benzyl ester 2,6-Difluoro-4-prop-2-ynyloxy-benzylalcohol:

This compound was prepared from 3,5-difluoro-4-hydroxymethyl-phenol and propargylbromide according to the procedure described in Example 179 to give the product as a yellowish oil (229 mg, 62%); MS (EI): 197.1 $(M)^+$.

(R)-2-Ethyl-piperazine-1,4-dicarboxylic acid 4-tert-butyl ester 1-(2,6-difluoro-4-prop-2-ynyloxy-benzyl) ester This compound was prepared from 2,6-difluoro-4-prop-2-ynyloxy-benzylalcohol and (R)-4-chlorocarbonyl-3-ethyl-piperazine-1-carboxylic acid tert-butyl ester according to the procedure described in Example 179 to give the product as a colorless oil (336 mg; 67%); MS (ISP): 456.5 $(M+NH4)^+$.

(R)-2-Ethyl-piperazine-1-carboxylic acid 2,6-difluoro-4-prop-2-ynyloxy-benzyl ester This compound was prepared from (R)-2-ethyl-piperazine-1,4-dicarboxylic acid 4-tert-butyl ester 1-(2,6-difluoro-4-prop-2-ynyloxy-benzyl) ester according to the procedure described in Example 179 to give the product as a colorless oil (195 mg; 76%); MS (ISP): 339.3$(M+H)^+$.

Example 183

(R)-2-Ethyl-piperazine-1-carboxylic acid 4-butoxy-2,6-difluoro-benzyl ester 4-Butoxy-2,6-difluoro-benzylalcohol:

This compound was prepared from 3,5-difluoro-4-hydroxymethyl-phenol and butylbromide according to the procedure described in Example 179 to give the product as a yellowish oil (279 mg, 69%); MS (EI): 216.1 $(M)^+$.

(R)-2-Ethyl-piperazine-1,4-dicarboxylic acid 4-tert-butyl ester 1-(4-butoxy-2,6-difluoro-benzyl) ester This compound was prepared from 4-butoxy-2,6-difluoro-benzylalcohol and (R)-4-chlorocarbonyl-3-ethyl-piperazine-1-carboxylic acid tert-butyl ester according to the procedure described in Example 179 to give the product as a colorless oil (454 mg; 80%); MS (ISP): 479.4 $(M+Na)^+$.

(R)-2-Ethyl-piperazine-1-carboxylic acid 4-butoxy-2,6-difluoro-benzyl ester

This compound was prepared from (R)-2-ethyl-piperazine-1,4-dicarboxylic acid 4-tert-butyl ester 1-(4-butoxy-2,6-difluoro-benzyl) ester according to the procedure described in Example 179 to give the product as a colorless oil (240 mg; 68%); MS (ISP): 357.4 $(M+H)^+$.

Example 184

(R)-2-Ethyl-piperazine-1-carboxylic acid 2,6-difluoro-4-(2-methoxy-ethoxy)-benzyl ester 2,6-Difluoro-4-(2-methoxy-ethoxy)-benzylalcohol:

This compound was prepared from 3,5-difluoro-4-hydroxymethyl-phenol and methoxyethyl bromide according to the procedure described in Example 179 to give the product as a colorless oil (159 mg, 39%); MS (EI): 218.1 $(M)^+$.

(R)-2-Ethyl-piperazine-1,4-dicarboxylic acid 4-tert-butyl ester 1-(2,6-difluoro-4-(2-methoxy-ethoxy)-benzyl) ester:

This compound was prepared from 2,6-difluoro-(2-methoxy-ethoxy)-benzylalcohol and (R)-4-chlorocarbonyl-3-ethyl-piperazine-1-carboxylic acid tert-butyl ester according to the procedure described in Example 179 to give the product as a colorless oil (172 mg; 55%); MS (ISP): 481.4 $(M+Na)^+$.

(R)-2-Ethyl-piperazine-1-carboxylic acid 2,6-difluoro-4-(2-methoxy-ethoxy)-benzyl ester:

This compound was prepared from (R)-2-ethyl-piperazine-1,4-dicarboxylic acid 4-tert-butyl ester 1-(2,6-difluoro-4-(2-methoxy-ethoxy)-benzyl) ester according to the procedure described in Example 179 to give the product as a colorless oil (75 mg; 56%); MS (ISP): 359.3$(M+H)^+$.

Example 185

(R)-2-Ethyl-piperazine-1-carboxylic acid 4-ethoxy-2,6-difluoro-benzyl ester 4-Ethoxy-2,6-difluoro-benzylalcohol:

This compound was prepared from 3,5-difluoro-4-hydroxymethyl-phenol and ethylbromide according to the procedure described in Example 179 to give the product as a yellowish oil (241 mg, 68%); MS (EI): 188.1 $(M)^+$.

(R)-2-Ethyl-piperazine-1,4-dicarboxylic acid 4-tert-butyl ester 1-(4-ethoxy-2,6-difluoro-benzyl) ester:

This compound was prepared from 4-ethoxy-2,6-difluoro-benzylalcohol and (R)-4-chlorocarbonyl-3-ethyl-piperazine-1-carboxylic acid tert-butyl ester according to the procedure described in Example 179 to give the product as a colorless oil (478 mg; 81%); MS (ISP): 429.6 $(M+H)^+$.

(R)-2-Ethyl-piperazine-1-carboxylic acid 4-ethoxy-2,6-difluoro-benzyl ester

This compound was prepared from (R)-2-ethyl-piperazine-1,4-dicarboxylic acid 4-tert-butyl ester 1-(4-ethoxy-2,6-difluoro-benzyl) ester according to the procedure described in Example 179 to give the product as a colorless oil (167 mg; 46%); MS (ISP): 329.3 $(M+H)^+$.

Example 186

(R)-2-Ethyl-piperazine-1-carboxylic acid 2,6-difluoro-4-(2-methyl-thiazol-4-ylmethoxy)-benzyl ester 2,6-Difluoro-4-(2-methyl-thiazol-4-ylmethoxy)-benzylalcohol:

This compound was prepared from 3,5-difluoro-4-hydroxymethyl-phenol and 4-chlormethyl-2-methylthiazol according to the procedure described in Example 179 to give the product as a colorless oil (369 mg, 73%); MS (ISP): 272.3 $(M+H)^+$.

(R)-2-Ethyl-piperazine-1,4-dicarboxylic acid 4-tert-butyl ester 1-(2,6-difluoro-4-(2-methyl-thiazol-4-ylmethoxy)-benzyl) ester:

This compound was prepared from 2,6-difluoro-(2-methyl-thiazol-4-ylmethoxy)-benzylalcohol and (R)-4-chlorocarbonyl-3-ethyl-piperazine-1-carboxylic acid tert-butyl ester according to the procedure described in Example 179 to give the product as a colorless oil (447 mg; 66%); MS (ISP): 534.3 $(M+Na)^+$.

(R)-2-Ethyl-piperazine-1-carboxylic acid 2,6-difluoro-4-(2-methyl-thiazol-4-ylmethoxy)-benzyl ester:

This compound was prepared from (R)-2-ethyl-piperazine-1,4-dicarboxylic acid 4-tert-butyl ester 1-(2,6-difluoro-4-(2-methyl-thiazol-4-ylmethoxy)-benzyl) ester according to the procedure described in Example 179 to give the product as a colorless oil (204 mg; 57%); MS (ISP): 412.4 $(M+H)^+$.

Example 187

(R)-2-Ethyl-piperazine-1-carboxylic acid 2-fluoro-5-methoxy-benzyl ester hydrochloride Fluoro-5-iodo-benzylalcohol 2-Fluoro-5-iodo-benzaldehyde (23.4 g, 0.093 M) was dissolved in methanol (150 mL). Sodium borohydride (1.8 g, 0.047 M) was added in portions with cooling (5° C.) and stirring. The mixture was stirred for 1 h at room temperature, poured into ice-water (600 mL) and extracted into ethylacetate. Organic phases were pooled, washed with brine and dried with MgSO4. The solvent was evaporated to yield a yellowish oil (24.2 g). This residue was purified by column chromatography (silica gel; n-hexane/ethylacetate 4:1) to yield 23.9 g (quant.) of the product as a colorless oil. MS (EI): 252.0 $(M)^+$.

(R)-2-Ethyl-piperazine-1,4-dicarboxylic acid 4-tert-butyl ester 1-(2-fluoro-5-iodo-benzyl) ester A mixture of 2-fluoro-5-iodo-benzylalcohol (5.0 g, 19.8 mM) and (R)-4-chlorocarbonyl-3-ethyl-piperazine-1-carboxylic acid tert-butyl ester (5.5 g, 19.8 mM) in dimethylformamide (70 mL) was added slowly to a suspension of sodium hydride (1.3 g, 55%, 1.89 mM) in dimethylformamide (30 mL). The mixture was stirred at room temperature for 5 h and partitioned between water and diethylether. Organic phases were pooled, washed with brine and dried with Na2SO4 to yield after evaporation a yellow oil (11.2 g). This residue was purified by column chromatography (silica gel; n-hexane/ethylacetate 3:1) to yield 9.4 g (97%) of the product as a yellowish oil. MS (ISP): 510.3 $(M+NH4)^+$.

(R)-2-Ethyl-piperazine-1,4-dicarboxylic acid 4-tert-butyl ester 1-(2-fluoro-5-hydroxy-benzyl) ester (R)-2-Ethyl-piperazine-1,4-dicarboxylic acid 4-tert-butyl ester 1-(2-fluoro-5-iodo-benzyl) ester (8.9 g, 18 mM) was dissolved in tetrahydrofuran (150 mL), trisopropylborate (6.7 g, 36 mM) was added and the mixture was cooled to −78° C. At this low temperature n-butyllithium (16.9 mL, 1.6N) was added drop by drop with stirring. The mixture was stirred for 45 min at −78° C., for another 45 min at −50° C. and for 15 min at 0° C. Acetic acid (9.5 mL, 50%) was added slowly with stirring (0–5° C.), followed by hydrogen peroxide (2.75 mL, 35%). Stirring continued with cooling for another 45 min and for 1 h at room temperature. The mixture was partitioned between water and diethylether, organic phases were pooled, washed with water, sodium thiosulfate solution (5%), brine and dried with Na2SO4 to yield after evaporation a light yellow oil (8.5 g). This residue was purified by column chromatography (silica gel; n-hexane/ethylacetate 1:1) to yield 3.0 g (43%) of the product as a yellowish oil. MS (ISP): 400.5 $(M+NH4)^+$.

(R)-2-Ethyl-piperazine-1-carboxylic acid 2-fluoro-5-methoxy-benzyl ester hydrochloride:

A mixture of 6.27 mg (0.157 mmol) NaH (60% suspension in mineral oil) and 40 mg (0.105 mmol) (R)-2-Ethyl-piperazine-1,4-dicarboxylic acid 4-tert-butyl ester 1-(2-fluoro-5-hydroxy-benzyl) ester in 1 ml DMF was stirred for 30 min at room temperature under argon. 16.4 mg (0.115 mmol) methyliodide was added and the mixture was stirred 30 min at room temperature. After addition of 60 ul HCl (37%) the mixture was purified with preparative HPLC eluting with an acetonitrile/water gradient. The fractions containing the desired intermediate were combined and 0.05 ml HCl (37%) was added before evaporation to dryness. The residue was taken up in 1 ml dioxane and 0.15 ml HCl (37%)

and stirred for 30 min at 60° C. Evaporation of the mixture yielded 20 mg (57%) of the title compound. MS (ISP): 297 $(M+H)^+$.

Example 188

(R)-2-Ethyl-piperazine-1-carboxylic acid 5-ethoxy-2-fluoro-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and ethyl bromide. MS (ISP): 311 $(M+H)^+$.

Example 189

(R)-2-Ethyl-piperazine-1-carboxylic acid 2-fluoro-5-propoxy-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and propyl bromide. MS (ISP): 325 $(M+H)^+$.

Example 190

(R)-2-Ethyl-piperazine-1-carboxylic acid 5-butoxy-2-fluoro-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and butyl bromide. MS (ISP): 339 $(M+H)^+$.

Example 191

(R)-2-Ethyl-piperazine-1-carboxylic acid 2-fluoro-5-pentyloxy-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and pentyl bromide. MS (ISP): 353 $(M+H)^+$.

Example 192

(R)-2-Ethyl-piperazine-1-carboxylic acid 2-fluoro-5-(3-methyl-butoxy)-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and 3-methyl-butyl bromide. MS (ISP): 353 $(M+H)^+$.

Example 193

(R)-2-Ethyl-piperazine-1-carboxylic acid 5-benzyloxy-2-fluoro-benzyl ester

According to example 187 the title compound was synthesized from (R)-2-ethyl-piperazine-1,4-dicarboxylic acid 4-tert-butyl ester 1-(2-fluoro-5-hydroxy-benzyl) ester and benzyl bromide. MS (ISP): 373 $(M+H)^+$.

Example 194

(R)-2-Ethyl-piperazine-1-carboxylic acid 2-fluoro-5-phenethyloxy-benzyl ester

According to example 187 the title compound was synthesized from (R)-2-ethyl-piperazine-1,4-dicarboxylic acid 4-tert-butyl ester 1-(2-fluoro-5-hydroxy-benzyl) ester and phenethyl bromide. MS (ISP): 387 $(M+H)^+$.

Example 195

(R)-2-Ethyl-piperazine-1-carboxylic acid 2-fluoro-5-(2-methyl-benzyloxy)-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and 2-methylbenzyl bromide. MS (ISP): 387 $(M+H)^+$.

Example 196

(R)-2-Ethyl-piperazine-1-carboxylic acid 2-fluoro-5-(3-methyl-benzyloxy)-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and 3-methylbenzyl bromide. MS (ISP): 387 $(M+H)^+$.

Example 197

(R)-2-Ethyl-piperazine-1-carboxylic acid 2-fluoro-5-(2-pyrrol-1-yl-ethoxy)-benzyl ester According to example 187 the title compound was synthesized from (R)-2-Ethyl-piperazine-1,4-dicarboxylic acid 4-tert-butyl ester 1-(2-fluoro-5-hydroxy-benzyl) ester and 2-pyrrol-1-yl-ethyl bromide. MS (ISP): 375 $(M+H)^+$.

Example 198

(R)-2-Ethyl-piperazine-1-carboxylic acid 5-cyclopropylmethoxy-2-fluoro-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and cyclopropylmethyl bromide. MS (ISP): 337 $(M+H)^+$.

Example 199

(R)-2-Ethyl-piperazine-1-carboxylic acid 5-cyclobutylmethoxy-2-fluoro-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and cyclobutylmethyl bromide. MS (ISP): 351 $(M+H)^+$.

Example 200

(R)-2-Ethyl-piperazine-1-carboxylic acid 5-cyclohexylmethoxy-2-fluoro-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and cyclohexylmethyl bromide. MS (ISP): 379 $(M+H)^+$.

Example 201

(R)-2-Ethyl-piperazine-1-carboxylic acid 5-(2-cyclohexyl-ethoxy)-2-fluoro-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and 2-cyclohexyl-ethyl bromide. MS (ISP): 393 $(M+H)^+$.

Example 202

(R)-2-Ethyl-piperazine-1-carboxylic acid 2-fluoro-5-prop-2-ynyloxy-benzyl ester

According to example 187 the title compound was synthesized from (R)-2-Ethyl-piperazine-1,4-dicarboxylic acid 4-tert-butyl ester 1-(2-fluoro-5-hydroxy-benzyl) ester and prop-2-ynyl bromide. MS (ISP): 337 $(M+H)^+$.

Example 203

(R)-2-Ethyl-piperazine-1-carboxylic acid 5-allyloxy-2-fluoro-benzyl ester

According to example 187 the title compound was synthesized from (R)-2-Ethyl-piperazine-1,4-dicarboxylic acid 4-tert-butyl ester 1-(2-fluoro-5-hydroxy-benzyl) ester and allyl bromide. MS (ISP): 323 $(M+H)^+$.

Example 204

(R)-2-Ethyl-piperazine-1-carboxylic acid 2-fluoro-5-(2-methoxy-ethoxy)-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and 2-methoxy-ethyl bromide. MS (ISP): 341 $(M+H)^+$.

Example 205

(R)-2-Ethyl-piperazine-1-carboxylic acid 5-(2-ethoxy-ethoxy)-2-fluoro-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and 2-ethoxy-ethyl bromide. MS (ISP): 355 $(M+H)^+$.

Example 206

(R)-2-Ethyl-piperazine-1-carboxylic acid 2-fluoro-5-(3-phenoxy-propoxy)-benzyl ester hydrochloride According to example 187 the title compound was synthesized from (R)-2-Ethyl-piperazine-1,4-dicarboxylic acid 4-tert-butyl ester 1-(2-fluoro-5-hydroxy-benzyl) ester and 3-phenoxy-propyl bromide. MS (ISP): 417 $(M+H)^+$.

Example 207

(R)-2-Ethyl-piperazine-1-carboxylic acid 2,6-difluoro-3-methoxy-benzyl ester hydrochloride (R)-2-Ethyl-piperazine-1,4-dicarboxylic acid 4-tert-butyl ester 1-(2,6-difluoro-3-hydroxy-benzyl) ester:

(R)-2-Ethyl-piperazine-1,4-dicarboxylic acid 4-tert-butyl ester 1-(3-bromo-2,6-difluoro-benzyl) ester (3.9 g, 8 mM) was dissolved in tetrahydrofuran (120 mL), trisopropylborate (3.1 g, 17 mM) was added and the mixture was cooled to −78° C. At this low temperature n-butyllithium (7.8 mL, 1.6N) was added drop by drop with stirring. The mixture was stirred for 45 min at −78° C., for another 45 min at −50° C. and for 15 min at 0° C. Acetic acid (4.4 mL, 50%) was added slowly with stirring (0–5° C.), followed by hydrogen peroxide (1.3 mL, 35%). Stirring continued with cooling for another 45 min and for 1 h at room temperature. The mixture was partitioned between water and diethylether, organic phases were pooled, washed with water, sodium thiosulfate solution (5%), brine and dried with Na2SO4 to yield after evaporation a light yellow oil (4.1 g). This residue was purified by column chromatography (silica gel; n-hexane/ethylacetate 1:1) to yield 0.93 g (28%) of the product as a colorless oil. MS (ISP): 418.2 $(M+NH4)^+$.

(R)-2-Ethyl-piperazine-1-carboxylic acid 2,6-difluoro-3-methoxy-benzyl ester hydrochloride:

A mixture of 5.03 mg (0.126 mmol) NaH (60% suspension in mineral oil) and 33.6 mg (0.084 mmol) (R)-2-Ethyl-piperazine-1,4-dicarboxylic acid 4-tert-butyl ester 1-(2,6-difluoro-3-hydroxy-benzyl) ester in 1 ml DMF was stirred for 30 min at room temperature under argon. 13.1 mg (0.092 mmol) methyliodide was added and the mixture was stirred 30 min at room temperature. After addition of 0.06 ml HCl (37%) the mixture was purified with preparative HPLC eluting with an acetonitrile/water gradient. The fractions containing the desired intermediate were combined and evaporated to dryness. The residue was taken up in 1 ml dioxane and 0.125 ml HCl (37%) and stirred for 30 min at 60° C. Evaporation of the mixture yielded 22 mg (75%) of the title compound. MS (ISP): 315 $(M+H)^+$.

Example 208

(R)-2-Ethyl-piperazine-1-carboxylic acid 3-ethoxy-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and ethyl bromide. MS (ISP): 329 $(M+H)^+$.

Example 209

(R)-2-Ethyl-piperazine-1-carboxylic acid 2,6-difluoro-3-propoxy-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and propyl bromide. MS (ISP): 343 $(M+H)^+$.

Example 210

(R)-2-Ethyl-piperazine-1-carboxylic acid 3-butoxy-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and butyl bromide. MS (ISP): 357 $(M+H)^+$.

Example 211

(R)-2-Ethyl-piperazine-1-carboxylic acid 2,6-difluoro-3-pentyloxy-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and pentyl bromide. MS (ISP): 371 $(M+H)^+$.

Example 212

(R)-2-Ethyl-piperazine-1-carboxylic acid 2,6-difluoro-3-(3-methyl-butoxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 3-methyl-butyl bromide. MS (ISP): 371 $(M+H)^+$.

Example 213

(R)-2-Ethyl-piperazine-1-carboxylic acid 3-benzyloxy-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and benzyl bromide. MS (ISP): 391 $(M+H)^+$.

Example 214

(R)-2-Ethyl-piperazine-1-carboxylic acid 2,6-difluoro-3-(3-phenyl-propoxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 3-phenyl-propyl bromide. MS (ISP): 419 $(M+H)^+$.

Example 215

(R)-2-Ethyl-piperazine-1-carboxylic acid 2,6-difluoro-3-(4-methyl-benzyloxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 4-methyl-benzyl bromide. MS (ISP): 405 $(M+H)^+$.

Example 216

(R)-2-Ethyl-piperazine-1-carboxylic acid 2,6-difluoro-3-(3-methyl-benzyloxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 3-methyl-benzyl bromide. MS (ISP): 405 $(M+H)^+$.

Example 217

(R)-2-Ethyl-piperazine-1-carboxylic acid 2,6-difluoro-3-(2-methyl-benzyloxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 2-methyl-benzyl bromide. MS (ISP): 205 $(M+H)^+$.

Example 218

(R)-2-Ethyl-piperazine-1-carboxylic acid 3-(3,3-dimethyl-butoxy)-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 3,3-dimethylbutyl bromide. MS (ISP): 385 $(M+H)^+$.

Example 219

(R)-2-Ethyl-piperazine-1-carboxylic acid 2,6-difluoro-3-(2-pyrrol-1-yl-ethoxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 2-pyrrol-1-yl-ethyl bromide. MS (ISP): 394 $(M+H)^+$.

Example 220

(R)-2-Ethyl-piperazine-1-carboxylic acid 3-cyclopropylmethoxy-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 3-cyclopropylmethyl bromide. MS (ISP): 355 $(M+H)^+$.

Example 221

(R)-2-Ethyl-piperazine-1-carboxylic acid 3-cyclobutylmethoxy-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 3-cyclobutylmethyl bromide. MS (ISP): 369 $(M+H)^+$.

Example 222

(R)-2-Ethyl-piperazine-1-carboxylic acid 3-(2-cyclohexyl-ethoxy)-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 2-cyclohexyl-ethyl bromide. MS (ISP): 411 $(M+H)^+$.

Example 223

(R)-2-Ethyl-piperazine-1-carboxylic acid 2,6-difluoro-3-prop-2-ynyloxy-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and prop-2-ynyl bromide. MS (ISP): 339 $(M+H)^+$.

Example 224

(R)-2-Ethyl-piperazine-1-carboxylic acid 3-allyloxy-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and allyl bromide. MS (ISP): 341 $(M+H)^+$.

Example 225

(R)-2-Ethyl-piperazine-1-carboxylic acid 2,6-difluoro-3-(2-methoxy-ethoxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 2-methoxy-ethyl bromide. MS (ISP): 359 $(M+H)^+$.

Example 226

(R)-2-Ethyl-piperazine-1-carboxylic acid 3-(2-ethoxy-ethoxy)-2,6-difluoro-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 2-ethoxy-ethyl bromide. MS (ISP): 373 $(M+H)^+$.

Example 227

(R)-2-Ethyl-piperazine-1-carboxylic acid 2,6-difluoro-3-(3-phenoxy-propoxy)-benzyl ester hydrochloride According to example 207 the title compound was synthesized from (R)-2-Ethyl-piperazine-1,4-dicarboxylic acid 4-tert-butyl ester 1-(2,6-difluoro-3-hydroxy-benzyl) ester and 3-phenoxy-propyl bromide. MS (ISP): 435 $(M+H)^+$.

Example 228

(R)-2-Ethyl-piperazine-1-carboxylic 1-[2-fluoro-5-(3-methoxy-propoxy)-benzyl] ester (R)-2-Ethyl-piperazine-1,4-dicarboxylic acid 4-tert-butyl ester 1-[2-fluoro-5-(3-methoxy-propoxy)-benzyl]ester:

This compound was prepared from (R)-2-ethyl-piperazine-1,4-dicarboxylic acid 4-tert-butyl ester 1-(2-fluoro-5-hydroxy-benzyl) ester and toluene-4-sulfonic acid 3-methoxy-propyl ester according to the procedure described in Example 187 to give the product as a colorless oil (342 mg; 94%); MS (ISP): 472.4 $(M+NH4)^+$.

(R)-2-Ethyl-piperazine-1-carboxylic 1-[2-fluoro-5-(3-methoxy-propoxy)-benzyl] ester:

This compound was prepared from (R)-2-ethyl-piperazine-1,4-dicarboxylic acid 4-tert-butyl ester 1-[2-fluoro-5-(3-methoxy-propoxy)-benzyl] ester according to the procedure described in Example 187 to give the product as a colorless oil (154 mg; 64%); MS (ISP): 355.4 $(M+H)^+$.

Example 229

(R)-2-Ethyl-piperazine-1-carboxylic acid 1-[2,6-difluoro-3-(3-methoxy-propoxy)-benzyl]ester (R)-2-Ethyl-piperazine-1,4-dicarboxylic acid 4-tert-butyl ester 1-[2,6-difluoro-3-(3-methoxy-propoxy)-benzyl]ester:

This compound was prepared from (R)-2-ethyl-piperazine-1,4-dicarboxylic acid 4-tert-butyl ester 1-(2,6-difluoro-3-hydroxy-benzyl) ester and toluene-4-sulfonic acid 3-methoxy-propyl ester according to the procedure described in Example 207 to give the product as a colorless oil (117 mg; 97%); MS (ISP): 490.4 $(M+NH4)^+$.

(R)-2-Ethyl-piperazine-1-carboxylic acid 1-[2,6-difluoro-3-(3-methoxy-propoxy)-benzyl]ester:

This compound was prepared from (R)-2-ethyl-piperazine-1,4-dicarboxylic acid 4-tert-butyl ester 1-[2,6-difluoro-3-(3-methoxy-propoxy)-benzyl] ester according to the procedure described in Example 207 to give the product as a colorless oil (44 mg; 56%); MS (ISP): 373.4 $(M+H)^+$.

Example 230

(R)-2-Ethyl-piperazine-1-carboxylic acid 4-cyclopropylmethoxy-2-chloro-6-fluoro-benzyl ester Chloro-5-fluoro-4-hydroxymethyl-phenol:

This compound was prepared from 3-chloro-5-fluorophenol and formaldehyde according to the procedure described in Example 179 to give the product as a colorless solid (26.4 g, 48%); m.p.: 125–127° C.; MS (EI): 176.1 $(M)^+$.

2-Chloro-4-cyclopropylmethoxy-6-fluoro-benzylalcohol:

This compound was prepared from 3-Chloro-5-fluoro-4-hydroxymethyl-phenol and cyclopropylmethylbromide according to the procedure described in Example 179 to give the product as a yellowish oil (305 mg, 77%); MS (EI): 230.1 $(M)^+$.

(R)-2-Ethyl-piperazine-1,4-dicarboxylic acid 4-tert-butyl ester 1-(2-chloro-4-cyclopropylmethoxy-6-fluoro-benzyl) ester:

This compound was prepared from 2-Chloro-4-cyclopropylmethoxy-6-fluoro-benzylalcohol and (R)-4-chlorocarbonyl-3-ethyl-piperazine-1-carboxylic acid tert-butyl ester according to the procedure described in Example 179 to give the product as a colorless oil (580 mg; 95%); MS (ISP): 488.4 $(M+NH4)^+$.

(R)-2-Ethyl-piperazine-1-carboxylic acid 2-chloro-4-cyclopropylmethoxy-6-fluoro-benzyl ester:

This compound was prepared from (R)-2-ethyl-piperazine-1,4-dicarboxylic acid 4-tert-butyl ester 1-(2-chloro-4-cyclopropylmethoxy-6-fluoro-benzyl) ester according to the procedure described in Example 179 to give the product as a colorless oil (284 mg, 63%); MS (ISP): 371.3 $(M+H)^+$.

Example 231

(R)-2-Ethyl-piperazine-1-carboxylic acid 2-chloro-6-fluoro-4-propoxy-benzyl ester 2-Chloro-6-fluoro-4-propoxy-benzylalcohol:

This compound was prepared from 3-Chloro-5-fluoro-4-hydroxymethyl-phenol and propylbromide according to the procedure described in Example 179 to give the product as a yellowish oil (259 mg, 69%); MS (EI): 218.1 $(M)^+$.

(R)-2-Ethyl-piperazine-1,4-dicarboxylic acid 4-tert-butyl ester 1-(2-chloro-6-fluoro-4-propoxy-benzyl) ester:

This compound was prepared from 2-chloro-6-fluoro-4-propoxy-benzylalcohol and (R)-4-chlorocarbonyl-3-ethyl-piperazine-1-carboxylic acid tert-butyl ester according to the procedure described in Example 179 to give the product as a colorless oil (499 mg; 93%); MS (ISP): 476.3 $(M+NH4)^+$.

(R)-2-Ethyl-piperazine-1-carboxylic acid 2-chloro-6-fluoro-4-propoxy-benzyl ester:

This compound was prepared from (R)-2-ethyl-piperazine-1,4-dicarboxylic acid 4-tert-butyl ester 1-(2-chloro-6-fluoro-4-propoxy-benzyl) ester according to the procedure described in Example 179 to give the product as a colorless oil (262 mg, 68%); MS (ISP): 359.3 $(M+H)^+$.

Example 232

(R)-2-Ethyl-piperazine-1-carboxylic acid 2-chloro-6-fluoro-4-ethoxy-benzyl ester 2-Chloro-6-fluoro-4-ethoxy-benzylalcohol:

This compound was prepared from 3-chloro-5-fluoro-4-hydroxymethyl-phenol and ethylbromide according to the procedure described in Example 179 to give the product as a yellowish oil (209 mg, 60%); MS (EI): 204.1 $(M)^+$.

(R)-2-Ethyl-piperazine-1,4-dicarboxylic acid 4-tert-butyl ester 1-(2-chloro-6-fluoro-4-ethoxy-benzyl) ester:

This compound was prepared from 2-chloro-6-fluoro-4-ethoxy-benzylalcohol and (R)-4-chlorocarbonyl-3-ethyl-piperazine-1-carboxylic acid tert-butyl ester according to the procedure described in Example 179 to give the product as a colorless oil (418 mg; 94%); MS (ISP): 462.4 $(M+NH4)^+$.

(R)-2-Ethyl-piperazine-1-carboxylic acid 2-chloro-6-fluoro-4-ethoxy-benzyl ester:

This compound was prepared from (R)-2-ethyl-piperazine-1,4-dicarboxylic acid 4-tert-butyl ester 1-(2-chloro-6-fluoro-4-ethoxy-benzyl) ester according to the procedure described in Example 179 to give the product as a colorless oil (205 mg, 64%); MS (ISP): 345.4 $(M+H)^+$.

Example 233

(R)-2-Ethyl-piperazine-1-carboxylic acid 4-butoxy-2-chloro-6-fluoro-benzyl ester Butoxy-2-chloro-6-fluoro-benzylalcohol:

This compound was prepared from 3-chloro-5-fluoro-4-hydroxymethyl-phenol and butylbromide according to the procedure described in Example 179 to give the product as a yellowish oil (277 mg, 70%); MS (EI): 232.1 $(M)^+$.

(R)-2-Ethyl-piperazine-1,4-dicarboxylic acid 4-tert-butyl ester 1-(4-butoxy-2-chloro-6-fluoro-benzyl) ester:

This compound was prepared from 4-butoxy-2-chloro-6-fluoro-benzylalcohol and (R)-4-chlorocarbonyl-3-ethyl-piperazine-1-carboxylic acid tert-butyl ester according to the procedure described in Example 179 to give the product as a colorless oil (505 mg; 90%); MS (ISP): 490.4 $(M+NH4)^+$.

(R)-2-Ethyl-piperazine-1-carboxylic acid 4-butoxy-2-chloro-6-fluoro-benzyl ester:

This compound was prepared from (R)-2-ethyl-piperazine-1,4-dicarboxylic acid 4-tert-butyl ester 1-(4-butoxy-2-chloro-6-fluoro-benzyl) ester according to the procedure described in Example 179 to give the product as a colorless oil (286 mg; 73%); MS (ISP): 373.4 $(M+H)^+$.

Example 234

(R)-2-Ethyl-piperazine-1-carboxylic acid 4-allyloxy-2-chloro-6-fluoro-benzyl ester Allyloxy-2-chloro-6-fluoro-benzylalcohol:

This compound was prepared from 3-chloro-5-fluoro-4-hydroxymethyl-phenol and allylbromide according to the procedure described in Example 179 to give the product as a yellowish oil (221 mg, 60%); MS (EI): 216.1 $(M)^+$.

(R)-2-Ethyl-piperazine-1,4-dicarboxylic acid 4-tert-butyl ester 1-(4-allyloxy-2-chloro-6-fluoro-benzyl) ester:

This compound was prepared from 4-allyloxy-2-chloro-6-fluoro-benzylalcohol and (R)-4-chlorocarbonyl-3-ethyl-piperazine-1-carboxylic acid tert-butyl ester according to the procedure described in Example 179 to give the product as a colorless oil (405 mg; 87%); MS (ISP): 474.4 $(M+NH4)^+$.

(R)-2-Ethyl-piperazine-1-carboxylic acid 4-allyloxy-2-chloro-6-fluoro-benzyl ester:

This compound was prepared from (R)-2-ethyl-piperazine-1,4-dicarboxylic acid 4-tert-butyl ester 1-(4-allyloxy-2-chloro-6-fluoro-benzyl) ester according to the procedure described in Example 179 to give the product as a colorless oil (242 mg; 78%); MS (ISP): 357.3 $(M+H)^+$.

Example 235

(R)-2-Ethyl-piperazine-1-carboxylic acid 2-chloro-6-fluoro-4-prop-2-ynyloxy-benzyl ester 2-Chloro-6-fluoro-4-prop-2-ynyloxy-benzylalcohol:

This compound was prepared from 3-chloro-5-fluoro-4-hydroxymethyl-phenol and propargylbromide according to the procedure described in Example 179 to give the product as a yellowish oil (212 mg, 58%); MS (EI): 214.1 $(M)^+$.

(R)-2-Ethyl-piperazine-1,4-dicarboxylic acid 4-tert-butyl ester 1-(2-chloro-6-fluoro-4-prop-2-ynyloxy-benzyl) ester:

This compound was prepared from 2-chloro-6-fluoro-4-prop-2-ynyloxy-benzylalcohol and (R)-4-chlorocarbonyl-3-ethyl-piperazine-1-carboxylic acid tert-butyl ester according to the procedure described in Example 179 to give the product as a colorless oil (357 mg; 80%); MS (ISP): 472.3 $(M+NH4)^+$.

(R)-2-Ethyl-piperazine-1-carboxylic acid 2-chloro-6-fluoro-4-prop-2-ynyloxy-benzyl ester:

This compound was prepared from (R)-2-ethyl-piperazine-1,4-dicarboxylic acid 4-tert-butyl ester 1-(2-chloro-6-fluoro-4-prop-2-ynyloxy-benzyl) ester according to the procedure described in Example 179 to give the product as a colorless oil (203 mg; 74%); MS (ISP): 355.3 $(M+H)^+$.

Example 236

(R)-2-Ethyl-piperazine-1-carboxylic acid 2-chloro-6-fluoro-4-(2-methoxy-ethoxy)-benzyl ester 2-Chloro-6-fluoro-4-(2-methoxy-ethoxy)-benzylalcohol:

This compound was prepared from 3-chloro-5-fluoro-4-hydroxymethyl-phenol and (2-bromoethyl) methyl ether according to the procedure described in Example 179 to give the product as a yellowish oil (209 mg, 52%); MS (EI): 234.1 $(M)^+$.

(R)-2-Ethyl-piperazine-1,4-dicarboxylic acid 4-tert-butyl ester 1-(2-chloro-6-fluoro-4-(2-methoxy-ethoxy)-benzyl) ester:

This compound was prepared from 2-chloro-6-fluoro-4-(2-methoxy-ethoxy)-benzylalcohol and (R)-4-chlorocarbonyl-3-ethyl-piperazine-1-carboxylic acid tert-butyl ester according to the procedure described in Example 179 to give the product as a colorless oil (370 mg; 89%); MS (ISP): 492.3 $(M+NH4)^+$.

(R)-2-Ethyl-piperazine-1-carboxylic acid 2-chloro-6-fluoro-4-(2-methoxy-ethoxy)-benzyl ester:

This compound was prepared from (R)-2-ethyl-piperazine-1,4-dicarboxylic acid 4-tert-butyl ester 1-(2-chloro-6-fluoro-4-(2-methoxy-ethoxy)-benzyl) ester according to the procedure described in Example 179 to give the product as a colorless oil (214 mg; 75%); MS (ISP): 375.4 $(M+H)^+$.

Example 237

(R)-2-Ethyl-piperazine-1-carboxylic acid 2-chloro-6-fluoro-4-(3-methoxy-propoxy)-benzyl ester 2-Chloro-6-fluoro-4-(3-methoxy-propoxy)-benzylalcohol:

This compound was prepared from 3-chloro-5-fluoro-4-hydroxymethyl-phenol and toluene-4-sulfonic acid 3-methoxy-propyl ester according to the procedure described in Example 179 to give the product as a yellowish oil (382 mg, 90%); MS (EI): 248.1 $(M)^+$.

(R)-2-Ethyl-piperazine-1,4-dicarboxylic acid 4-tert-butyl ester 1-(2-chloro-6-fluoro-4-(3-methoxy-propoxy)-benzyl) ester:

This compound was prepared from 2-chloro-6-fluoro-4-(3-methoxy-propoxy)-benzylalcohol and (R)-4-chlorocarbonyl-3-ethyl-piperazine-1-carboxylic acid tert-butyl ester according to the procedure described in Example 179 to give the product as a colorless oil (576 mg; 77%); MS (ISP): 506.4 $(M+NH4)^+$.

(R)-2-Ethyl-piperazine-1-carboxylic acid 2-chloro-6-fluoro-4-(3-methoxy-propoxy)-benzyl ester:

This compound was prepared from (R)-2-ethyl-piperazine-1,4-dicarboxylic acid 4-tert-butyl ester 1-(2-chloro-6-fluoro-4-(3-methoxy-propoxy)-benzyl) ester according to the procedure described in Example 179 to give the product as a colorless oil (254 mg; 56%); MS (ISP): 389.3 $(M+H)^+$.

Example 238

(R)-2-Ethyl-piperazine-1-carboxylic acid 2-chloro-6-fluoro-4-(2-methyl-thiazol-4-ylmethoxy)-benzy ester 2-Chloro-6-fluoro-4-(2-methyl-thiazol-4-ylmethoxy)-benzylalcohol:

This compound was prepared from 3-chloro-5-fluoro-4-hydroxymethyl-phenol and 4-chloromethyl-2-thiazol according to the procedure described in Example 179 to give the product as a yellowish oil (421 mg, 86%); MS (EI): 287.0 $(M)^+$.

(R)-2-Ethyl-piperazine-1,4-dicarboxylic acid 4-tert-butyl ester 1-(2-chloro-6-fluoro-4-(2-methyl-thiazol-4-ylmethoxy)-benzyl) ester:

This compound was prepared from 2-chloro-6-fluoro-4-(2-methyl-thiazol-4-ylmethoxy)-benzylalcohol and (R)-4-chlorocarbonyl-3-ethyl-piperazine-1-carboxylic acid tert-butyl ester according to the procedure described in Example 179 to give the product as a colorless oil (582 mg; 75%); MS (ISP): 528.2 $(M+H)^+$.

(R)-2-Ethyl-piperazine-1-carboxylic acid 2-chloro-6-fluoro-4-(2-methyl-thiazol-4-ylmethoxy)-benzy ester:

This compound was prepared from (R)-2-ethyl-piperazine-1,4-dicarboxylic acid 4-tert-butyl ester 1-(2-chloro-6-fluoro-4-(2-methyl-thiazol-4-ylmethoxy)-benzyl) ester according to the procedure described in Example 179 to give the product as a colorless oil (413 mg; 89%); MS (ISP): 428.5 $(M+H)^+$.

Example A

Tablets containing the following ingredients can be manufactured in a conventional manner:

| Ingredients | Per tablet |
|---|---|
| Compound of formula I | 10.0–300.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
|---|---|
| Compound of formula I | 100.0 mg |
| Lactose | 150.0 mg |
| Maize starch | 20.0 mg |
| Talc | 5.0 mg |

Example C

Injection solutions can have the following composition:

| | |
|---|---|
| Compound of formula I | 10.0 mg |
| Sodium chloride | q.s mg |
| Water for injection solutions | ad 2.0 ml |

The invention claimed is:

1. A compound of formula (I):

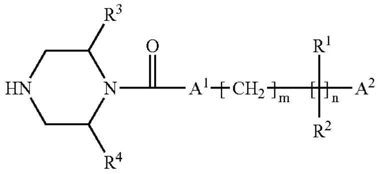

(I)

wherein $R^1$ and $R^2$ are independently selected from the group consisting of hydrogen, alkyl, cycloalkyl, aryl and aralkyl, or $R^1$ and $R^2$, together with the carbon atom to which they are attached, form an unsubstituted 3- to 8-membered carbocyclic ring or a 3 to 8 membered carbocyclic ring which is substituted with alkyl;

$R^3$ and $R^4$ are independently selected from the group consisting of hydrogen, alkyl, cycloalkyl, aryl and aralkyl;

$A^1$ is oxygen or sulfur;

$A^2$ is unsubstituted cycloalkyl or cycloalkyl substituted with at least one substituent independently selected from the group consisting of halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofliranylalkoxy, alkynyloxy and cycloalkylalkoxy, or aryl substituted with at least one substituent selected from the group consisting of fluorine, bromine, iodine, alkyl, cycloalkyl, aryl, aralkyl, ethoxy, propoxy, butoxy, 5-pentyloxy, aralkoxy, aryloxy, hydroxy, cyano, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, wherein the substituents of the substituted cycloalkyl and substituted aryl which are said alkyl, said cycloalkyl, said aryl, said aralkyl, said alkoxy, said ethoxy, said propoxy, said butoxy, said 5-pentyloxy, said aralkoxy, said aryloxy, said alkoxycarbonyl, said cycloalkoxycarbonyl, said aryloxycarbonyl, said aralkoxycarbonyl, said heteroaryloxycarbonyl, said cycloalkoxy, said alkylsulfonyloxy, said arylsulfonyloxy, said heteroarylalkoxy, said alkenyloxy, said tetrahydrofuranylalkoxy, said alkynyloxy and said cycloalkylalkoxy are optionally substituted with from one to three substituents independently selected from the group consisting of alkyl, alkoxy, halogen, nitro, oxo, trifluoromethyl, alkoxy substituted with from one to three halogen, thiophenyl, unsubstituted aryl, amino, alkylcarbonyl and unsubstituted aryloxy, or aryl substituted with at least one substituent selected from the group consisting of difluoromethoxy, cyclopropylmethoxy, and 3,5-dimethyl-isoxazol-4-ylmethoxy;

or two substituents of aryl or cycloalkyl form, together with the carbon atoms to which they are attached, an unsubstituted 5- to 7-membered carbocyclic ring or a substituted 5- to 7-membered carbocyclic ring with at least one substituent independently selected from the group consisting of alkyl, alkoxy and halogen;

n is 1 or 2; and m is zero or 1;

or a pharmaceutically acceptable salt, solvate or ester thereof provided that, 1-piperazinecarboxylic acid (4-(trifluoromethyl)phenyl)methyl ester, (amino-4 dimethoxy-6,7 quinazolyl-2)-1 cyclopropyl)-methoxycarbonyl-4 piperazine and 1-piperazinecarboxylic acid (2-ethoxyphenyl) methyl ester are excluded.

2. A compound of formula I according to claim 1, wherein $A^2$ is unsubstituted cycloalkyl or cycloalkyl substituted with at least one substituent independently selected from the group consisting of halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl and carbamoyl, or aryl substituted with at least one substituent selected from the group consisting of fluorine, bromine, iodine, alkyl, cycloalkyl, aryl, aralkyl, aralkoxy, aryloxy, hydroxy, cyano, amino, alkoxycarbonyl, cycloalkoxycarbonyl, aryloxycarbonyl, aralkoxycarbonyl, heteroaryloxycarbonyl and carbamoyl, wherein the substituents of the substituted cycloalkyl and substituted aryl which are said alkyl, said cycloalkyl, said aryl, said aralkyl, said alkoxy, said ethoxy, said propoxy, said butoxy, said 5-pentyloxy, said aralkoxy, said aryloxy, said alkoxycarbonyl, said cycloalkoxycarbonyl, said aryloxycarbonyl, said aralkoxycarbonyl and said heteroaryloxycarbonyl are optionally substituted with from one to three substituents independently selected from the group consisting of alkyl, alkoxy, halogen and nitro, or aryl substituted with at least one substituent selected from the group consisting of difluoromethoxy, cyclopropylmethoxy and 3,5-dimethyl-4-ylmethoxy;

or two substituents of aryl or cycloalkyl form together with the carbon atoms to which they are attached an unsubstituted 5- to 7-membered carbocyclic ring or a 5- to 7-membered ring substituted with alkyl, alkoxy or halogen; and m is zero.

3. A compound according to claim 1, wherein $R^3$ and $R^4$ are independently selected from hydrogen or alkyl.

4. A compound according to claim 3, wherein $R^3$ and $R^4$ are hydrogen.

5. A compound according to claim 3, wherein $R^3$ and $R^4$ are methyl.

6. A compound according to claim 3, wherein one of $R^3$ and $R^4$ is methyl or ethyl and the other of $R^3$ and $R^4$ is hydrogen.

7. A compound according to of claim 1, wherein $A^1$ is oxygen.

8. A compound according to of claim 1, wherein $A^1$ is sulfur.

9. A compound according to claim 1, wherein $R^1$ and $R^2$ are independently selected from the group consisting of hydrogen, alkyl and aryl.

10. A compound according to claim 1, wherein $A^2$ is phenyl substituted with from one to four substituents independently selected from the group consisting of fluorine, bromine, iodine, ethoxy, propoxy, butoxy, 5-pentyloxy, carbamoyloxy, heteroarylalkoxy, alkenyloxy, alkynyloxy and cycloalkylalkoxy, or wherein, said ethoxy, said propoxy, said butoxy, said 5-pentyloxy, said heteroarylalkoxy and said alkenyloxy are optionally substituted with between one and three substituents independently selected from alkyl and halogen;

or phenyl substituted with at least one substituent selected from the group consisting of difluoromethoxy, cyclopropylmethoxy, and 3,5-dimethyl-isoxazol-4-ylmethoxy.

11. A compound according to claim 1, wherein $A^2$ is phenyl substituted with from one to three substituents independently selected from the group consisting of fluoro, difluoromethoxy, propoxy, 3,5-dimethyl-isoxazol-4-ylmethoxy, 2-propenyloxy, 5-pentyloxy, cyclopropylmethoxy, 2-propynyloxy and NH(R')—C(O)—O—, wherein R' is selected from the group consisting of isopropyl, benzyl and tert.-butyl.

12. A compound according to claim 1, wherein n is 1.

13. A compound according to claim 12, wherein m is zero.

14. The compound according to claim 1, wherein the compound is selected from the group consisting of:

S-4-[(2-propylamino)carbonyl]oxybenzyl piperazine-1-thiocarboxylate;

S-4-[(benzylamino)carbonyl]oxybenzyl piperazine-1-thiocarboxylate;

S-4-[(tert-butylamino)carbonyl]oxybenzyl piperazine-1-thiocarboxylate;

2,6-difluoro-4-difluoromethoxybenzyl cis-2,6-dimethylpiperazine-1-carboxylate;

(R)-4-difluoromethoxybenzyl 2-ethylpiperazine-1-carboxylate;

(R)-2,6-difluoro-4-propoxybenzyl 2-methylpiperazine-1-carboxylate;

cis-2,6-dimethyl-piperazine-1-carboxylic acid 4-(3,5-dimethyl-isoxazol-4-ylmethoxy)-2,6-difluoro-benzyl ester;

2-fluoro-5-(2-propenyl)oxybenzyl cis-2,6-dimethylpiperazine-1-carboxylate;

(R)-2-fluoro-5-pentyloxybenzyl 2-methylpiperazine-1-carboxylate;

5-(cyclopropylmethyl)oxy-2-fluorobenzyl cis-2,6-dimethylpiperazine-1-carboxylate;

(R)-2-ethyl-piperazine-1-carboxylic acid 4-cyclopropylmethoxy-2,6-difluoro-benzyl ester;

(R)-2-ethyl-piperazine-1-carboxylic acid 2,6-difluoro-4-propoxy-benzyl ester;

(R)-2-ethyl-piperazine-1-carboxylic acid 4-allyloxy-2,6-difluoro-benzyl ester;

(R)-2-ethyl-piperazine-1-carboxylic acid 2,6-difluoro-4-prop-2-ynyloxy-benzyl ester;

(R)-2-ethyl-piperazine-1-carboxylic acid 4-cyclopropylmethoxy-2-chloro-6-fluoro-benzyl ester;

(R)-2-ethyl-piperazine-1-carboxylic acid 2-chloro-6-fluoro-4-propoxy-benzyl ester;

(R)-2-ethyl-piperazine-1-carboxylic acid 4-allyloxy-2-chloro-6-fluoro-benzyl ester; and (R)-2-ethyl-piperazine-1-carboxylic acid 2-chloro-6-fluoro-4-prop-2-ynyloxy-benzyl ester.

15. A compound of formula I according to claim 14, wherein the compound is S-4-[(2-propylamino)carbonyl]oxybenzyl piperazine-1-thiocarboxylate.

16. A compound of formula I according to claim 14, wherein the compound is S-4-[(benzylamino)carbonyl]oxybenzyl piperazine-1-thiocarboxylate.

17. A compound of formula I according to claim 14, wherein the compound is S-4-[(tert-butylamino)carbonyl]oxybenzyl piperazine-1-thiocarboxylate.

18. A compound of formula I according to claim 14, wherein the compound is 2,6-difluoro-4-difluoromethoxybenzyl cis-2,6-dimethylpiperazine-1-carboxylate.

19. A compound of formula I according to claim 14, wherein the compound is (R)-4-difluoromethoxybenzyl 2-ethylpiperazine-1-carboxylate.

20. A compound of formula I according to claim 14, wherein the compound is (R)-2,6-difluoro-4-propoxybenzyl 2-methylpiperazine-1-carboxylate.

21. A compound of formula I according to claim 14, wherein the compound is cis-2,6-dimethyl-piperazine-1-carboxylic acid 4-(3,5-dimethyl-isoxazol-4-ylmethoxy)-2,6-difluoro-benzyl ester.

22. A compound of formula I according to claim 14, wherein the compound is 2-fluoro-5-(2-propenyl)oxybenzyl cis-2,6-dimethylpiperazine-1-carboxylate.

23. A compound of formula I according to claim 14, wherein the compound is (R)-2-fluoro-5-pentyloxybenzyl 2-methylpiperazine-1-carboxylate.

24. A compound of formula I according to claim 14, wherein the compound is 5-(cyclopropylmethyl)oxy-2-fluorobenzyl cis-2,6-dimethylpiperazine-1-carboxylate.

25. A compound of formula I according to claim 14, wherein the compound is (R)-2-ethyl-piperazine-1-carboxylic acid 4-cyclopropylmethoxy-2,6-difluoro-benzyl ester.

26. A compound of formula I according to claim 14, wherein the compound is (R)-2-ethyl-piperazine-1-carboxylic acid 2,6-difluoro-4-propoxy-benzyl ester.

27. A compound of formula I according to claim 14, wherein the compound is (R)-2-ethyl-piperazine-1-carboxylic acid 4-allyloxy-2,6-difluoro-benzyl ester.

28. A compound of formula I according to claim 14, wherein the compound is (R)-2-ethyl-piperazine-1-carboxylic acid 2,6-difluoro-4-prop-2-ynyloxy-benzyl ester.

29. A compound of formula I according to claim 14, wherein the compound is (R)-2-ethyl-piperazine-1-carboxylic acid 4-cyclopropylmethoxy-2-chloro-6-fluoro-benzyl ester.

30. A compound of formula I according to claim 14, wherein the compound is (R)-2-ethyl-piperazine-1-carboxylic acid 2-chloro-6-fluoro-4-propoxy-benzyl ester.

31. A compound of formula I according to claim 14, wherein the compound is (R)-2-ethyl-piperazine-1-carboxylic acid 4-allyloxy-2-chloro-6-fluoro-benzyl ester.

32. A compound of formula I according to claim 14, wherein the compound is (R)-2-ethyl-piperazine-1-carboxylic acid 2-chloro-6-fluoro-4-prop-2-ynyloxy-benzyl ester.

33. A process for the preparation of a compound according to claim 1, comprising deprotecting a compound of formula (VI)

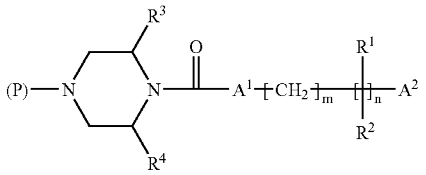

wherein $R^1$ to $R^4$, $A^1$, $A^2$, m and n are defined as in claim 1 and (P) is a nitrogen protecting group.

34. A pharmaceutical composition comprising a compound of formula I or a pharmaceutically acceptable salt, solvate or ester thereof and a therapeutically inert carrier, wherein the compound of formula I is:

(I)

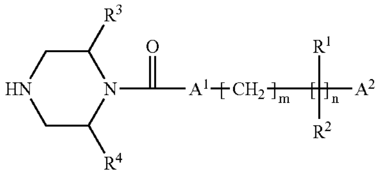

wherein $R^1$ and $R^2$ are independently selected from the group consisting of hydrogen, alkyl, cycloalkyl, aryl and aralkyl, or $R^1$ and $R^2$, together with the carbon atom to which they are attached, form an unsubstituted 3- to 8-membered carbocyclic ring or a 3 to 8 membered carbocyclic ring which is substituted with alkyl;

$R^3$ and $R^4$ are independently selected from the group consisting of hydrogen, alkyl, cycloalkyl, aryl and aralkyl;

$A^1$ is oxygen or sulfur, wherein in case $A^1$ is oxygen and $A^2$ is unsubstituted phenyl, one of $R^1$, $R^2$, $R^3$ and $R^4$ is not hydrogen;

$A^2$ is unsubstituted cycloalkyl or cycloalkyl substituted with at least one substituent independently selected from the group consisting of halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, or aryl substituted with at least one substituent selected from the group consisting of halogen, alkyl, cycloalkyl, aryl, aralkyl, alkoxy, aralkoxy, aryloxy, hydroxy, cyano, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, wherein the substituents of the substituted cycloalkyl and substituted aryl which are said alkyl, said cycloalkyl, said aryl, said aralkyl, said alkoxy, said aralkoxy, said aryloxy, said alkoxycarbonyl, said cycloalkoxycarbonyl, said aryloxycarbonyl, said aralkoxycarbonyl, said heteroaryloxycarbonyl, said cycloalkoxy, said alkylsulfonyloxy, said arylsulfonyloxy, said heteroarylalkoxy, said alkenyloxy, said tetrahydrofuranylalkoxy, said alkynyloxy and said cycloalkylalkoxy are optionally substituted with from one to three substituents independently selected from the group consisting of alkyl, alkoxy, halogen, nitro, oxo, trifluoromethyl, alkoxy substituted with from one to three halogen, thiophenyl, unsubstituted aryl, amino, alkylcarbonyl and unsubstituted aryloxy, or two substituents of aryl or cycloalkyl form, together with the carbon atoms to which they are attached, an unsubstituted 5- to 7-membered carbocyclic ring or a substituted 5- to 7-membered carbocyclic ring with at least one substituent independently selected from the group consisting of alkyl, alkoxy and halogen;

n is 1 or 2; and m is zero or 1;

provided that 1-piperazinecarboxylic acid (4-(trifluoromethyl)phenyl)methyl ester is excluded.

35. The pharmaceutical composition of claim 34 further comprising a therapeutically effective amount of a lipase inhibitor.

36. The pharmaceutical composition of claim 35 wherein said lipase inhibitor is orlistat.

37. A method of treating obesity comprising administering a therapeutically effective amount of a compound of formula I or a pharmaceutically acceptable salt, solvate or ester thereof to a patient in need of such treatment, wherein the compound of formula I is:

(I)

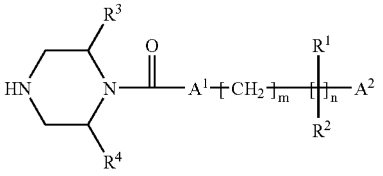

wherein $R^1$ and $R^2$ are independently selected from the group consisting of hydrogen, alkyl, cycloalkyl, aryl and aralkyl, or $R^1$ and $R^2$, together with the carbon atom to which they are attached, form an unsubstituted 3- to 8-membered carbocyclic ring or a 3 to 8 membered carbocyclic ring which is substituted with alkyl;

$R^3$ and $R^4$ are independently selected from the group consisting of hydrogen, alkyl, cycloalkyl, aryl and aralkyl;

$A^1$ is oxygen or sulfur, wherein in case $A^1$ is oxygen and $A^2$ is unsubstituted phenyl, one of $R^1$, $R^2$, $R^3$ and $R^4$ is not hydrogen;

$A^2$ is unsubstituted cycloalkyl or cycloalkyl substituted with at least one substituent independently selected from the group consisting of halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, or aryl substituted with at least one substituent selected from the group consisting of halogen, alkyl, cycloalkyl, aryl, aralkyl, alkoxy, aralkoxy, aryloxy, hydroxy, cyano, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, wherein the substituents of the substituted cycloalkyl and substituted aryl which are said alkyl, said cycloalkyl, said aryl, said aralkyl, said alkoxy, said aralkoxy, said aryloxy, said alkoxycarbonyl, said cycloalkoxycarbonyl, said aryloxycarbonyl, said aralkoxycarbonyl, said heteroaryloxycarbonyl, said cycloalkoxy, said alkylsulfonyloxy, said arylsulfonyloxy, said heteroarylalkoxy, said alkenyloxy, said tetrahydrofuranylalkoxy, said alkynyloxy and said cycloalkylalkoxy are optionally substituted with from one to three substituents independently selected from the group consisting of alkyl, alkoxy, halogen, nitro, oxo, trifluoromethyl, alkoxy substituted with from one to three halogen, thiophenyl, unsubstituted aryl, amino, alkylcarbonyl and unsubstituted aryloxy, or two substituents of aryl or cycloalkyl form, together with the carbon atoms to which they are attached, an unsubstituted 5- to 7-membered carbocyclic ring or a substituted 5- to 7-membered carbocyclic ring with at least one substituent independently selected from the group consisting of alkyl, alkoxy and halogen;

n is 1 or 2; and m is zero or 1;

provided that 1-piperazinecarboxylic acid (4-(trifluoromethyl)phenyl)methyl ester is excluded.

38. The method of claim 37 further comprising the administration of a therapeutically effective amount of a lipase inhibitor to the patient.

39. The method of treatment of claim 38 wherein said lipase inhibitor is orlistat.

40. A method of treatment of diabetes mellitus, Type I diabetes, Type II diabetes, diabetes, diabetes secondary to pancreatic disease, diabetes related to steroid use, Type III diabetes, hyperglycaemia, diabetic complication and insulin resistance, comprising administration of a therapeutically effective amount of the compound of formula I or a pharmaceutically effective salt solvate or ester thereof to a patient in need of such treatment, wherein the compound of formula I is:

(I)

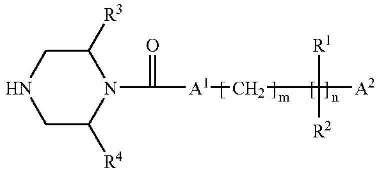

wherein $R^1$ and $R^2$ are independently selected from the group consisting of hydrogen, alkyl, cycloalkyl, aryl and aralkyl, or $R^1$ and $R^2$, together with the carbon atom to which they are attached, form an unsubstituted 3- to 8-membered carbocyclic ring or a 3 to 8 membered carbocyclic ring which is substituted with alkyl;

$R^3$ and $R^4$ are independently selected from the group consisting of hydrogen, alkyl, cycloalkyl, aryl and aralkyl;

$A^1$ is oxygen or sulfur, wherein in case $A^1$ is oxygen and $A^2$ is unsubstituted phenyl one of $R^1$, $R^2$, $R^3$ and $R^4$ is not hydrogen;

$A^2$ is unsubstituted cycloalkyl or cycloalkyl substituted with at least one substituent independently selected from the group consisting of halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, or aryl substituted with at least one substituent selected from the group consisting of halogen, alkyl, cycloalkyl, aryl, aralkyl, alkoxy, aralkoxy, aryloxy, hydroxy, cyano, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, wherein the substituents of the substituted cycloalkyl and substituted aryl which are said alkyl, said cycloalkyl, said aryl, said aralkyl, said alkoxy, said aralkoxy, said aryloxy, said alkoxycarbonyl, said cycloalkoxycarbonyl, said aryloxycarbonyl, said aralkoxycarbonyl, said heteroaryloxycarbonyl, said cycloalkoxy, said alkylsulfonyloxy, said arylsulfonyloxy, said heteroarylalkoxy, said alkenyloxy, said tetrahydrofuranylalkoxy, said alkynyloxy and said cycloalkylalkoxy are optionally substituted with from one to three substituents independently selected from the group consisting of alkyl, alkoxy, halogen, nitro, oxo, trifluoromethyl, alkoxy substituted with from one to three halogen, thiophenyl, unsubstituted aryl, amino, alkylcarbonyl and unsubstituted aryloxy, or two substituents of aryl or cycloalkyl form, together with the carbon atoms to which they are attached, an unsubstituted 5- to 7-membered carbocyclic ring or a substituted 5- to 7-membered carbocyclic ring with at least one substituent independently selected from the group consisting of alkyl, alkoxy and halogen;

n is 1 or 2; and m is zero or 1;

provided that 1-piperazinecarboxylic acid (4-(trifluoromethyl)phenyl)methyl ester is excluded.

41. A method of treatment of type II diabetes comprises administering a therapeutically effective amount of a compound of formula I or a pharmaceutically acceptable salt, solvate or ester thereof to a patient in need of such treatment, wherein the compound of formula I is:

(I)

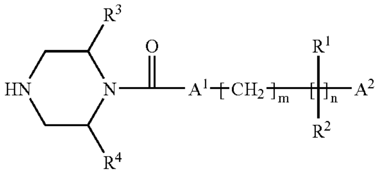

wherein $R^1$ and $R^2$ are independently selected from the group consisting of hydrogen, alkyl, cycloalkyl, aryl and aralkyl, or $R^1$ and $R^2$, together with the carbon atom to which they are attached, form an unsubstituted 3- to 8-membered carbocyclic ring or a 3 to 8 membered carbocyclic ring which is substituted with alkyl;

$R^3$ and $R^4$ are independently selected from the group consisting of hydrogen, alkyl, cycloallcyl, aryl and aralkyl;

$A^1$ is oxygen or sulfur, wherein in case $A^1$ is oxygen and $A^2$ is unsubstituted phenyl, one of $R^1$, $R^2$, $R^3$ and $R^4$ is not hydrogen;

$A^2$ is unsubstituted cycloalkyl or cycloalkyl substituted with at least one substituent independently selected from the group consisting of halogen, alkyl, cycloalkyl, aryl, aralkyl, alkoxy, aralkoxy, aryloxy, hydroxy, cyano, nitro, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, or aryl substituted with at least one substituent selected from the group consisting of halogen, alkyl, cycloalkyl, aryl, aralkyl, alkoxy, aralikoxy, aryloxy, hydroxy, cyano, amino, alkoxycarbonyl, cycloalkoxycarbonyl, aryloxycarbonyl, aralkoxycarbonyl, heteroaryloxycarbonyl, carbamoyl, cycloalkoxy, alkylsulfonyloxy, arylsulfonyloxy, carbamoyloxy, heteroarylalkoxy, alkenyloxy, tetrahydrofuranylalkoxy, alkynyloxy and cycloalkylalkoxy, wherein the substituents of the substituted cycloalkyl and substituted aryl which are said alkyl, said cycloalkyl, said aryl, said aralkyl, said alkoxy, said aralkoxy, said aryloxy, said alkoxycarbonyl, said cycloalkoxycarbonyl, said aryloxycarbonyl, said aralkoxycarbonyl, said heteroaryloxycarbonyl, said cycloalkoxy, said alkylsulfonyloxy, said arylsulfonyloxy, said heteroarylalkoxy, said alkenyloxy, said tetrahydrofuranylalkoxy, said alkynyloxy and said cycloalkylalkoxy are optionally substituted with from one to three substituents independently selected from the group consisting of alkyl, alkoxy, halogen, nitro, oxo, trifluoromethyl, alkoxy substituted with from one to three halogen, thiophenyl, unsubstituted aryl, amino, alkylcarbonyl and unsubstituted airyloxy, or two substituents of aryl or cycloalkyl form, together with the carbon atoms to which they are attached, an unsubstituted 5- to 7-membered carbocyclic ring or a substituted 5- to 7-membered carbocyclic ring with at least one substituent independently selected from the group consisting of alkyl, alkoxy and halogen;

n is 1 or 2; and m is zero or 1;

provided that 1-piperazinecarboxylic acid (4-(trifluoromethyl)phenyl)methyl ester is excluded.

42. The method of treatment of claim 41, further comprising administration of a therapeutically effective amount of a lipase inhibitor to the patient.

43. The method of claim 42 wherein said lipase inhibitor is orlistat.

* * * * *

UNITED STATES PATENT AND TRADEMARK OFFICE

CERTIFICATE OF CORRECTION

PATENT NO. : 7,022,707 B2

APPLICATION NO. : 10/874662

DATED : April 4, 2006

INVENTOR(S) : Adams et al.

It is certified that error appears in the above-identified patent and that said Letters Patent is hereby corrected as shown below:

Title Page;

In col. 1, (73) Assignee: Delete "Hoffman" and insert -- Hoffmann --.

In col. 1, (30) Foreign Application Priority, delete "(EP)" and insert -- GB --.

In claim 1, col. 103, line 44, delete "tetrahydrofliranylalkoxy," and insert --tetrahydrofuranylalkoxy, --.

Signed and Sealed this

Thirtieth Day of October, 2007

JON W. DUDAS

*Director of the United States Patent and Trademark Office*